(12) United States Patent
Cho et al.

(10) Patent No.: US 6,380,372 B1
(45) Date of Patent: Apr. 30, 2002

(54) BARLEY GENE FOR THIOREDOXIN AND NADP-THIOREDOXIN REDUCTASE

(75) Inventors: Myeong-Je Cho, Alameda; Gregorio del Val, El Cerrito, both of CA (US); Maxime Caillau, Verdun sur Garonne (FR); Peggy G. Lemaux, Moraga; Bob B. Buchanan, Berkeley, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/540,014

(22) Filed: Mar. 31, 2000

Related U.S. Application Data

(60) Provisional application No. 60/127,198, filed on Mar. 31, 1999, provisional application No. 60/169,162, filed on Dec. 6, 1999, provisional application No. 60/177,740, filed on Jan. 21, 2000, and provisional application No. 60/177,739, filed on Jan. 21, 2000.

(51) Int. Cl.$^7$ ............................ C07H 21/02; A01H 5/00; C12N 15/63
(52) U.S. Cl. .................... 536/23.1; 435/320.1; 435/410; 435/252.1; 435/69.1; 435/183; 800/295; 800/298; 800/278; 530/412
(58) Field of Search ...................... 536/23.1; 435/320.1, 435/410, 252.1, 69.1, 183; 800/295, 298, 278; 530/412

(56) References Cited

FOREIGN PATENT DOCUMENTS

| JP | 62-61783 | 9/1994 |
|----|----------|--------|
| WO | WO 96/03505 | 2/1996 |
| WO | WO 00/36126 | 6/2000 |

OTHER PUBLICATIONS

Shi et al. Plant Molecular Biology. 32:653–662, 1996.*
EMBL Sequence Database ID No. 022751 NADPH reductase, Jan. 1998.
Gautier, M.–F., et al., "Characterization of wheat thioredoxin h cDNA and production of an active Triticum aestivum protein in *Escherichia coli*" *Eur. J. Biochem.* 252:314–324 (1998).

* cited by examiner

Primary Examiner—Jeffrey Fredman
Assistant Examiner—Juliet C. Einsmann
(74) Attorney, Agent, or Firm—Morrison & Foerster L.L.P.

(57) ABSTRACT

The present invention provides barley thioredoxin h nucleic acids and proteins. The barley thioredoxin h nucleic acid may be isolated or it may be an expression vector. The expression vector may be operably linked to a transcriptional regulatory sequence. The invention also provides for transgenic plants comprising recombinant barley thioredoxin h. The invention also provides methods of expressing and purifying barley thioredoxin h.

25 Claims, 19 Drawing Sheets

A

```
1   MECSAAAPLRTRVCIIGSGPAAHTAAIYAARAELKPVLFEGWMANDIAAGGQLTTTIDVP   H. vulgare NTR
1   MNCLETH--NTRLCIVGSGPAAHTAAIYAARAELKPLLFEGWMANDIAEGGQINQPPR-E   A. thaliana NTR
1   MGTTK----HSKLLILGSGPAGYTAAVYAARANLQPVIITG-----MEKGGQLTTTIEVE   E. coli NTR 61  NFPGFETGIMGIDLMDNCRAQSVREGTNILSETVIEVDFSARPFRVTSDSTTVLADTVVV   H. vulgare NTR
58  NFPGFEEGILCVELTLKFRKQSEREGTTIFTETVTKVDFSSKPFKIFTDSKAILADAVIL   A. thaliana NTR
52  NWEGDLNDLTCPLLVERMHEHATKFETELIFDHINKVDLQNRPFRINGLNGEYTQDALII   E. coli NTR 121 ATGAVARRIHFSGSDT----YWNRGISACAVCDGAAPIFRNKFLAVIGGGDSAMEEGNFL   H. vulgare NTR
118 AIGAVAKWLSEVGSGEVLGGLWNRGISACAVCDGAAPIFRNKPLAVIGGGDSAMEEANFL   A. thaliana NTR
112 ATGASARYLGLPSEEA----FKGRCVSACATCDGF--FYRNQKVAVIGGGNTAVEEALYL   E. coli NTR 177 TKYGSCVVYITHRFNTFRASKIMQARALSNPKI-QVWWDSEVVEAYGGAGGGELAGVKVKN   H. vulgare NTR
178 TKYGSKVYIIDRRDAFRASKIMCQRALSNPKI-DVIWNSSVVEAYGDGERDVLGGLKVKN   A. thaliana NTR
166 SNIASEVHLIHRRLGFRAEKILIKRLMDKVENGNIILHTNRTLEEVTGDQMGVIGVRLRD   E. coli NTR 236 LVTGE-VSDIQVSGLFFAIGHEPATKFLNGQLELHADGYVATKPG----STHTSVEGVFA   H. vulgare NTR
237 WVTGD-VSDIKVSGLFFAIGHEPATKFLDGGVELDSDGYVVTKPG----TTQTSVPGVFA   A. thaliana NTR
226 TQNSDNIESIDVAGLFVAIGHSPNTAIFEGQLELE-NGYIKVQSCIHGNATQTSIPGVFA   E. coli NTR 291 AGDVQDKKYRQAITAACSGCMAALDAEHYLQEVGAQVGKSDZ   H. vulgare NTR
292 AGDVQDKKYRQAITAAGTGCMAALDAEHYLQEIGSQQGKSD    A. thaliana NTR
285 AGDVMDHIYRQATTSAGTGCMAALDAERYLDGLADAK        E. coli NTR
```

Decoration 'Decoration #1': Shade (with solid black) residues that match the Consensus exactly.

B

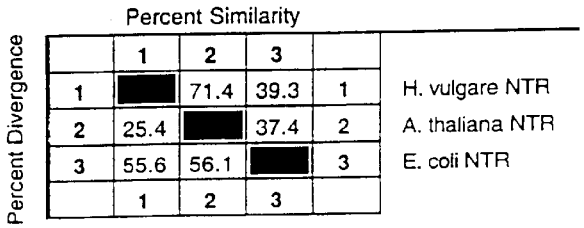

C

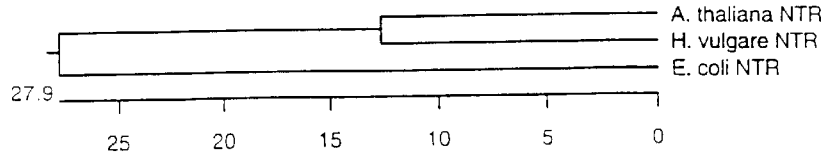

| | 1 | 2 | 3 | |
|---|---|---|---|---|
| 1 | | 58.2 | 40.5 | 1 |
| 2 | 32.7 | | 34.9 | 2 |
| 3 | 45.3 | 45.0 | | 3 |
| | 1 | 2 | 3 | |

Percent Similarity (top), Percent Divergence (left)

1 — H. vulgare NTR
2 — A. thaliana NTR
3 — E. coli NTR

D

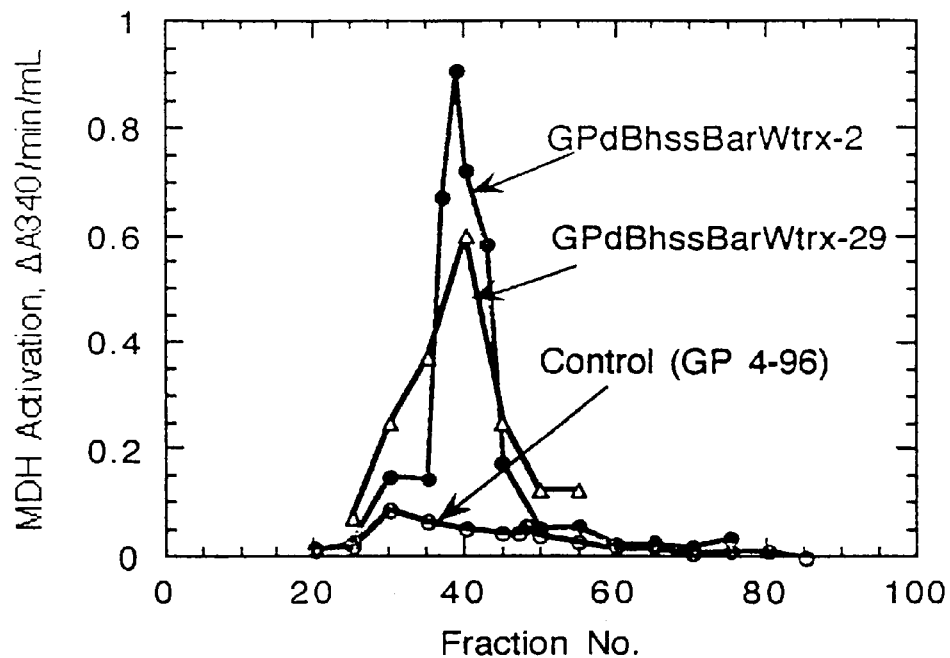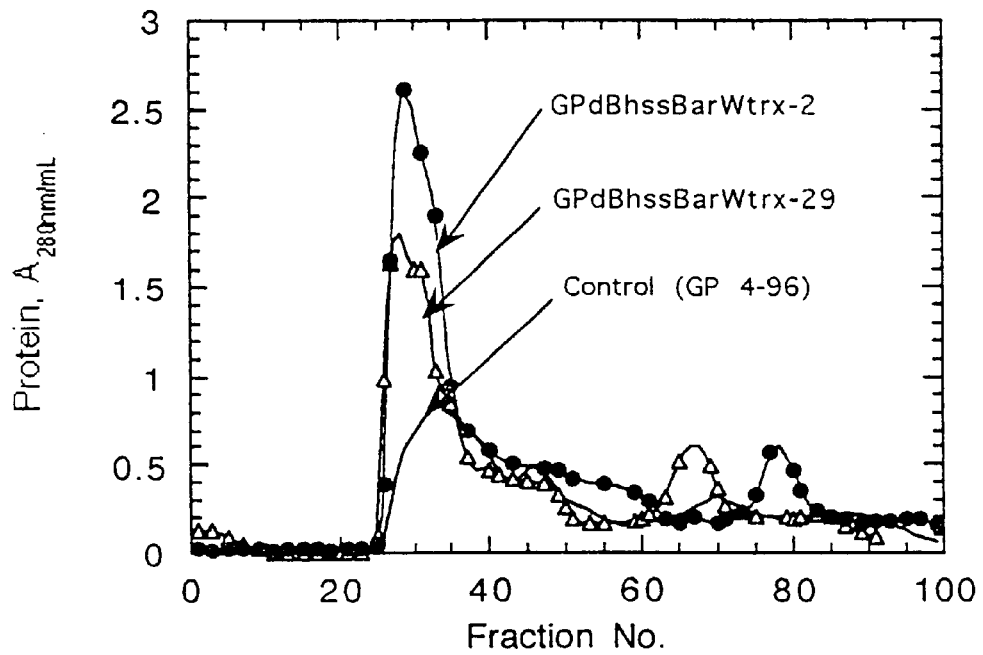
FIGURE 7

1. Wheat germ thioredoxin
2. Control (GP 4-96), nontransformed
3. Control, null segregant (GPdBssBarWtrx-29-11-10)
4. Transformed, heterozygous line (GPdBssBarWtrx-29)
5. Transformed, homozygous line 1 (GPdBssBarWtrx-29-3)
6. Transformed, homozygous line 2 (GPdBssBarWtrx-29-3-2)
7. Prestained standards AAGCTTTAACAACCCACACATTGATTGCAACTTAGTCCTACACAAGTTT
TCCATTCTTGTTTCAGGCTAACAACCTATACAAGGTTCCAAAATCATGC
AAAAGTGATGCTAGGTTGATAATGTGTGACATGTAAAGTGAATAAGG
TGAGTCATGCATACCAAACCTCGGGATTTCTATACTTTGTGTATGATCA
TATGCACAACTAAAAGGCAACTTTGATTATCAATTGAAAAGTACCG
CTTGTAGCTTGTGCAACCTAACACAATGTCCAAAAATCCATTTGCAAA
AGCATCCAAACACAATTGTTAAAGCTGTTCAAACAAACAAAGAAGAG
ATGAAGCCTGGCTACTATAAATAGGCAGGTAGTATAGAGATCTACACA
AGCACAAGCATCAAAACCAAGAAACACTAGTTAACACCAATCCACTA
TGAAGACCTTCCTCATCTTTGCACTCCTCGCCATTGCGGCAACAAGTACG
ATTGCA

FIGURE 11

CTTCGAGTGCCCGCCGATTTGCCAGCAATGGCTAACAGACACATATTCT
GCCAAAACCCCAGAACAATAATCACTTCTCGTAGATGAAGAGAACAG
ACCAAGATACAAACGTCCACGCTTCAGCAAACAGTACCCAGAACTAG
GATTAAGCCGATTACGCGGCTTTAGCAGACCGTCCAAAAAAACTGTTTT
GCAAAGCTCCAATTCCTCCTTGCTTATCCAATTTCTTTTGTGTTGGCAAA
CTGCACTTGTCCAACCGATTTGTTCTTCCCGTGTTTCTTCTTAGGCTAAC
TAACACAGCCGTGCACATAGCCATGGTCCGGAATCTTCACCTCGTCCCT
ATAAAAGCCCAGCCAATCTCCACAATCTCATCATCACCGAGAACACCG
AGAACCACAAAACTAGAGATCAATTCATTGACAGTCCACCGAGATGGC
TAAGCGGCTGGTCCTCTTTGTGGCGGTAATCGTCGCCCTCGTGGCTCTCA
CCACCGCT

FIGURE 12

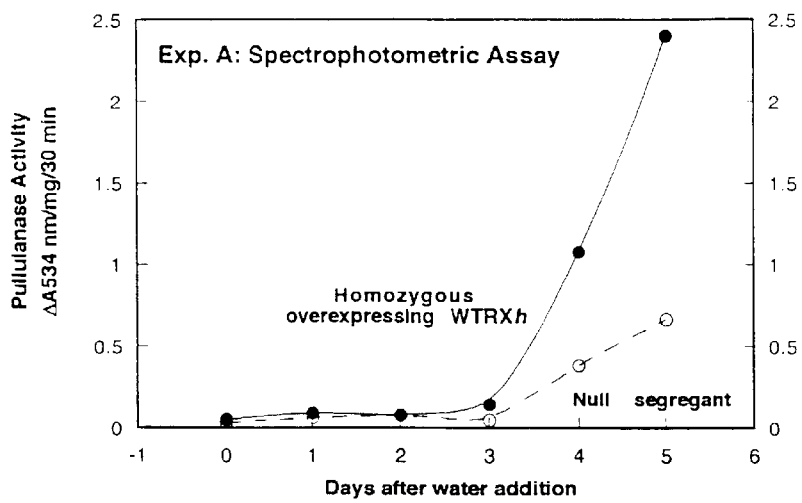
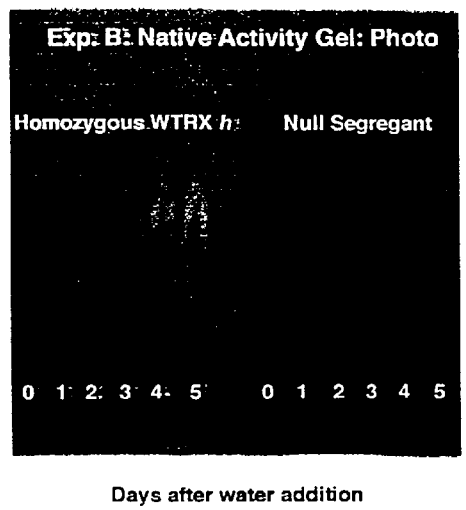
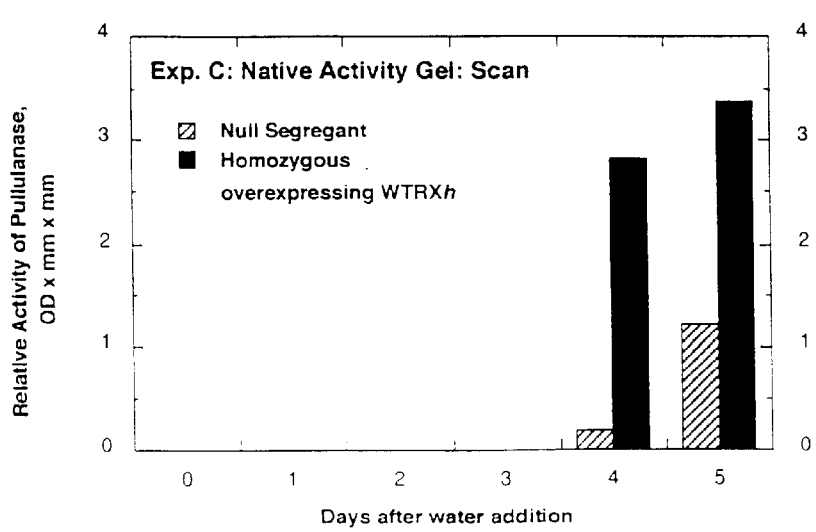
FIGURE 13

SEQUENCE LISTING

```
<160> NUMBER OF SEQ ID NOS: 51

<210> SEQ ID NO 1
<211> LENGTH: 369
<212> TYPE: DNA
<213> ORGANISM: Artificial Sequence
<220> FEATURE:
<223> OTHER INFORMATION: barley thioredoxin h cDNA

<400> SEQUENCE: 1
atggcggcgt cggcaacggc ggcggcagtg gcggcggagg tgatctcggt ccacagcctg      60
gagcagtgga ccatgcagat cgaggaggcc aacaccgcca agaagctggt ggtgattgac     120
ttcactgcat catggtgcgg accatgccgc atcatggctc cagttttcgc tgatctcgcc     180
aagaagttcc caaatgctgt tttcctcaag gtcgacgtgg atgaactgaa gcccattgct     240
gagcaattca gtgtcgaggc catgccaacg ttcctgttca tgaaggaagg agacgtcaag     300
gacagggttg tcggagctat caaggaggaa ctgaccgcca aggttgggct tcacgcggcg     360
```

```
                                                               gcccagtaa                                                                 369
```

<210> SEQ ID NO 2
<211> LENGTH: 122
<212> TYPE: PRT
<213> ORGANISM: Hordeum vulgare

<400> SEQUENCE: 2

```
Met Ala Ala Ser Ala Thr Ala Ala Val Ala Ala Glu Val Ile Ser
 1               5                  10                  15

Val His Ser Leu Glu Gln Trp Thr Met Gln Ile Glu Glu Ala Asn Thr
                20                  25                  30

Ala Lys Lys Leu Val Val Ile Asp Phe Thr Ala Ser Trp Cys Gly Pro
            35                  40                  45

Cys Arg Ile Met Ala Pro Val Phe Ala Asp Leu Ala Lys Lys Phe Pro
        50                  55                  60

Asn Ala Val Phe Leu Lys Val Asp Val Asp Glu Leu Lys Pro Ile Ala
65                  70                  75                  80

Glu Gln Phe Ser Val Glu Ala Met Pro Thr Phe Leu Phe Met Lys Glu
                85                  90                  95

Gly Asp Val Lys Asp Arg Val Val Gly Ala Ile Lys Glu Glu Leu Thr
            100                 105                 110

Ala Lys Val Gly Leu His Ala Ala Ala Gln
        115                 120
```

<210> SEQ ID NO 3
<211> LENGTH: 382
<212> TYPE: DNA
<213> ORGANISM: Artificial Sequence
<220> FEATURE:
<223> OTHER INFORMATION: wheat thioredoxin h cDNA

<400> SEQUENCE: 3

```
atggcggcgt cggcggcgac ggcgacggcg acggcggcgg cggtaggggc gggggaggtg      60
atctccgtcc acagcctgga gcagtggacc atgcagatcg aggaggccaa cgccgccaag     120
aagctggtgg tgattgactt cactgcatca tggtgcggac catgccgcat tatggctcca     180
attttcgctg atctcgccaa gaagttccca gctgctgttt tcctcaaggt cgacgttgat     240
gaactgaagc ccattgctga gcaattcagc gtggaggcca tgccaacctt cctgttcatg     300
aaggaaggag atgtcaagga cagggttgtc ggagctatca aggaggaact gacgaccaag     360
gttgggctac acgcggcccc ag                                              382
```

<210> SEQ ID NO 4
<211> LENGTH: 127
<212> TYPE: PRT
<213> ORGANISM: Triticum aestivum

<400> SEQUENCE: 4

```
Met Ala Ala Ser Ala Ala Thr Ala Thr Ala Ala Ala Val Gly
 1               5                  10                  15

Arg Gly Glu Val Ile Ser Val His Ser Leu Glu Gln Trp Thr Met Gln
                20                  25                  30

Ile Glu Glu Ala Asn Ala Ala Lys Lys Leu Val Val Ile Asp Phe Thr
            35                  40                  45

Ala Ser Trp Cys Gly Pro Cys Arg Ile Met Ala Pro Ile Phe Ala Asp
        50                  55                  60
```

```
Leu Ala Lys Lys Phe Pro Ala Ala Val Phe Leu Lys Val Asp Val Asp
 65                  70                  75                  80

Glu Leu Lys Pro Ile Ala Glu Gln Phe Ser Val Glu Ala Met Pro Thr
                 85                  90                  95

Phe Leu Phe Met Lys Glu Gly Asp Val Lys Asp Arg Val Val Gly Ala
                100                 105                 110

Ile Lys Glu Glu Leu Thr Thr Lys Val Gly Leu His Ala Ala Gln
            115                 120                 125
```

<210> SEQ ID NO 5
<211> LENGTH: 393
<212> TYPE: DNA
<213> ORGANISM: Artificial Sequence
<220> FEATURE:
<223> OTHER INFORMATION: wheat thioredoxin h cDNA

<400> SEQUENCE: 5

```
atggcggcgg cggcgacggc gacgactaca gcggcggcga cggcggcggc ggtggggccg      60
ggggaggtga tctccgtcca cagcctggag cagtggacca tgcagatcga ggaggccaac     120
gccgccaaga agctggtggt gattgacttc actgcatcat ggtgcggacc atgccgcatt     180
atggctccaa ttttttgctga tctcgccaag aagttcccag ctgctgtttt cctcaaggtc     240
gacgttgatg aactgaagcc cattgctgag caattcagcg tcgaggccat gccaaccttc     300
ctgttcatga aggaaggaga cgtcaaggac agggttgtcg gagctatcaa ggaggagctg     360
acgaccaagg ttgggctcca cgcggctgcc tag                                   393
```

<210> SEQ ID NO 6
<211> LENGTH: 130
<212> TYPE: PRT
<213> ORGANISM: Triticum durum

<400> SEQUENCE: 6

```
Met Ala Ala Ala Ala Thr Ala Thr Thr Thr Ala Ala Ala Thr Ala Ala
  1               5                  10                  15

Ala Val Gly Pro Gly Glu Val Ile Ser Val His Ser Leu Glu Gln Trp
                 20                  25                  30

Thr Met Gln Ile Glu Glu Ala Asn Ala Ala Lys Lys Leu Val Val Ile
             35                  40                  45

Asp Phe Thr Ala Ser Trp Cys Gly Pro Cys Arg Ile Met Ala Pro Ile
 50                  55                  60

Phe Ala Asp Leu Ala Lys Lys Phe Pro Ala Ala Val Phe Leu Lys Val
 65                  70                  75                  80

Asp Val Asp Glu Leu Lys Pro Ile Ala Glu Gln Phe Ser Val Glu Ala
                 85                  90                  95

Met Pro Thr Phe Leu Phe Met Lys Glu Gly Asp Val Lys Asp Arg Val
                100                 105                 110

Val Gly Ala Ile Lys Glu Glu Leu Thr Thr Lys Val Gly Leu His Ala
            115                 120                 125

Ala Ala
    130
```

<210> SEQ ID NO 7
<211> LENGTH: 26
<212> TYPE: DNA
<213> ORGANISM: Artificial Sequence
<220> FEATURE:
<223> OTHER INFORMATION: primer
<221> NAME/KEY: misc_feature

```
<222> LOCATION: (1)...(26)
<223> OTHER INFORMATION: n = I

<400> SEQUENCE: 7
gtaaagcntt aacaacccac acattg                                              26

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
ccgacgccgc tgcaatcgta cttgttgccg caat                                     34

<210> SEQ ID NO 9
<211> LENGTH: 332
<212> TYPE: PRT
<213> ORGANISM: Hordeum vulgare

<400> SEQUENCE: 9
```

Met Glu Gly Ser Ala Ala Ala Pro Leu Arg Thr Arg Val Cys Ile Ile
 1               5                  10                  15

Gly Ser Gly Pro Ala Ala His Thr Ala Ala Ile Tyr Ala Ala Arg Ala
            20                  25                  30

Glu Leu Lys Pro Val Leu Phe Glu Gly Trp Met Ala Asn Asp Ile Ala
        35                  40                  45

Ala Gly Gly Gln Leu Thr Thr Thr Asp Val Glu Asn Phe Pro Gly
    50                  55                  60

Phe Pro Thr Gly Ile Met Gly Ile Asp Leu Met Asp Asn Cys Arg Ala
65                  70                  75                  80

Gln Ser Val Arg Phe Gly Thr Asn Ile Leu Ser Glu Thr Val Thr Glu
                85                  90                  95

Val Asp Phe Ser Ala Arg Pro Phe Arg Val Thr Ser Asp Ser Thr Thr
            100                 105                 110

Val Leu Ala Asp Thr Val Val Ala Thr Gly Ala Val Ala Arg Arg
        115                 120                 125

Leu His Phe Ser Gly Ser Asp Thr Tyr Trp Asn Arg Gly Ile Ser Ala
    130                 135                 140

Cys Ala Val Cys Asp Gly Ala Ala Pro Ile Phe Arg Asn Lys Pro Ile
145                 150                 155                 160

Ala Val Ile Gly Gly Gly Asp Ser Ala Met Glu Glu Gly Asn Phe Leu
                165                 170                 175

Thr Lys Tyr Gly Ser Gln Val Tyr Ile Ile His Arg Arg Asn Thr Phe
            180                 185                 190

Arg Ala Ser Lys Ile Met Gln Ala Arg Ala Leu Ser Asn Pro Lys Ile
        195                 200                 205

Gln Val Val Trp Asp Ser Glu Val Glu Ala Tyr Gly Gly Ala Gly
    210                 215                 220

Gly Gly Pro Leu Ala Gly Val Lys Val Lys Asn Leu Val Thr Gly Glu
225                 230                 235                 240

Val Ser Asp Leu Gln Val Ser Gly Leu Phe Phe Ala Ile Gly His Glu
                245                 250                 255

Pro Ala Thr Lys Phe Leu Asn Gly Gln Leu Glu Leu His Ala Asp Gly
            260                 265                 270

Tyr Val Ala Thr Lys Pro Gly Ser Thr His Thr Ser Val Glu Gly Val

```
          275                 280                  285
  Phe Ala Ala Gly Asp Val Gln Asp Lys Lys Tyr Arg Gln Ala Ile Thr
          290                 295                  300
  Ala Ala Gly Ser Gly Cys Met Ala Ala Leu Asp Ala Glu His Tyr Leu
  305                 310                  315                  320
  Gln Glu Val Gly Ala Gln Val Gly Lys Ser Asp Glx
                  325                 330
```

<210> SEQ ID NO 10
<211> LENGTH: 995
<212> TYPE: DNA
<213> ORGANISM: Hordeum vulgare

<400> SEQUENCE: 10

```
atggagggat ccgccgcggc gccgctccgc acgcgcgtgt gcatcatcgg cagcggcccg      60
gccgcgcaca cggcggccat ctacgcggcc cgcgcggagc tcaagcccgt gctcttcgag     120
ggctggatgg ccaacgacat cgccgcgggg ggccagctca ccaccaccac cgacgtcgag     180
aacttccccg gattccccac cggcatcatg ggcatcgacc tcatggacaa ctgccgcgcc     240
cagtccgtcc gcttcggcac caacatcctc tccgagaccg tcaccgaggt cgacttctcc     300
gcccgcccct ccgcgtcac ctccgactcc accaccgtcc tcgccgacac cgtcgtcgtc     360
gccacgggcg ccgtcgcgcg ccgcctccat ttctccggtt ccgacaccta ctggaaccgc     420
ggcatctccg cctgcgccgt ctgcgacggc gctgcgccca tcttccggaa caagcccatc     480
gccgtcatcg gcggcggtga ttccgccatg gaggaaggca acttcctcac aagtacgga     540
tcccaagtgt acatcatcca cggcgcaac accttccgcg cctccaagat tatgcaggct     600
agggcgctct ccaatcctaa gatccaggtt gtctgggact cgaggtcgtc gaggcttacg     660
gcggtgcagg cggcggccca ttagctgggg tcaaggtcaa gaacttggtg actggtgagg     720
tgtctgacct tcaggtgtcc gggctttct cgccatcgg gcatgagccg ccaccaagt     780
ttctcaatgg gcagcttgag ctccatgccg atgggtatgt ggccaccaag ccgggctcta     840
cacataccag tgtggagggg tctttgctgc tggagacgtg caggataaga agtatcgtca     900
ggccattact gctgctggat caggttgcat ggctgctttg ggacgccgag cactatctgc     960
aggaggtggg tgcacaggtg ggcaagtctg attga                                995
```

<210> SEQ ID NO 11
<211> LENGTH: 486
<212> TYPE: DNA
<213> ORGANISM: barley

<400> SEQUENCE: 11

```
aagctttaac aacccacaca ttgattgcaa cttagtccta cacaagtttt ccattcttgt      60
ttcaggctaa caacctatac aaggttccaa aatcatgcaa aagtgatgct aggttgataa     120
tgtgtgacat gtaaagtgaa taaggtgagt catgcatacc aaacctcggg atttctatac     180
tttgtgtatg atcatatgca caactaaaag gcaactttga ttatcaattg aaaagtaccg     240
cttgtagctt gtgcaaccta acacaatgtc caaaatcca tttgcaaaag catccaaaca     300
caattgttaa agctgttcaa acaaacaaag aagagatgaa gcctggctac tataaatagg     360
caggtagtat agagatctac acaagcacaa gcatcaaaac caagaaacac tagttaacac     420
caatccacta tgaagacctt cctcatcttt gcactcctcg ccattgcggc aacaagtacg     480
attgca                                                                486
```

<210> SEQ ID NO 12
<211> LENGTH: 497
<212> TYPE: DNA
<213> ORGANISM: barley

<400> SEQUENCE: 12

```
cttcgagtgc cgccgattt gccagcaatg gctaacagac acatattctg ccaaaacccc      60
agaacaataa tcacttctcg tagatgaaga gaacagacca agatacaaac gtccacgctt     120
cagcaaacag taccccagaa ctaggattaa gccgattacg cggctttagc agaccgtcca     180
aaaaaactgt tttgcaaagc tccaattcct ccttgcttat ccaatttctt ttgtgttggc     240
aaactgcact tgtccaaccg attttgttct tcccgtgttt cttcttaggc taactaacac     300
agccgtgcac atagccatgg tccggaatct tcacctcgtc cctataaaag cccagccaat     360
ctccacaatc tcatcatcac cgagaacacc gagaaccaca aaactagaga tcaattcatt     420
gacagtccac cgagatggct aagcggctgg tcctctttgt ggcggtaatc gtcgccctcg     480
tggctctcac caccgct                                                    497
```

<210> SEQ ID NO 13
<211> LENGTH: 23
<212> TYPE: DNA
<213> ORGANISM: Artificial Sequence
<220> FEATURE:
<223> OTHER INFORMATION: degenerative primer

<400> SEQUENCE: 13

```
ttcttcgcsa tcggmcayga rcc                                              23
```

<210> SEQ ID NO 14
<211> LENGTH: 23
<212> TYPE: DNA
<213> ORGANISM: Artificial Sequence
<220> FEATURE:
<223> OTHER INFORMATION: degenerative primer

<400> SEQUENCE: 14

```
gcgtcsarrg crgccatgca scc                                              23
```

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15

```
acsacsacsa csgacgtsga raa                                              23
```

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16

```
actggtatgt gtagagccc                                                   19
```

<210> SEQ ID NO 17
<211> LENGTH: 20
<212> TYPE: DNA
<213> ORGANISM: Artificial Sequence
```

```
<220> FEATURE:
<223> OTHER INFORMATION: primer

<400> SEQUENCE: 17
aattaaccct cactaaaggg                                              20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
aagttctcga cgtcggtggt g                                            21

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
caggaaacag ctatgac                                                 17

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
attatgcagg ctagggcgct c                                            21

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
tatctagaat ggagggatcc gccgcggcgc                                   30

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
ttggtacctc aatcagactt gcccacctgt                                   30

<210> SEQ ID NO 23
<211> LENGTH: 995
<212> TYPE: DNA
<213> ORGANISM: Hordeum vulgare

<400> SEQUENCE: 23
atggagggat ccgccgcggc gccgctccgc acgcgcgtgt gcatcatcgg cagcggcccg    60
gccgcgcaca cggcggccat ctacgcggcc cgcgcggagc tcaagcccgt gctcttcgag   120
```

-continued

```
ggctggatgg ccaacgacat cgccgcgggg ggccagctca ccaccaccac cgacgtcgag      180
aacttccccg gattccccac cggcatcatg gcatcgacc  tcatggacaa ctgccgcgcc      240
cagtccgtcc gcttcggcac caacatcctc tccgagaccg tcaccgaggt cgacttctcc      300
gcccgcccct tccgcgtcac ctccgactcc accaccgtcc tcgccgacac cgtcgtcgtc      360
gccacgggcg ccgtcgcgcg ccgcctccat ttctccggtt ccgacaccta ctggaaccgc      420
ggcatctccg cctgcgccgt ctgcgacggc gctgcgccca tcttccggaa caagcccatc      480
gccgtcatcg gcgcggtga  ttccgccatg gaggaaggca acttcctcac caagtacgga      540
tcccaagtgt acatcatcca cgggcgcaac accttccgcg cctccaagat tatgcaggct      600
agggcgctct ccaatcctaa gatccaggtt gtctgggact cgaggtcgtc gaggcttacg      660
gcggtgcagg cggcggccca ttagctgggg tcaaggtcaa gaacttggtg actggtgagg      720
tgtctgacct tcaggtgtcc gggctttttct tcgccatcgg gcatgagccg gccaccaagt      780
ttctcaatgg gcagcttgag ctccatgccg atgggtatgt ggccaccaag ccgggctcta      840
cacataccag tgtggagggg tctttgctgc tggagacgtg caggataaga agtatcgtca      900
ggccattact gctgctggat caggttgcat ggctgctttg gacgccgag  cactatctgc      960 aggaggtggg tgcacaggtg ggcaagtctg attga                                 995
```

<210> SEQ ID NO 24
<211> LENGTH: 332
<212> TYPE: PRT
<213> ORGANISM: Arabidopsis thaliana

<400> SEQUENCE: 24

```
Met Asn Gly Leu Glu Thr His Asn Thr Arg Leu Cys Ile Val Gly Ser
 1               5                  10                  15

Gly Pro Ala Ala His Thr Ala Ala Ile Tyr Ala Ala Arg Ala Glu Leu
            20                  25                  30

Lys Pro Leu Leu Phe Glu Gly Trp Met Ala Asn Asp Ile Ala Pro Gly
        35                  40                  45

Gly Gln Leu Asn Gln Pro Pro Arg Glu Asn Phe Pro Gly Phe Pro Glu
    50                  55                  60

Gly Ile Leu Gly Val Glu Leu Thr Asp Lys Phe Arg Lys Gln Ser Glu
65                  70                  75                  80

Arg Phe Gly Thr Thr Ile Phe Thr Glu Thr Val Thr Lys Val Asp Phe
                85                  90                  95

Ser Ser Lys Pro Phe Lys Leu Phe Thr Asp Ser Lys Ala Ile Leu Ala
            100                 105                 110

Asp Ala Val Ile Leu Ala Ile Gly Ala Val Ala Lys Trp Leu Ser Phe
        115                 120                 125

Val Gly Ser Gly Glu Val Leu Gly Gly Leu Trp Asn Arg Gly Ile Ser
    130                 135                 140

Ala Cys Ala Val Cys Asp Gly Ala Ala Pro Ile Phe Arg Asn Lys Pro
145                 150                 155                 160

Leu Ala Val Ile Gly Gly Asp Ser Ala Met Glu Glu Ala Asn Phe
                165                 170                 175

Leu Thr Tyr Gly Ser Lys Val Tyr Ile Ile Asp Arg Arg Asp Ala
            180                 185                 190

Phe Arg Ala Ser Lys Ile Met Gln Gln Arg Ala Leu Ser Asn Pro Lys
        195                 200                 205

Ile Asp Val Ile Trp Asn Ser Ser Val Val Glu Ala Tyr Gly Asp Gly
    210                 215                 220
```

```
Glu Arg Asp Val Leu Gly Gly Leu Lys Val Lys Asn Val Val Thr Gly
225                 230                 235                 240

Asp Val Ser Asp Leu Lys Val Ser Gly Leu Phe Phe Ala Ile Gly His
            245                 250                 255

Glu Pro Ala Thr Lys Phe Leu Asp Gly Gly Val Glu Leu Asp Ser Asp
            260                 265                 270

Gly Tyr Val Val Thr Lys Pro Gly Thr Thr Gln Thr Ser Val Pro Gly
            275                 280                 285

Val Phe Ala Ala Gly Asp Val Gln Asp Lys Lys Tyr Arg Gln Ala Ile
        290                 295                 300

Thr Ala Ala Gly Thr Gly Cys Met Ala Ala Leu Asp Ala Glu His Tyr
305                 310                 315                 320

Leu Gln Glu Ile Gly Ser Gln Gln Gly Lys Ser Asp
                325                 330

<210> SEQ ID NO 25
<211> LENGTH: 321
<212> TYPE: PRT
<213> ORGANISM: Escherichia coli

<400> SEQUENCE: 25

Met Gly Thr Thr Lys His Ser Lys Leu Leu Ile Leu Gly Ser Gly Pro
1               5                   10                  15

Ala Gly Tyr Thr Ala Ala Val Tyr Ala Ala Arg Ala Asn Leu Gln Pro
            20                  25                  30

Val Leu Ile Thr Gly Met Glu Lys Gly Gly Gln Leu Thr Thr Thr Thr
        35                  40                  45

Glu Val Glu Asn Trp Pro Gly Asp Pro Asn Asp Leu Thr Gly Pro Leu
    50                  55                  60

Leu Met Glu Arg Met His Glu His Ala Thr Lys Phe Glu Thr Glu Ile
65                  70                  75                  80

Ile Phe Asp His Ile Asn Lys Val Asp Leu Gln Asn Arg Pro Phe Arg
                85                  90                  95

Leu Asn Gly Asp Asn Gly Glu Tyr Thr Cys Asp Ala Leu Ile Ile Ala
            100                 105                 110

Thr Gly Ala Ser Ala Arg Tyr Leu Gly Leu Pro Ser Glu Glu Ala Phe
        115                 120                 125

Lys Gly Arg Gly Val Ser Ala Cys Ala Thr Cys Asp Gly Phe Phe Tyr
130                 135                 140

Arg Asn Gln Lys Val Ala Val Ile Gly Gly Asn Thr Ala Val Glu
145                 150                 155                 160

Glu Ala Leu Tyr Leu Ser Asn Ile Ala Ser Glu Val His Leu Ile His
            165                 170                 175

Arg Arg Asp Gly Phe Arg Ala Glu Lys Ile Leu Ile Lys Arg Leu Met
            180                 185                 190

Asp Lys Val Glu Asn Gly Asn Ile Ile Leu His Thr Asn Arg Thr Leu
        195                 200                 205

Glu Glu Val Thr Gly Asp Gln Met Gly Val Thr Gly Val Arg Leu Arg
    210                 215                 220

Asp Thr Gln Asn Ser Asp Asn Ile Glu Ser Leu Asp Val Ala Gly Leu
225                 230                 235                 240

Phe Val Ala Ile Gly His Ser Pro Asn Thr Ala Ile Phe Glu Gly Gln
                245                 250                 255

Leu Glu Leu Glu Asn Gly Tyr Ile Lys Val Gln Ser Gly Ile His Gly
```

```
                    260                 265                 270
Asn Ala Thr Gln Thr Ser Ile Pro Gly Val Phe Ala Ala Gly Asp Val
            275                 280                 285
Met Asp His Ile Tyr Arg Gln Ala Ile Thr Ser Ala Gly Thr Gly Cys
    290                 295                 300
Met Ala Ala Leu Asp Ala Glu Arg Tyr Leu Asp Gly Leu Ala Asp Ala
305                 310                 315                 320
Lys
```

<210> SEQ ID NO 26
<211> LENGTH: 998
<212> TYPE: DNA
<213> ORGANISM: Arabidopsis thaliana

<400> SEQUENCE: 26

| | | | | | |
|---|---|---|---|---|---|
| atgaatggtc | tcgaaactca | aacacaagg | ctctgtatcg | taggaagtgg | cccagcggca | 60 |
| cacacggcgg | cgatttacgc | agctagggct | gaacttaaac | ctcttctctt | cgaaggatgg | 120 |
| atggctaacg | acatcgctcc | cggtggtcaa | ctcaaccaac | caccgcgtga | aatttcccc | 180 |
| ggatttccag | aaggtattct | cggagtagag | ctcactgaca | aattccgtaa | caatcggag | 240 |
| cgattcggta | ctacgatatt | tacagagacg | gtgacgaaag | tcgatttctc | ttcgaaaccg | 300 |
| tttaagctat | tcacagattc | aaaagccatt | ctcgctgacg | ctgtgattct | cgctatcgga | 360 |
| gctgtggcta | agtggcttag | cttcgttgga | tctggtgaag | ttctcggagg | tttgtggaac | 420 |
| cgtggaatct | ccgcttgtgc | tgtttgcgac | ggagctgctc | cgatattccg | caacaaacct | 480 |
| cttgcggtga | tcgtggagg | cgattctgca | atggaagaag | caaactttct | tacaaaatat | 540 |
| ggatctaaag | tgtatataat | cgataggaga | gatgctttta | gagcgtctaa | gattatgcag | 600 |
| cagcgacttt | gtctaatcct | aagattgatg | tgatttggaa | ctcgtctgtt | gtggaagctt | 660 |
| atggagatgg | agaaagagat | gtgcttggag | gattgaaagt | gaagaatgtg | gttaccggag | 720 |
| atgtttctga | tttaaaagtt | tctggattgt | tctttgctat | tggtcatgag | ccagctacca | 780 |
| agttttttgga | tggtggtgtt | gagttagatt | cggatggtta | tgttgtcacg | aagcctggta | 840 |
| ctacacagac | tagcgttccc | ggagttttcg | ctgcgggtga | tgttcaggat | aagaagtata | 900 |
| ggcaagccat | cactgctgca | ggaactgggt | gcatggcagc | tttggatgca | gagcattact | 960 |
| tacaagagat | tggatctcag | caaggtaaga | gtgattga | | | 998 |

<210> SEQ ID NO 27
<211> LENGTH: 966
<212> TYPE: DNA
<213> ORGANISM: Escherichia coli

<400> SEQUENCE: 27

| | | | | | |
|---|---|---|---|---|---|
| atgggcacga | ccaaacacag | taaactgctt | atcctgggtt | caggcccggc | gggatacacc | 60 |
| gctgctgtct | acgcggcgcg | cgccaacctg | caacctgtgc | tgattaccgg | catggaaaaa | 120 |
| ggcggccaac | tgaccaccac | cacggaagtg | gaaaactggc | ctggcgatcc | aaacgatctg | 180 |
| accggtccgt | tattaatgga | gcgcatgcac | gaacatgcca | ccaagtttga | actgagatc | 240 |
| atttttgatc | atatcaacaa | ggtggatctg | caaaaccgtc | cgttccgtct | gaatggcgat | 300 |
| aacggcgaat | acacttgcga | cgcgctgatt | attgccaccg | gagcttctgc | acgctatctc | 360 |
| ggcctgccct | ctgaagaagc | ctttaaaggc | cgtgggtttt | ctgcttgtgc | aacctgcgac | 420 |
| ggtttcttct | atcgcaacca | gaaagttgcg | gtcatcggcg | gcggcaatac | cgcggttgaa | 480 |

-continued

```
gaggcgctgt atctgtctaa catcgcttcg gaagtgcatc tgattcaccg ccgtgacggt    540
ttccgcgcgg aaaaaatcct cattaagcgc ctgatggata aagtggagaa cggcaacatc    600
attctgcaca ccaaccgtac gctggaagaa gtgaccggcg atcaaatggg tgtcactggc    660
gttcgtctgc gcgatacgca aaacagcgat aacatcgagt cactcgacgt tgccggtctg    720
tttgttgcta tcggtcacag cccgaatact gcgattttcg aagggcagct ggaactggaa    780
aacggctaca tcaaagtaca gtcgggtatt catggtaatg ccacccagac cagcattcct    840
ggcgtctttg ccgcaggcga cgtgatggat cacatttatc gccaggccat tacttcgggc    900
ggtacaggct gcatggcagc acttgatgcg gaacgctacc tcgatggttt agctgacgca    960
aaataa                                                                966
```

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
atatctagaa tggcggcgtc ggcggcga                                        28

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
atagagctct tactgggccg cgtgtag                                         27

<210> SEQ ID NO 30
<211> LENGTH: 36
<212> TYPE: DNA
<213> ORGANISM: Artificial Sequence
<220> FEATURE:
<223> OTHER INFORMATION: primer

<400> SEQUENCE: 30
ggcgcatgcg aattcgaatt cgatatcgat cttcga                               36

<210> SEQ ID NO 31
<211> LENGTH: 27
<212> TYPE: DNA
<213> ORGANISM: Artificial Sequence
<220> FEATURE:
<223> OTHER INFORMATION: primer

<400> SEQUENCE: 31
aactctagac tcggtggact gtcaatg                                         27

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
ccaagaagtt cccagctgc                                                  19

-continued

```
<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
atagctgcga caaccctgtc ctt                                              23

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
catcgagaca agcacggtca acttc                                            25

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
atatccgagc gcctcgtgca tgcg                                             24

<210> SEQ ID NO 36
<211> LENGTH: 27
<212> TYPE: PRT
<213> ORGANISM: rat

<400> SEQUENCE: 36
```

Tyr Met Thr Val Ser Ile Ile Asp Arg Phe Met Gln Asp Ser Cys Val
 1               5                  10                  15

Pro Lys Lys Met Leu Gln Leu Val Gly Val Thr
            20                  25

```
<210> SEQ ID NO 37
<211> LENGTH: 28
<212> TYPE: PRT
<213> ORGANISM: mouse

<400> SEQUENCE: 37
```

Lys Phe Arg Leu Leu Gln Glu Thr Met Tyr Met Thr Val Ser Ile Ile
 1               5                  10                  15

Asp Arg Phe Met Gln Asn Ser Cys Val Pro Lys Lys
            20                  25

```
<210> SEQ ID NO 38
<211> LENGTH: 27
<212> TYPE: PRT
<213> ORGANISM: mouse

<400> SEQUENCE: 38
```

Arg Ala Ile Leu Ile Asp Trp Leu Ile Gln Val Gln Met Lys Phe Arg
 1               5                  10                  15

Leu Leu Gln Glu Thr Met Tyr Met Thr Val Ser
            20                  25

```
<210> SEQ ID NO 39
```

-continued

```
<211> LENGTH: 27
<212> TYPE: PRT
<213> ORGANISM: mouse

<400> SEQUENCE: 39

Asp Arg Phe Leu Gln Ala Gln Leu Val Cys Arg Lys Lys Leu Gln Val
1               5                   10                  15

Val Gly Ile Thr Ala Leu Leu Leu Ala Ser Lys
            20                  25

<210> SEQ ID NO 40
<211> LENGTH: 18
<212> TYPE: PRT
<213> ORGANISM: mouse

<400> SEQUENCE: 40

Met Ser Val Leu Arg Gly Lys Leu Gln Leu Val Gly Thr Ala Ala Met
1               5                   10                  15

Leu Leu

<210> SEQ ID NO 41
<211> LENGTH: 26
<212> TYPE: DNA
<213> ORGANISM: Artificial Sequence
<220> FEATURE:
<223> OTHER INFORMATION: primer

<400> SEQUENCE: 41
gtaaagcttt aacaacccac acattg                                    26

<210> SEQ ID NO 42
<211> LENGTH: 42
<212> TYPE: DNA
<213> ORGANISM: Artificial Sequence
<220> FEATURE:
<223> OTHER INFORMATION: primer

<400> SEQUENCE: 42
cgccgttgcc gacgccgctg caatcgtact tgttgccgca at                  42

<210> SEQ ID NO 43
<211> LENGTH: 32
<212> TYPE: DNA
<213> ORGANISM: Artificial Sequence
<220> FEATURE:
<223> OTHER INFORMATION: primer

<400> SEQUENCE: 43
acaagtacga ttgcagcggc gtcggcaacg gc                             32

<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
atagagctct tactgggccg ccgcgtg                                   27

<210> SEQ ID NO 45
<211> LENGTH: 19
<212> TYPE: DNA
<213> ORGANISM: Artificial Sequence
<220> FEATURE:
```

<223> OTHER INFORMATION: primer

<400> SEQUENCE: 45
ccaagaagtt cccaaatgc                                                19

<210> SEQ ID NO 46
<211> LENGTH: 35
<212> TYPE: DNA
<213> ORGANISM: Artificial Sequence
<220> FEATURE:
<223> OTHER INFORMATION: primer

<400> SEQUENCE: 46
attctagaat ggagggatcc gccgcggcgc cgctc                              35

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
ttggtacctc aatcagactt gcccacctgt                                    30

<210> SEQ ID NO 48
<211> LENGTH: 9
<212> TYPE: PRT
<213> ORGANISM: Artificial Sequence
<220> FEATURE:
<223> OTHER INFORMATION: cyclin A destruction box

<400> SEQUENCE: 48

Arg Thr Val Leu Gly Val Ile Gly Asp
 1               5

<210> SEQ ID NO 49
<211> LENGTH: 19
<212> TYPE: DNA
<213> ORGANISM: Artificial Sequence
<220> FEATURE:
<223> OTHER INFORMATION: primer

<400> SEQUENCE: 49
ccaagaagtt cccagcgtc                                                19

<210> SEQ ID NO 50
<211> LENGTH: 18
<212> TYPE: DNA
<213> ORGANISM: Artificial Sequence
<220> FEATURE:
<223> OTHER INFORMATION: primer

<400> SEQUENCE: 50
cacgcggcgg cccagtaa                                                 18

<210> SEQ ID NO 51
<211> LENGTH: 9
<212> TYPE: PRT

-continued

```
<213> ORGANISM: Artificial Sequence
<220> FEATURE:
<223> OTHER INFORMATION: cyclin B1 destruction box

<400> SEQUENCE: 51

Arg Thr Ala Leu Gly Asp Ile Gly Asn
 1               5
```

BARLEY GENE FOR THIOREDOXIN AND NADP-THIOREDOXIN REDUCTASE

This application claims the benefit of the filing date of application Ser. No. 60/127,198, filed Mar. 31, 1999 pending, application Ser. No. 60/169,162, filed Dec. 6, 1999, pending; application Ser. No. 60/177,740 filed Jan. 21, 2000, pending; and application Ser. No. 60/177,739, filed Jan. 21, 2000, pending, all of which are expressly incorporated by reference in their entirety.

ACKNOWLEDGMENT OF GOVERNMENT SUPPORT

This invention was made with Government support under Grant 9803835 from the U.S. Department of Agriculture. The Government has certain rights to this invention.

BACKGROUND OF THE INVENTION

Thioredoxins are small (about 12 kDa) thermostable proteins with catalytically active disulfide groups. This class of proteins has been found in virtually all organisms, and has been implicated in myriad biochemical pathways (Buchanan et al., 1994). The active site of thioredoxin has two redox-active cysteine residues in a highly conserved amino acid sequence; when oxidized, these cysteines form a disulfide bridge (—S—S—) that can be reduced to the sulfhydryl (—SH) level through a variety of specific reactions. In physiological systems, this reduction may be accomplished by reduced ferredoxin, NADPH, or other associated thioredoxin-reducing agents. The reduced form of thioredoxin is an excellent catalyst for the reduction of even the most intractable disulfide bonds.

Generally only one kind of thioredoxin is found in bacterial or animal cells. In contrast, photosynthetic organisms have three distinct types of thioredoxin. Chloroplasts contain a ferredoxin/thioredoxin system comprised of ferredoxin, ferredoxin-thioredoxin reductase and thioredoxins f and m, which function in the light regulation of photosynthetic enzymes (Buchanan, 1991; Scheibe, 1991; Vogt et al, 1986). The other thioredoxin enzyme system is analogous to that established for animals and most microorganisms, in which thioredoxin (h-type in plants) is reduced by NADPH and NADPH-thioredoxin reductase (NTR) (Johnson et al., 1987a; Florencio et al., 1988; Suske et al., 1979). The reduction of thioredoxin h by this system can be illustrated by the following equation:

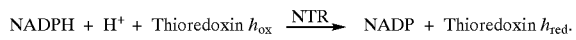

Some plant species contain a family of closely related thioredoxin h proteins, which probably perform different physiological functions. Specific plants in which multiple thioredoxin h proteins have been found include spinach (Florencio et al., 1988), wheat (Johnson et a., 1987), rice (Ishiwatari et al., 1995), and Arabidopsis (Rivera-Madrid et al., 1995). The type-h thioredoxin was discovered considerably after the discovery of the m and f types, and because of this much less is known about this cytosolic thioredoxin and its physiological functions. Considerable work is currently directed toward studying thioredoxin h proteins (Besse and Buchanan, 1997).

Thioredoxin h is widely distributed in plant tissues and exists in mitochondria, endoplasmic reticulum (ER) and the cytosol (Bodenstein-Lang et al., 1989; Marcus et al., 1991; Vogt et al. 1986). Plant thioredoxin h is involved in a wide variety of biological functions. Thioredoxin h functions in the reduction of intramolecular disulfide bridges of a variety of low molecular-weight, cystine-rich proteins, including thionins (Johnson et al., 1987b), protease inhibitors and chloroform/methanol-soluble proteins (CM proteins) (Kobrehel et al, 1991). It is likely that cytoplasmic thioredoxins participate in developmental processes: for example thioredoxin h has been shown to function as a signal to enhance metabolic processes during germination and seedling development (Kobrehel et al., 1992; Lozano et al., 1996; Besse et al., 1996). Thioredoxin h has also been demonstrated to be involved in self-incompatibility in *Phalaris coerulescens* (Li et al., 1995) and *Brassica napus* (Bower et al., 1996). Several functions have been hypothesized for rice thioredoxin h, which is believed to be involved in translocation in sieve tubes (Ishiwatari et al., 1995).

Uses of thioredoxin include incorporation into hair care products (U.S. Pat. No. 4,935,231) and neutralization of certain venoms and toxins (see U.S. Pat. No. 5,792,506). Recent research into thioredoxin activity has also focused on harnessing the reducing power of this protein for food technology. For example, U.S. Pat. No. 5,792,506 to Buchanan (Neutralization of Food Allergens by Thioredoxin), and Buchanan et al. (1998) describe the use of thioredoxin to reduce the allergenicity of foods through thioredoxin-mediated reduction of intramolecular disulfide bonds found in various allergenic food proteins (e.g., in milk, soya and wheat proteins) (Buchanan et al, 1997; del Val et al., 1999). In addition, it has been shown that reduction of disulfide protein allergens in wheat and milk by thioredoxin decreases their allergenicity (Buchanan et al., 1997; del Val et al., 1999). Thioredoxin treatment also increases the digestibility of the major allergen of milk (β-lactoglobulin) (del Val et al., 1999), as well as other disulfide proteins (Lozano et al., 1994; Jiao et al., 1992).

Thioredoxin h has been shown to be useful as a food additive to enhance the baking qualities of cereal flour (Bright et al., 1983). For example, improvement in dough strength and bread quality properties of poor-quality wheat flour results from the addition of thioredoxin (Wong et al., 1993; Kobrehel et al., 1994). This has been attributable to the thioredoxin-catalyzed reduction of intramolecular disulfide bonds in the flour proteins, specifically the glutenins, resulting in the formation of new intermolecular disulfide bonds (Besse and Buchanan, 1997). Thus, the addition of exogenous thioredoxin promotes the formation of a protein network that produces flour with enhanced baking quality. Kobrehel et at, (1994) have observed that the addition of thioredoxin h to flour of non-glutenous cereals such as rice, maize and sorghum promotes the formation of a dough-like product. Hence, the addition of exogenous thioredoxin may be used to produce baking dough from non-glutenous cereals.

cDNA clones encoding thioredoxin h have been isolated from a number of plant species, including Arabidopsis thaliana(Rivera-Madrid et al., 1993; Rivera-Madrid et al., 1995), *Nicotiana tabacum* (Marty and Meyer, 1991; Brugidou et al., 1993), *Oryza sativa* (Ishiwatari et al., 1995), *Brassica napus* (Bower et al, 1996), *Glycine max* (Shi and Bhattacharyya, 1996), and *Triticum aestivum* (Gautier et al., 1998).

Thioredoxin and NTR were first characterized in *Escherichia coli* as the hydrogen donor system for ribonucleotide reductase (Laurent et al., 1964 Moore et al., 1964) The *E. coli* NTR gene has been isolated (Russel and Model, 1988)

and the three-dimensional structure of the protein has been analyzed (Kuriyan et al., 1991). Some other NTR genes have been isolated and sequenced from bacteria, fungi and mammals. Recently, Jacquot et al. (1994) have reported a successful isolation and sequencing of two cDNAs encoding the plant *Arabidopsis thaliana* NTRs. The subsequent expression of the recombinant *A. thaliana* NTR protein in *E. coli* cells (Jacquot et al., 1994) and its first eukaryotic structure (Dai et al., 1996) have also been reported.

Thioredoxin and NTR were first characterized in *Escherichia coli* as the hydrogen donor system for ribonucleotide reductase (Laurent et al, 1964; Moore et al., 1964) The *E. coli* NTR gene has been isolated (Russel and Model, 1988) and the three-dimensional structure of the protein has been analyzed (Kuniyan et al., 1991). Some other NTR genes have been isolated and sequenced from bacteria, fungi, and mammals. Recently, Jacquot et al. (1994) have reported a successful isolation and sequencing of two cDNAs encoding the plant *Arabidopsis thaliana* NTRs. The subsequent expression of the recombinant *A. thaliana* NTR protein in *E. coli* cells (Jacquot et al., 1994) and its first eukaryotic structure (Dai et al., 1996) have also been reported.

Here we report isolated nucleic acids encoding the barley genes for thioredoxin h and NADP-thioredoxin reductase; isolated barley thioredoxin h and NADP-thioredoxin reductase proteins, and methods of use.

SUMMARY OF THE INVENTION

The invention provides isolated nucleic acids encoding barley thioredoxin and NADP-thioredoxin reductase proteins and methods of use.

In other aspect the invention provides expression vectors comprising nucleic acids encoding barley thioredoxin and NADP-thioredoxin and transformed host cells. Accordingly, the invention provides methods of expressing an isolated barley thioredoxin and NADP-thioredoxin reductase polypeptides.

In a further aspect the invention provides transgenic plants comprising the expression vectors. In a preferred embodiment, the transgenic plants overexpress barley thioredoxin and NADP-thioredoxin reductase polypeptides. The polypeptides of the invention, expressed in a transgenic plant either alone or in combination alters the redox status of a plant in comparison to a nontransgenic plant of the same species. In a preferred embodiment, the expressed polypeptide transgene alters the redox status of a seed or grain, thereby altering the biochemical and biological properties of a seed or grain. The seed or grain provides advantages in increased germination efficiency, decreased allergenicity, increased protein solubility, increased digestibility.

In another aspect, the invention provides methods of expressing a barley thioredoxin or NADP-thioredoxin reductase polypeptides.

In yet another aspect, the invention provides of expressing a barley thioredoxin or NADP-thioredoxin reductase polypeptide. Accordingly, the invention provides isolated barley thioredoxin or NADP-thioredoxin reductase polypeptides.

In still yet another aspect the invention provides methods of identifying a bioactive agent that binds and preferably reduces a biological activity of a barley thioredoxin or NADP-thioredoxin reductase polypeptide.

BRIEF DESCRIPTION OF THE DRAWINGS

FIGS. 4A–C shows the deduced amino acid sequence of *H. vulgare* NADP-thioredoxin reductase (NTR) and homologies. Panel A shows the amino acid sequence alignment of *H. vulgare* NADP-thioredoxin reductase (NTR) and the NTR sequences of *A. thaliana* and *E. coli*. Amino acid identities are shown by shaded residues. Panel B shows the percent similarity and percent divergence between amino acid sequences of *H. vulgare* NTR and the NTR sequences of *A. thaliana* and *E. coli*. Panel C shows the phylogenetic tree (in relative units) of *H. vulgare* NTR and related sequences from *A. thaliana* and *E. coli*.

FIG. 5A–D shows the nucleotide sequence of *H. vulgare* NADP-thioredoxin reductase (NTR) gene (SEQ ID NO:10) and homologies. Panel A shows the nucleotide sequence alignment of *H. vulgare* NTR gene and the NTR sequences of *A. thaliana* (SEQ ID NO:26) and *E. coli* (SEQ ID NO:27). Nucleotides conserved in at least two out of three different NTR genes are shaded. Panel B shows the nucleotide sequence alignment of H. vulgareNTR gene and the NTR sequences of *A. thaliana* and *E. coli*. Nucleotides conserved nucleotides the three different NTR genes are shaded. Panel C shows the percent homology and percent divergence between nucleotide sequences of *H. vulgare* NTR and the NTR sequences of *A. thaliana* and *E. coli*. Panel D shows that the phylogenetic tree (in relative units) of *H. vulgare* NTR and related nucleotide sequences from *A. thaliana* and *E. coli*.

FIG. 7 shows the thioredoxin activity profile of various barley grains transformed with wheat thioredoxin gene (wtrxh).

FIG. 11 shows the nucleic acid sequence of the $B_1$-hordein promoter (SEQ ID NO:11) and the 57 base pair $B_1$-hordein signal sequence (underlined).

FIG. 12 shows the nucleic acid sequence of the D-hordein promoter (SEQ ID NO:12) and the 63 base pair D-hordein signal sequence (underlined).

FIG. 13A–C shows the effect of overexpressed thioredoxin h on pullulanase activity in transgenic barley grain during germination and seedling development. A homozygous line, GPdBhssBarWtrx-29-3, and a null segregant, GPdBhssBarWtrx-29-11-10, were used for the pullulanase assays. Panel A: Pullulanase was assayed spectrophotometrically by measuring the dye released from red pullulan substrate at 534 nm. Panel B: Pullulanase was separated on native 7.5% polyacrylamide gels containing the red pullulan substrate. Activity, identified by comparison with purified barley pullulanase, is seen as clear areas that developed on incubating the gel in 0.2 M succinate buffer, pH 6.0, for 1 hr at 37° C. Panel C: The gel in Panel B was scanned and analyzed by integration of the activity bands.

SEQUENCE LISTING

Figure 1:
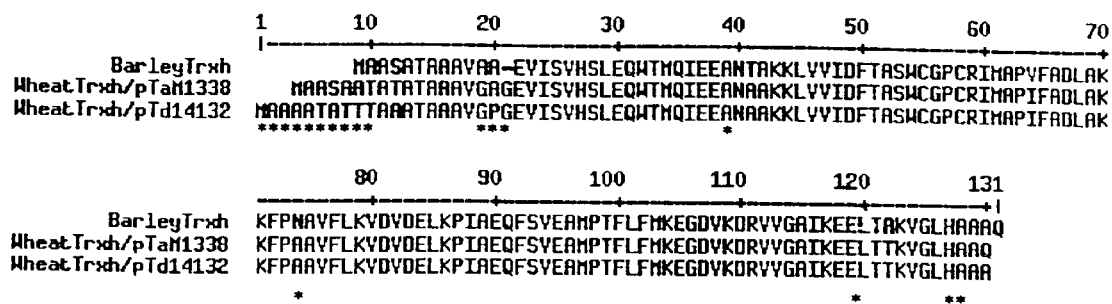
FIG. 1 shows a comparison of the amino acid sequences of barley thioredoxin h and two wheat thioredoxin h proteins.

The nucleic and amino acid sequences listed in the accompanying sequence listing (SEQ ID NO:1–24) are shown using standard letter abbreviations for nucleotide bases, and three letter code for amino acids. Only one strand of each nucleic acid sequence is shown, but it is understood that the complementary strand is included by any reference to the displayed strand.

SEQ ID NO:1 shows the nucleic acid sequence of the barley thioredoxin h cDNA.

SEQ ID NO:2 shows the amino acid sequence of the barley thioredoxin h protein.

SEQ ID NO:3 shows the nucleic acid sequence of a wheat thioredoxin h cDNA, GenBank accession number X699 15.

SEQ ID NO:4 shows the amino acid sequence of a wheat thioredoxin h protein.

SEQ ID NO:5 shows the nucleic acid sequence of a wheat thioredoxin h cDNA, GenBank accession number AJ00 1903.

SEQ ID NO:6 shows the amino acid sequence of a wheat thioredoxin h protein.

SEQ ID NO:111 shows the nucleic acid sequence of the barley $B_1$-hordein promoter and signal sequence.

SEQ ID NO:12 shows the nucleic acid sequence of the barley D-hordein promoter and signal sequence.

Other SEQ ID NOs: are described herein.

DETAILED DESCRIPTION OF THE INVENTION

I. Definitions

Unless otherwise noted, technical terms are used according to conventional usage. Definitions of common terms in molecular biology may be found in Lewin, Genes V published by Oxford University Press, 1994 (ISBN 0-19-854287-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology. a Comprehensive Desk Reference, published by VCH Publishers, Inc., 1995 (ISBN 1-56081-569-8); Ausubel et al. (1987) Current Protocols in Molecular Biology, Green Publishing; Sambrook et a/ (1989) Molecular Cloning: A Laboratory Manual, Cold Spring Harbor, N.Y.).

In order to facilitate review of the various embodiments of the invention, the following definitions are provided:

Thioredoxin protein: A large number of plant, animal, and microbial thioredoxin proteins have been characterized, and the genes encoding many of these proteins have been cloned and sequenced. The present invention is preferably directed to the use of thioredoxin h proteins, although other thioredoxin proteins may also be employed to produce transgenic plants as described herein. Among the thioredoxin h proteins from plants that have been described to date are thioredoxin h proteins from *Arabidopsis thaliana* (Rivera-Madrid et al., 1993; Rivera-Madrid et a., 1995), *Nicotiana tabacum* (Marty and Meyer, 1991; Brugidou et a., 1993), *Oryza sativa* (Ishiwatari et a., 1995), *Brassica napus* (Bower et al., 1996), *Glycine max* (Shi and Bhattacharyya, 1996), and *Triticum aestivum* (Gautier et al., 1998). The amino acid sequences of these and other thioredoxin h proteins, and the nucleotide sequence of cDNAs and/or genes that encode these proteins, are available in the scientific literature and publicly accessible sequence databases. For example, a cDNA encoding thioredoxin h from *Picea mariana* is described in accession number AF051206 (NID g2982246) of GenBank, and located by a search using the Entrez browser/nucleotide sequence search of the National Center for Biotechnology Information website, www.ncbi.nlm.nih.gov. The cDNA encoding the *Triticum aestivum* thioredoxin h protein used in the Examples described below is described on the same database under accession number X69915 (NID g2995377).

The present invention may be practiced using nucleic acid sequences that encode full length thioredoxin h proteins, as well as thioredoxin h derived proteins that retain thioredoxin h activity. Thioredoxin h derived proteins which retain thioredoxin biological activity include fragments of thioredoxin h, generated either by chemical (e.g. enzymatic) digestion or genetic engineering means; chemically functionalized protein-molecules obtained starting with the exemplified protein or nucleic acid sequences, and protein sequence variants. Thus, the term "thioredoxin h protein" encompasses full length thioredoxin h proteins, as well as such thioredoxin h derived proteins that retain thioredoxin h activity.

Thioredoxin protein may be quantified in biological samples (such as seeds) either in terms of protein level, or in terms of thioredoxin activity. Thioredoxin protein level may be determined using a western blot analysis followed by quantitative scanning of the image as described in detail below. Thioredoxin activity may be quantified using a number of different methods known in the art. Preferred methods of measuring thioredoxin biological activity attributable to thioredoxin h in plant extracts include NADP/malate dehydrogenase activation (Johnson et al., 1987a,b) and reduction of 2',5'-dithiobis(2-nitrobenzoic acid) (DTNB) via NADP-thioredoxin reductase (Florencio et al., 1988; U.S. Pat. No. 5,792,506). Due to the potential for interference from non-thioredoxin h enzymes that use NADPH, accurate determination of thioredoxin h activity should preferably be made using partially purified plant extracts. Standard protein purification methods (e.g. $(NH_4)_2SO_4$ extraction) can be used to accomplish this partial purification. The activity of thioredoxin h may also be expressed in terms of specific activity, i.e., thioredoxin activity per unit of protein present, as described in more detail below.

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (1989) and Ausubel et al. (1987).

Primers are short nucleic acids, preferably DNA oligonucleotides about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g, by the polymerase chain reaction (PCR) or other nucleic-acid amplification methods known in the art.

Methods for preparing and using probes and primers are described, for example, in Sambrook et al. (1989), Ausubel et al. (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of the barley thioredoxin h cDNA will anneal to a target sequence such as a thioredoxin h homologue from a different barley cultivar contained within a cDNA or genomic DNA library with a higher specificity than a corresponding primer of only 15 nucleotides. Thus, in order to obtain greater specificity, probes and primers may be selected that comprise 20, 25, 30, 35, 40, 50 or more consecutive nucleotides of the barley thioredoxin h cDNA or gene sequences.

Accordingly, oligonucleotides that are derived from the barley thioredoxin h and NTR nucleic acids are encompassed within the scope of the present invention. Preferably, such oligonucleotide primers will comprise a sequence of at least 15–20 consecutive nucleotides of the barley thioredoxin h encoding sequences.

Promoter: A regulatory nucleic acid sequence, typically located upstream (5') of a gene that, in conjunction with various cellular proteins, is responsible for regulating the expression of the gene. Promoters may regulate gene expression in a number of ways. For example, the expression may be tissue-specific, meaning that the gene is expressed at enhanced levels in certain tissues, or developmentally regulated, such that the gene is expressed at enhanced levels at certain times during development, or both.

In a preferred embodiment, a-transgene of the invention is expressed in an edible part of a plant. By "edible" herein is meant at least a part of a plant that is suitable for consumption by humans or animals (fish, crustaceans, isopods, decapods, monkeys, cows, goats, pigs, rabbits, horses, birds (chickens, parrots etc). Accordingly, "edible" embraces food for human consumption and feed for animal consumption and includes, for example, dough, bread, cookies, pasta, pastry, beverages, beer, food additives, thickeners, malt, extracts made from an edible part of plants, animals feeds, and the like. An edible part of a plant includes for example, a root, a tuber, a seed, grain, a flower, fruit, leaf etc. The skilled artisan is aware that expression of the transgene is effected in any tissue, organ or part of a plant by employing a promoter that is active in the selected part of the plant the transgene is to be expressed. In a preferred embodiment the transgene is expressed in a seed, preferably under control of a seed- or grain-specific promoter.

The expression of a transgene in seeds or grains according to the present invention is preferably accomplished by operably linking a seed-specific or grain-specific promoter to the nucleic acid molecule encoding the transgene protein. In this context, "seed-specific" indicates that the promoter has enhanced activity in seeds compared to other plant tissues; it does not require that the promoter is solely active in the seeds. Accordingly, "grain-specific" indicates that the promoter has enhanced activity in grains compared to other plant tissues; it does not require that the promoter is solely active in the grain. Preferably, the seed- or grain-specific promoter selected will, at the time when the promoter is most active in seeds, produce expression of a protein in the seed of a plant that is at least about two-fold greater than expression of the protein produced by that same promoter in the leaves or roots of the plant. However, given the nature of the thioredoxin protein, it may be advantageous to select a seed- or grain-specific promoter that causes little or no protein expression in tissues other than seed or grain. In a preferred embodiment, a promoter is specific for seed and grain expression, such that, expression in the seed and grain is enhanced as compared to other plant tissues but does not require that the promoter be solely activity in the grain and seed. In a preferred embodiment, the promoter is "specific" for a structure or element of a seed or grain, such as an embryo-specific promoter. In accordance with the definitions provided above, an embryo-specific promoter has enhanced activity in an embryo as compared to other parts of a seed or grain or a plant and does not require its activity to be limited to an embryo. In a preferred embodiment, the promoter is "maturation-specific" and accordingly has enhanced activity developmentally during the maturation of a part of a plant as compared to other parts of a plant and does not require its activity to be limited to the development of a part of a plant.

A seed- or grain-specific promoter may produce expression in various tissues of the seed, including the endosperm, embryo, and aleurone or grain. Any seed- or grain-specific promoter may be used for this purpose, although it will be advantageous to select a seed- or grain-specific promoter that produces high level expression of the protein in the plant seed or grain. Known seed- or grain-specific promoters include those associated with genes that encode plant seed storage proteins such as genes encoding: barley hordeins, rice glutelins, oryzins, or prolamines; wheat gliadins or gluterins; maize zeins or glutelins; maize embryo-specific promoter; oat glutelins; sorghum kafirins; millet pennisetins; or rye secalins.

The barley hordein promoters (described in more detail below) are seed- or grain-specific promoters that were used in the illustrative Examples (Cameron-Mills, 1980; Cameron-Mills et al., 1980, 1988a,b).

In certain embodiments, the seed- or grain-specific promoter that is selected is a maturation-specific promoter. The use of promoters that confer enhanced expression during seed or grain maturation (such as the barley hordein promoters) may result in even higher levels of thioredoxin expression in the seed.

By "seed or grain-maturation" herein refers to the period starting with fertilization in which metabolizable food reserves (e.g., proteins, lipids, starch, etc.) are deposited in the developing seed, particularly in storage organs of the seed, including the endosperm, testa, aleurone layer, embryo, and scutellar epithelium, resulting in enlargement and filling of the seed and ending with seed desiccation.

Members of the grass family, which include the cereal grains, produce dry, one-seeded fruits. This type of fruit, is strictly speaking, a caryopsis but is commonly called a kernel or grain. The caryopsis of a fruit coat or pericarp, which surrounds the seed and adhere tightly to a seed coat. The seed consists of an embryo or germ and an endosperm enclosed by a nucellar epidermis and a seed coat. Accordingly the grain comprises the seed and its coat or pericarp. The seed comprises the embryo and the endosperm. (R. Carl Hoseney in "Principles of Cereal Science and Technology", expressly incorporated by reference in its entirety).

Starch: A polysaccharide made up of a chain of glucose units joined by alpha-1,4 linkages, either unbranched (amylose) or branched (amylopectin) at alpha-1,6-linkages.

Dextran: Any of a variety of storage polysaccharides, usually branched, made of glucose residues joined by alpha-1,6 linkages.

Dextrin or Limit Dextrin: Any of a group of small soluble polysaccharides, partial hydrolysis products of starch, usually enriched in alpha-1,6-linkages.

Germination: A resumption of growth of a plant embryo in favorable conditions after seed maturation and drying (dessication), and emergence of young shoot and root from the seed.

Allergen: An antigenic substance that induces an allergic reaction in a susceptible host. Accordingly, a susceptible host has an immune status (hypersensitivity) that results in an abnormal or harmful immune reaction upon exposure to an allergen. In a preferred embodiment, the transgenic grains of the invention have reduced allergenicity in comparison to nontransgenic grains. The immune reaction can be immediate or delayed; cell mediated or antibody mediated; or a combination thereof. In a preferred embodiment, the allergic reaction is an immediate type hypersensitivity.

Digestion: By "digestion" herein is meant the conversion of a molecule or compound to one or more of its components. Accordingly, "digestibility" relates to the rate and efficiency at which the conversion to one or more of its components occurs. In a preferred embodiment a "digestible compound" is, for example, a food, that is converted to its chemical components by chemical or enzymatic means. For example, dextran is converted to dextrin, polysaccharide, monosaccharides, limit dextrin etc; a protein is converted to a polypeptides, oligopeptides, amino acids, ammonia etc.; a nucleic acid is converted to oligonucleotides, nucleotides, nucleosides, purine, pyrimidines, phosphates etc. In a preferred embodiment, the transgenic grains of the invention have increased digestibility, i.e. are more efficiently or rapidly digested in comparison to nontransgenic grain.

Germination: A resumption of growth of a plant embryo in favorable conditions after seed or grain maturation and drying (dessication), and emergence of young shoot and root from the seed or grain.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by Agrobacterium, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated", as described above.

Complementary DNA (cDNA): A piece of DNA that is synthesized in the laboratory by reverse transcription of an RNA, preferably an RNA extracted from cells. cDNA produced from mRNA typically lacks internal, non-coding segments (introns) and regulatory sequences that determine transcription.

Open reading frame (ORF): A series of nucleotide triplets (codons) coding for amino acids without any internal termination codons. These sequences are usually translatable into a peptide.

Transgenic plant: As used herein, this term refers to a plant that contains recombinant or isolated genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant and parts of said plant, for instance grains, seeds, flowers, leaves, roots, fruit, pollen, stems etc.

The present invention is applicable to both dicotyledonous plants (e.g. tomato, potato, soybean, cotton, tobacco, etc.) and monocotyledonous plants, including, but not limited to graminaceous monocots such as wheat (Triticum spp.), rice (Oryza spp.), barley (Hordeum spp.), oat (Avena spp.), rye (Secale spp.), corn (Zea mays), sorghum (Sorghum spp.) and millet (Pennisetum spp). For example, the present invention can be employed with barley genotypes including, but not limited to Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

Purified: The term purified does not require absolute purity; rather, it is intended as a relative term. Thus, for example, a purified barley thioredoxin h protein preparation is one in which the barley thioredoxin h protein is more enriched or more biochemically active or more easily detected than the protein is in its natural environment within a cell or plant tissue. Accordingly, "purified" embraces or includes the removal or inactivation of an inhibitor of a molecule of interest. In a preferred embodiment, a preparation of barley thioredoxin h protein is purified such that the barley thioredoxin h represents at least 5–10% of the total protein content of the preparation. For particular applications, higher protein purity may be desired, such that preparations in which barley thioredoxin h represents at least 50% or at least 75% or at least 90% of the total protein content may be employed.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences.

II. Thioredoxin h (BTRXh) and NADP-thioredoxin Reductase (NTR) from Barley (*Hordeum vulgare* L.)

Herein are provided BTRXh and NTR proteins and nucleic acids which encode such proteins. Also provided are methods of screening for a bioactive agent capable of binding and preferably modulating the activity of the BTRXh or NTR protein. The method comprises combining a BTRXh or an NTR protein and a candidate bioactive agent and a cell or a population of cells, and determining the effect on the cell in the presence and absence of the candidate agent. Other screening assays including binding assays are also provided herein as described below.

NTR belongs to the pyridine nucleotide-disulfide oxidoreductase family (Pai, 1991), which includes glutathione reductase, lipoamide dehydrogenase, mercuric reductase and trypanothionine reductase, which catalyze the transfer of electrons from a pyridine nucleotide via a flavin carrier to, in most cases, disulfide-containing substrates. Preferably, NTR is barley *H. vulgare* NTR and is a flavoenzyme that reduces thioredoxin h using NADPH. We have found that barley NTR reduces wheat thioredoxin h (Cho et al. 1999 (PNAS)).

A barley thioredoxin protein is a barley protein having thioredoxin biological activity. Plant thioredoxins are generally categorized into three subgroups (m, f, and h) based on subcellular localization and specificity of enzyme activation. A barley thioredoxin h (BTRXh) protein is a barley protein having thioredoxin protein biological activity and sharing amino acid sequence identity and/or is encoded by a nucleic acid that hybridizes under high stringency conditions to the exemplified BTRXh nucleic acid as described below. Thioredoxin proteins typically contain a consensus active site—WCGPC (residues 45–49 of SEQ ID NO:2). Though it is not absolutely required, in general thioredoxin proteins can also be identified by the presence of this or a similar sequence.

A BTRXh and an NTR protein of the present invention also may be identified in alternative ways. "Protein" in this sense includes proteins, polypeptides, and peptides.

The BTRXh and NTR proteins of the invention fall into two general classes: proteins that are completely novel, i.e. are not part of a public database as of the time of discovery, although they may have homology to either known proteins or peptides encoded by expressed sequence tags (ESTs) and the like. Alternatively, the BTRXh and NTR proteins are known proteins, but that were not known to be, respectively, thioredoxins or oxidoreductases that preferably reduce thioredoxin h. Accordingly, a NTR protein may be initially identified by its association with a protein known to be involved in the reduction of thioredoxin. A BTRXh protein may be initially identified by its association with an NTR protein. Wherein the BTRXh and NTR proteins and nucleic acids are novel, compositions and methods of use are provided herein. In the case that the BTRXh and NTR proteins and nucleic acids were known but not known to be thioredoxins or oxidoreductases that preferably reduce thioredoxin h, methods of use, i.e. functional screens, are provided. In one embodiment, a BTRXh or an NTR protein as defined herein has at least one of the following "BTRXh biological activities or "NTR biological activities".

By "NTR biological activity" herein preferably is meant the catalytic reduction of thioredoxin coupled to $NADPH_2$ oxidation.

By "thioredoxin protein biological activity" herein is meant the ability of a protein to serve as a hydrogen donor in various reduction reactions (Smith et al. (eds.) 1997). One of ordinary skill in the art will be aware that there are many well-established systems that can be employed to measure thioredoxin mediated reduction reactions. Preferred methods of measuring biological thioredoxin activity attributable to thioredoxin h include NADP/malate dehydrogenase activation (Johnson et al., 1987) and reduction of 2',5'-dithiobis (2-nitrobenzoic acid) (DTNB) via NADP-thioredoxin reductase (Florencio et al., 1988; U.S. Pat. No. 5,792,506). Due to the potential for interference from non-thioredoxin h enzymes that use NADPH, accurate determination of thioredoxin h activity should be made using partially purified plant extracts. Standard protein purification methods (e.g $(NH_4)_2SO_4$ extraction and acid fractionation) can be used to accomplish this partial purification, as discussed more fully below.

In one embodiment provided herein, BTRXh and an NTR protein as defined herein have sequence homology to other thioredoxin and NTR proteins, respectively. By "homology" herein is meant sequence similarity and identity, with identity being preferred. In one embodiment, the homology is found using the following database, algorithm, and parameters.

The similarity between two nucleic acid sequences, or two amino acid sequences is expressed in terms of sequence identity (or, for proteins, also in terms of sequence similarity). Sequence identity is frequently measured in terms of percentage identity; the higher the percentage, the more similar the two sequences are. As described above, homologs and variants of the thioredoxin nucleic acid molecules, hordein promoters and hordein signal peptides may be used in the present invention. Homologs and variants of these nucleic acid molecules will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al., (1988); Huang et al., (1992); and Pearson et al., (1994). Altschul et al., (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at http://www.ncbi.nlm.nih.gov/BLAST. A description of how to determine sequence identity using this program is available at http://www.nchi.nlm.nih.gov/BLAST/blast.help.html.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 90% or at least about 95% sequence identity.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region. This method of sequence identity can be applied in the analysis of amino acid and nucleic acid sequences.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

The alignment tools ALIGN (Myers and Miller, 1989) or LFASTA (Pearson and Lipman, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the internet at http://biology.ncsa.uiuc.edu.

In a preferred embodiment, orthologs of the disclosed barley thioredoxin h protein are typically characterized by possession of greater than 90.6% sequence identity counted over the full-length alignment with the amino acid sequence of barley thioredoxin h using ALIGN set to default parameters. Proteins with even greater similarity to the reference sequences will show increasing percentage identities when assessed by this method, such as at least 92%, at least 93%, at least 95%, at least 96%, at least 97%, or at least 98% sequence identity. When less than the entire sequence is being compared for sequence identity, homologs will typically possess at least 90% sequence identity over short windows of 10–20 amino acids, and may possess sequence identities of at least 93%, at least 95%, at least 97%, or at least 99% depending on their similarity to the reference sequence. Sequence identity over such short windows can be determined using LFASTA; methods are described at http://biology.ncsa.uiuc.edu. One of skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

In a preferred embodiment, members of a thioredoxin h protein family having thioredoxin protein biological activity sharing amino acid sequence identity with the amino acid sequence of the prototypical barley thioredoxin h protein shown in SEQ ID NO:2. In a preferred embodiment, BTRXh proteins of the invention will generally share greater than 90.2% amino acid sequence identity with the sequence shown in SEQ ID NO:2, as determined using ALIGN set to default parameters. More closely related thioredoxin proteins may share at least 92%, 95%, or 98% sequence identity with the exemplified BTRXh protein.

In a preferred embodiment, a protein is a "NTR protein" as defined herein if the overall sequence identity of the amino acid sequence of FIG. 4A (SEQ ID NO:9) is preferably greater than about 71%, more preferably greater than about 85%, even more preferably greater than about 90% and most preferably greater than 95%. In some embodiments the sequence identity will be as high as about 98% and higher.

Barley thioredoxin h derived proteins and NTR derived proteins include fragments, respectively of thioredoxin h or NTR, generated either by chemical (e.g. enzymatic) digestion or genetic engineering means; chemically functionalized protein molecules obtained starting with disclosed protein or nucleic acid sequences, and protein sequence variants, which retain measurable thioredoxin h protein biological activity.

For example, while the prototypical barley thioredoxin h protein shown in SEQ ID NO:2 is 122 amino acids in length, one of skill in the art will appreciate that thioredoxin biological activity may be obtained using a protein that comprises less than the full length barley thioredoxin h protein. Thus the terms "barley thioredoxin h protein" and "barley NTR protein" includes fragments, respectively, of a full length barley thioredoxin h protein, which fragments retain thioredoxin protein biological activity or NTR protein biological activity, and variants, such as, naturally occurring allelic variants and mutants obtained by in vitro mutagenesis techniques and the like as further described below.

In one embodiment, BTRXh and NTR nucleic acids or BTRXh and NTR proteins are initially identified by substantial nucleic acid and/or amino acid sequence identity or similarity to the sequence(s) provided herein. In a preferred embodiment, BTRXh or NTR nucleic acids or Brtxh or NTR proteins have sequence identity or similarity to the sequences provided herein and one or more of their respective "biological activities". Such sequence identity or similarity can be based upon the overall nucleic acid or amino acid sequence.

The BTRXh and NTR proteins of the present invention may be shorter or longer than the amino acid sequence encoded by the exemplified nucleic acids shown in SEQ ID NO:2 and SEQ ID NO:9. Thus, in a preferred embodiment, included within the definition of BTRXh or NTR proteins are portions or fragments of the respective amino acid sequence encoded by the nucleic acid sequence provided herein. In one embodiment herein, fragments of BTRXh or NTR proteins are considered BTRXh or NTR proteins if a) a fragment shares at least one antigenic epitope with the corresponding exemplified sequence; b) has at least the indicated sequence homology; and c) preferably have an BTRXh or NTR biological activity or enzymatic activity as further defined herein. In some cases, where the sequence is used diagnostically, that is, when the presence or absence of a BTRXh or an NTR protein nucleic acid is determined, only the indicated sequence identity is required. The nucleic acids of the present invention may also be shorter or longer than the exemplified sequences in FIG. 2 (SEQ ID NO:1) or FIG. 5A (SEQ ID NO:10). The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, a BTRXh or an NTR protein can be made that are longer than those depicted in FIG. 1 (SEQ ID NO:2) and FIG. 4 (SEQ ID NO:9); for example, by the addition of epitope or purification tags, the addition of other fusion sequences, or the elucidation of additional coding and non-coding sequences. As described below, the fusion of a NTR peptide to a fluorescent peptide, such as Green Fluorescent Peptide (GFP), is particularly preferred.

Figure 2:
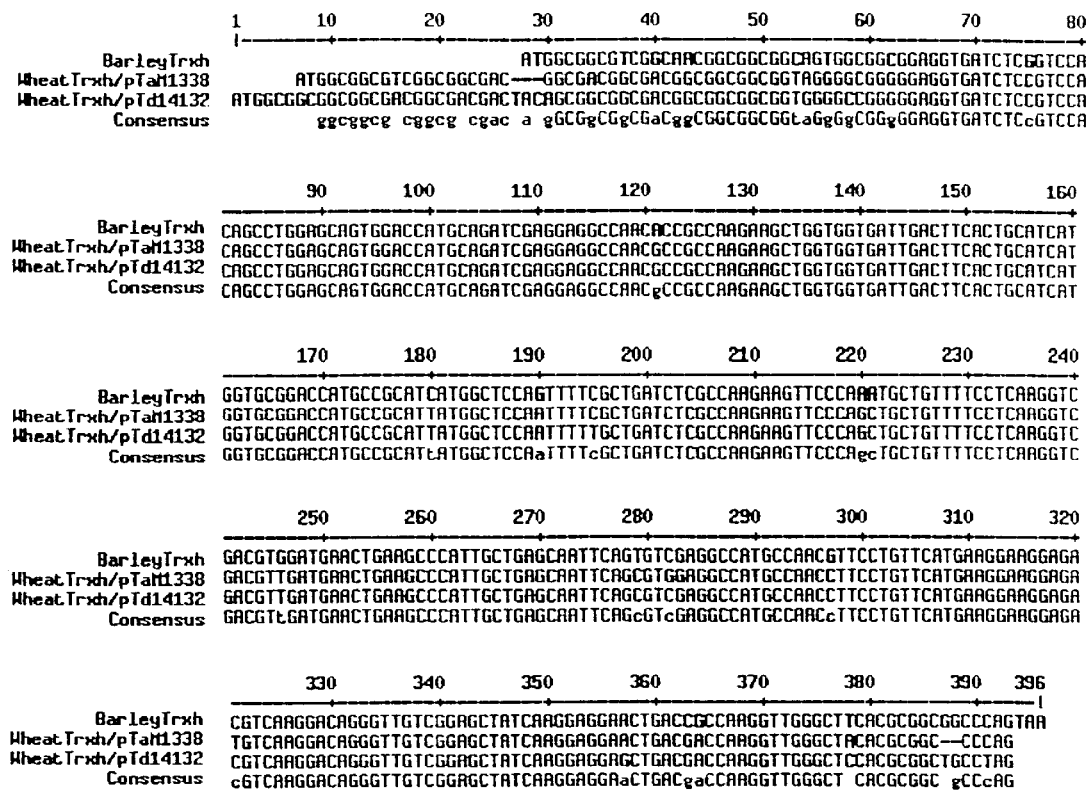
FIG. 2 shows a comparison of the nucleic acid sequence encoding barley thioredoxin h and two wheat thioredoxin h molecules, and a consensus sequence derived by the comparison of these three sequences. The BTRXh and wheat Trxh have about 90% sequence identity from positions 30–394.

BTRXh or NTR proteins may also be identified as encoded by BTRXh or NTR nucleic acids which hybridize to the sequence depicted in the FIG. 2 (SEQ ID NO:1) or FIG. 5A (SEQ ID NO:10) or the complement thereof, as outlined herein. Hybridization conditions are further described below.

In a preferred embodiment, when a BTRXh or NTR protein is to be used to generate antibodies, a BTRXh or an NTR protein must share at least one epitope or determinant with the full length protein. By "epitope" or "determinant" herein is meant a portion of a protein which will generate and/or bind an antibody. Thus, in most instances, antibodies made to a smaller BTRXh or NTR protein will be able to bind to the full length protein. In a preferred embodiment, the epitope is unique; that is, antibodies generated to a unique epitope show little or no cross-reactivity. The term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies (Harlow & Lane, 1988).

In a preferred embodiment, an antibody to an BTRXh or NTR protein upon binding to an NTR protein reduce or eliminate at least one biological activity of the NTR protein as described herein. That is, the addition of anti BTRXh or an anti-NTR protein antibodies (either polyclonal or preferably monoclonal) to anti-Btrxh or NTR proteins (or cells containing Brtxh or NTR proteins) may reduce or eliminate a BTRXh or an NTR activity. Generally, for both proteins of the invention at least a 25% decrease in activity is preferred, with at least about 50% being particularly preferred and about a 95–100% decrease being especially preferred.

The antibodies of the invention specifically bind to either BTRXh or NTR proteins. By "specifically bind" herein is meant that an antibody bind to a protein with a binding constant in the range of at least $10^{-4}$–$10^{-6}$ $M^{-1}$, with a preferred range being $10^{-7}$–$10^{-9}$ $M^{-1}$. Antibodies are further described below.

In the case of the BTRXh or NTR nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the encoded protein sequence.

Thus the NTR nucleic acid sequence identity of the nucleic acid sequence as compared to the nucleic acid sequence of the Figures is preferably greater than 75%, more preferably greater than about 80%, particularly greater than about 85% and most preferably greater than 90%. In some embodiments the sequence identity will be as high as about 93 to 95 or 98%.

In a preferred embodiment, a NTR nucleic acid encodes a NTR protein; whereas a BTRXh nucleic acid encodes a BTRXh protein. As will be appreciated by those in the art, due to the degeneracy of the genetic code, an extremely large number of nucleic acids may be made, all of which encode either the BTRXh or the NTR proteins of the present invention. Thus, having identified a particular amino acid sequence, those skilled in the art could make any number of different nucleic acids, by simply modifying the sequence of one or more codons in a way which does not change the amino acid sequence of the encoded protein.

In one embodiment, the BTRXh or the NTR nucleic acid is determined through hybridization studies. Thus, for example, nucleic acids which hybridize under high stringency to the nucleic acid sequence shown in FIG. 2 (SEQ ID NO:1) or FIG. 5A (SEQ ID NO:10), or their complement are considered either a BTRXh or an NTR nucleic acid. High stringency conditions are known in the art; see for example Sambrook et al., Molecular Cloning: A Laboratory Manual, 2d Edition, 1989, and Short Protocols in Molecular Biology, ed. Ausubel, et al., and Tijssen, Techniques in Biochemistry and Molecular Biology-Hybridization with Nucleic Acid Probes, "Overview of principles of hybridization and the strategy of nucleic acid assays" (1993), all of which are hereby incorporated by reference in their entirety. Stringent conditions are sequence-dependent and will be different in different circumstances. Longer sequences specifically hybridize at higher temperatures. Generally, stringent conditions are selected to be about 5–10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Thus, it is known in the art that hybridization stringency is an objective measure of sequence relatedness. Stringent conditions will be those in which the salt concentration is less than about 1.0 M sodium ion, typically about 0.01 to 1.0 M sodium ion concentration (or other salts) at about pH 7.0 to 8.3 and the temperature is at least about 30° C. for short probes (e.g. about 10 to 50 nucleotides) and at least about 60° C. for long probes (e.g. greater than about 50 nucleotides). Stringent conditions may also be achieved with the addition of destabilizing agents such as formamide. In a preferred embodiment, high stringency conditions are 0.1×SSC at 65° C.

In another embodiment, less stringent hybridization conditions are used; for example, moderate or low stringency conditions may be used, as are known in the art; see Maniatis and Ausubel, supra, and Tijssen, supra.

In a preferred embodiment, the BTRXh and NTR proteins and nucleic acids of the present invention are recombinant.

As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the Figures also include the complement of the sequence. By the term "recombinant nucleic acid" herein is meant nucleic acid, originally formed in vitro, in general, by the manipulation of nucleic acid by an endonuclease and/or a polymerase and/or a ligase and/or a recombinase, in a form not normally found in nature. Thus a recombinant BTRXh or NTR nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as described herein. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a BTRXh or NTR protein from one organism in a different organism or host cell. Alternatively, the protein may be made at a significantly higher concentration than is normally seen, through the use of an inducible promoter or high expression promoter or by increasing the number of copies of a nucleic cid encoding the BTRXh or NTR protein, such that the protein is made at increased concentration levels. Alternatively, the protein may be in a form not normally found in nature, as in the addition of an epitope tag or amino acid substitutions, insertions, and/or deletions, as discussed below.

In one embodiment, the present invention provides BTRXh and NTR protein variants. These variants fall into one or more of three classes: substitutional, insertional or deletional variants. These variants ordinarily are prepared by site specific mutagenesis of nucleotides in the DNA encoding a BTRXh or an NTR protein, using cassette mutagenesis, alanine scanning mutagenesis, glycine scanning mutagenesis, PCR mutagenesis, gene shuffling or other techniques well known in the art, to produce a nucleic acid encoding the variant, and thereafter expressing the nucleic acid in recombinant host cell culture as outlined above. However, variant BTRXh or NTR protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the BTRXh or NTR protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed BTRXh or NTR variants screened for the optimal combination of desired activity.

Techniques for making substitution mutations at predetermined sites in DNA having a known sequence are well known and include, for example, M13 primer mutagenesis, PCR mutagenesis, gene shuffling. Screening of the mutants is done using assays of BTRXh or NTR protein activities and/or properties as defined herein.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the BTRXh or NTR protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

Covalent modifications of BTRXh or NTR polypeptides are included within the scope of this invention. One type of covalent modification includes reacting targeted amino acid residues of a BTRXh or NTR polypeptide with an organic derivatizing agent that is capable of reacting with selected side chains or the N-or C-terminal residues of a BTRXh or NTR polypeptide. Derivatization with bifunctional agents is useful, for instance, for crosslinking a BTRXh or NTR protein to a water-insoluble support matrix or surface for use in the method of purifying anti-Btrxh or anti-NTR antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the BTRXh or NTR polypeptide included within the scope of this invention comprises altering the native glycosylation pattern of the polypeptide. "Altering the native glycosylation pattern" is intended for purposes herein to mean deleting one or more carbohydrate moieties found in native sequence of a BTRXh or NTR polypeptide, if present, and/or adding one or more glycosylation sites that are not present in the native sequence BTRXh or NTR polypeptide.

Addition of glycosylation sites to Brtxh or NTR polypeptides may be accomplished by altering the amino acid sequence thereof. The alteration may be made, for example, by the addition of, or substitution by, one or more serine or threonine residues to the native sequence BTRXh or NTR polypeptide (for O-linked glycosylation sites). The alteration also may be made, for example, by the addition of, or substitution by one or more Axn-Xaa-Ser/Thr sites (Xaa= any amino acid) in the native sequence BTRXh or NTR polypeptide (for N-linked glycosylation sites). The BTRXh or NTR amino acid sequence may optionally be altered through changes at the DNA level, particularly by mutating the DNA encoding the BTRXh or NTR polypeptide at preselected bases such that codons are generated that will translate into the desired amino acids.

Another means of increasing the number of carbohydrate moieties on the BTRXh or NTR polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the BTRXh or NTR polypeptide may be accomplished chemically or enzymatically or by mutational substitution of codons encoding for amino acid residues that serve as targets for glycosylation. Chemical deglycosylation techniques are known in the art and described, for instance, by Hakimuddin, et at., *Arch. Biochem. Biophys.*, 259:52 (1987) and by Edge et al., *Anal. Biochem.*, 118:131 (1981). Enzymatic cleavage of carbohydrate moieties if present on polypeptides or variant polypeptides can be achieved by the use of a variety of endo- and exo-glycosidases as described by Thotakura et al., *Meth. Enzymol.*, 138:350 (1987).

Another type of covalent modification of BTRXh or NTR polypeptide comprises linking the BTRXh or NTR polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

BTRXh or NTR polypeptides of the present invention may also be modified in a way to form chimeric molecules comprising an BTRXh or NTR polypeptide fused to another, heterologous polypeptide or amino acid sequence. Encompassed within this embodiment are Btrxh-NTR fusions. In one embodiment, such a chimeric molecule comprises a fusion of a BTRXh or NTR polypeptide with a tag polypeptide which provides an epitope to which an anti-tag antibody can selectively bind. The epitope tag is generally placed at the amino-or carboxyl-terminus of the BTRXh or NTR polypeptide but may be incorporated as an internal insertion or substitution. The presence of such epitope-tagged forms of a BTRXh or NTR polypeptide can be detected using an antibody against the tag polypeptide. Also, provision of the epitope tag enables the BTRXh or NTR polypeptide to be readily purified by affinity purification using an anti-tag antibody or another type of affinity matrix that binds to the epitope tag. In an alternative embodiment, the chimeric molecule may comprise a fusion of a BTRXh or NTR polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:63936397 (1990)] and the histidine tag and metal binding sites (Smith, Ann. NY. Acad. Sci., 646:315–321 (1991)], with the Flag and histidine tag being preferred.

In an embodiment herein, nucleic acids comprising sequences homologous to the exemplified BTRXh and NTR proteins of other organisms or tissues or alleles are cloned and expressed as outlined below. Thus, probe or degenerate polymerase chain reaction (PCR) primer sequences may be used to find other related BTRXh or NTR proteins from humans or other organisms. As will be appreciated by those in the art, particularly useful probe and/or PCR primer sequences include the unique areas of the BTRXh or NTR nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art (Innis et al., 1990). It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant Brtxh or NTR nucleic acid can be further-used as a probe to identify and isolate related Brtxh or NTR nucleic acids. It can also be used as a precursor nucleic acid to make modified or variant BTRXh or NTR nucleic acids and proteins.

Using the nucleic acids of the present invention which encode an BTRXh or NTR protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the BTRXh or NTR protein. The term "control sequences" refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the BTRXh or NTR protein; for example, transcriptional and translational regulatory nucleic acid sequences from barley are preferably used to express the NTR protein in barley. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or plant cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system for use in plant cells and for production of transgenic plants are provided herein and in the Examples.

BTRXh or NTR proteins of the present invention are produced by culturing a host cell transformed with an expression vector containing nucleic acid encoding a BTRXh or NTR protein, under the appropriate conditions to induce or cause expression of the BTRXh or NTR protein. The conditions appropriate for BTRXh or NTR protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include plant, yeast, bacteria, archebacteria, fungi, insect, and animal cells, including mammalian cells. Of particular interest are plant embryos, plant seeds and grains, root cells, stem cells, leaf cells, and other plant cells, Drosophila melangaster cells, Saccharomyces cerevisiae and other yeasts, E. coli, Bacillus subtilis, SF9 cells, C129 cells, 293 cells, Neurospora, BHK, CHO, COS, and HeLa cells, fibroblasts, Schwanoma cell lines, immortalized mammalian myeloid and lymphoid cell lines, with HeLa, SF9, and plant cells being preferred.

In a preferred embodiment, the BTRXh or NTR proteins are expressed in seed, grain, root, stem, leaf cells etc of dicotyledonous plants and monocotyledonous plants. Thus, BTRXh and NTR are expressed, for example, in wheat (Triticum spp.), rice (Olyza spp.), barley (Hordeum spp.), oat (Avena spp.), rye (Secale spp.), maize, corn (Zea mays), sorghum (Sorghum spp.), millet (Pennisetum spp.), Brassica spp., soybean, cotton, beans in general, rape/canola, alfalfa, flax, sunflower, safflower, cotton, tobacco, flax, peanut, clover, cowpea, grapes, forages grass varieties; vegetables such as lettuce, tomato, curcurbits, cassava, potato, carrot, radish, pea, lentils, cabbage, sugar beets, cauliflower, broccoli, sugar beats, Brussels sprouts, peppers; tree fruits such as citrus, apples, pears, peaches, apricots, walnuts; and ornamentals such as turf grasses, carnations and roses. In a preferred embodiment, the present invention can be employed with barley genotypes including, but not limited to Morex, Harrington , Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

A number of recombinant vectors suitable for stable transfection or transformation of plant cells or for the establishment of transgenic plants have been described including those described in Weissbach and Weissbach (1989), and Gelvin et al. (1990). Typically, plant transformation vectors include one or more cloned plant genes (or cDNAs) under the transcriptional control of 5' and 3' regulatory sequences, and a dominant selectable marker. Such plant transformation vectors typically also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and/or a polyadenylation signal.

Examples of constitutive plant promoters that may be useful for expressing the an operatively linked nucleic acid include: the cauliflower mosaic virus (CaMV) 35S promoter, which confers constitutive, high-level expression in most plant tissues (see, e.g, Odel et al., 1985, Dekeyser et al., 1990, Terada and Shimamoto, 1990; Benfey and Chua, 1990); the nopaline synthase promotertan et al., 1988); the maize ubiquitin promoter (Christianson & Quail, 1996) and the octopine synthase promoter (Fromm et al., 1989).

A variety of plant gene promoters that are regulated in response to environmental, hormonal, chemical, and/or developmental signals, also can be used for expression of the Btrwh or NTR nucleic acid in plant cells, including promoters regulated by: (a) heat (Callis et al., 1988; Ainley, et al. 1993; Gilmartin et al. 1992); (b) light (e.g, the pea rbcS-3A promoter, Kuhlemeier et al., 1989, and the maize rbcS promoter, Schaffner and Sheen, 1 99 1); (c) wounding (e.g, wun1, Siebertz et al., 1 9893; (d) hormones, such as abscisic acid (Marcotte et al., 1989); and (e) chemicals such as methyl jasminate or salicylic acid (see also Gatz, 1997).

In an alternative embodiment, tissue or organ specific (root, leaf, flower, and seed for example) promoters (Carpenter et al., 1992; Denis et al., 1993; Opperman et al., 1994; Stockhauser et al., 1997; Roshal et al., 1987; Schemthaner et al., 1988; Bustos et al., 1989) can be operably linked to the coding sequence to obtain particular expression in respective organs. For instance, monocot tissue-specific promoters may be used to attain expression in the aleurone (U.S. Pat. No. 5,525,716) or the endosperm (U.S. Pat. No. 5,677,474) of cereal and other grains.

In a preferred embodiment, a transgene of the invention, the Btrwh or NTR nucleic acid, is expressed in an edible part of a plant. By "edible" herein is meant at least a part of a plant that is suitable for consumption by humans or animals (fish, crustaceans, isopods, decapods, monkeys, cows, goats, pigs, rabbits, horses, birds (chickens, parrots etc). Accordingly, "edible" embraces food for human consumption and feed for animal consumption and includes, for example, dough, bread, cookies, pasta, pastry, beverages, beer, food additives, thickeners, malt, extracts made from an edible part of plants, animals feeds, and the like. An edible part of a plant includes for example, a root, a tuber, a seed, grain, a flower, fruit, leaf etc. The skilled artisan is aware that expression of the transgene is effected in any tissue, organ or part of a plant by employing a promoter that is active in the selected part of the plant the transgene is to be expressed. In a preferred embodiment the transgene is expressed in a seed or grain, preferably under control of a seed- or grain-specific promoter.

The expression of a Btrwh or NTR nucleic acid transgene in seeds or grains according to the present invention is preferably accomplished by operably linking a seed-specific or grain-specific promoter to the nucleic acid molecule encoding the transgene Btrwh or NTR protein. In this context, "seed-specific" indicates that the promoter has enhanced activity in seeds compared to other plant tissues; it does not require that the promoter is solely active in the seeds. Accordingly, "grain-specific" indicates that the promoter has enhanced activity in grains compared to other plant tissues; it does not require that the promoter is solely active in the grain. Preferably, the seed- or grain-specific promoter selected will, at the time when the promoter is most active in seeds, produce expression of a protein in the seed of a plant that is at least about two-fold greater than expression of the protein produced by that same promoter in the leaves or roots of the plant. However, given the nature of the Btrwx and NTR protein, it may be advantageous to select a seed- or grain-specific promoter that causes little or no protein expression in tissues other than seed or grain. In a preferred embodiment, a promoter is specific for seed and grain expression, such that, expression in the seed and grain is enhanced as compared to other plant tissues but does not require that the promoter be sole activity in the grain or seed. In a preferred embodiment, the promoter is "specific" for a structure or element of a seed or grain, such as an embryo-specific promoter. In accordance with the definitions provided above, an embryo-specific promoter has enhanced activity in an embryo as compared to other parts of a seed or grain or a plant and does not require its activity to be limited to an embryo. In a preferred embodiment, the promoter is "maturation-specific" and accordingly has enhanced activity developmentally during the maturation of a part of a plant as compared to other parts of a plant and does not require its activity to be limited to the development of one part of a plant.

A seed- or grain-specific promoter may produce expression in various parts of the seed or grain, including the endosperm, embryo, aleurone etc. or grain. Any seed- or grain-specific promoter may be used for this purpose, although it will be advantageous to select a seed- or grain-specific promoter that produces high level expression of the protein in the plant seed or grain. Known seed- or grain-specific promoters include those associated with genes that encode plant seed storage proteins such as genes encoding: barley hordeins, rice glutelins, oryzins, or prolamines; wheat gliadins or glutenins; maize zeins or glutelins; maize embryo-specific promoter; oat glutelins; sorghum kafirins; millet pennisetins; or rye secalins.

The barley hordein promoters (described in more detail below) are seed- or grain-specific promoters that were used in the illustrative Examples.

In certain embodiments, the seed- or grain-specific promoter that is selected is a maturation-specific promoter. The use of promoters that confer enhanced expression during seed or grain maturation (such as the barley hordein promoters) may result in even higher levels of thioredoxin expression in the seed.

By "seed or grain-maturation" herein refers to the period starting with fertilization in which metabolizable food reserves (e.g., proteins, lipids, starch, etc.) are deposited in the developing seed, particularly in storage organs of the seed, including the endosperm, testa, aleurone layer, embryo, and scutellar epithelium, resulting in enlargement and filling of the seed and ending with seed desiccation.

Members of the grass family, which include the cereal grains, produce dry, one-seeded fruits. This type of fruit, is strictly speaking, a caryopsis but is commonly called a kernel or grain. The caryopsis of a fruit coat or pericarp, which surrounds the seed and adhere tightly to a seed coat. The seed consists of an embryo or germ and an endosperm enclosed by a nucellar epidermis and a seed coat. Accordingly the grain comprises the seed and its coat or pericarp. The seed comprises the embryo and the endosperm. (R. Carl Hoseney in "Principles of Cereal Science and Technology", expressly incorporated by reference in its entirety).

In a preferred embodiment a hordein promoter is operably linked to a BTRXh or NTR nucleic acid. By "hordein promoter" and grammatical equivalents herein is meant, a barley promoter that directs transcription of a hordein gene in barley seeds or grain. A number of barley hordein genes and associated promoters have been described and characterized, including those for the B-, C-, D-, and Gamma-hordeins (Brandt et a., 1985; Forde et al, 1985; Rasmussen and Brandt, 1986, Sørensen et al., 1996). The activities of these promoters in transient expression assays have also been characterized (Entwistle et al., 1991; Muller and Knudesen, 1993; Sørensen et al, 1996). While any hordein promoter may be employed for this invention, the specific Examples provided describe the use of the promoter sequences from the $B_1$- and D-hordein genes of barley. The nucleic acid sequences of the barley $B_1$- and D-hordein genes are shown in SEQ ID NOs:11 and 12, respectively and in FIGS. 11 and 12 (the promoter region excludes those nucleotides that encode the hordein signal peptide that is shown underlined). Sørensen et al., (1996) describes plasmids that comprise the $B_1$- and D-hordein promoters operably linked to a beta-glucuronidase gene (uidA; gus) and the *Agrobacterium tumefaciens* nopaline synthase 3' polyadenylation site (nos). These plasmids may be conveniently utilized as sources of both the hordein promoters and the nos polyadenylation site.

One of skill in the art will appreciate that the length of the hordein promoter region may also be greater or less than the sequences depicted in FIGS. 11 and 12. For example, additional 5' sequence from the hordein gene upstream region may be added to the promoter sequence, or bases may be removed from the depicted sequences. However, any hordein promoter sequence must be able to direct transcription of an operably linked sequence in plant seed or grain. The ability of a barley hordein promoter to direct transcription of a protein in a plant seed may readily be assessed by operably linking the promoter sequence to an open reading frame (ORF) that encodes a readily detectable protein, such as the gus ORF, introducing the resulting construct into plants and then assessing expression of the protein in seeds of the plant (see Sørensen et al., 1996). A hordein promoter will typically confer seed-specific expression, meaning that expression of the protein encoded by the operably linked ORF will generally be at least about twice as high (assessed on an activity basis) in seeds of the stably transfected plant compared to other tissues such as leaves. More usually, the hordein promoter will produce expression in seeds that is at least about 5 times higher than expression in other tissues of the plant.

Functional homologs of the barley hordein promoters disclosed herein may be obtained from other plant species, such as from other monocots, including wheat, rice and corn. Such homologs may have specified levels of sequence identity with the prototype hordein promoters (e.g., at least 40% sequence identity). The functional homologs retain hordein promoter function, i.e., retain the ability to confer seed- or grain-specific expression of operably linked ORFs when introduced into plants (Marris et al., 1988; Mena et al., 1998). Accordingly, where reference is made herein to a hordein promoter, it will be understood that such reference includes not only nucleic acid molecules having the sequences of the prototypical sequences disclosed herein (or variations on these sequences), but also promoters from hordein gene homologs. Also included within the scope of such terms are molecules that differ from the disclosed prototypical molecules by minor variations. Such variant sequences may be produced by manipulating the nucleotide sequence of hordein promoter using standard procedures such as site-directed mutagenesis or the polymerase chain reaction. Preferably, the seed- or grain-specificity of the promoter is retained. Examples of dicot promoters that can be used include for example soybean glycinins and con-glycinins, and kidney bean phaseolin promoters.

In a preferred embodiment, the vector for plant expression of BTRXh and NTR polypeptides comprises a signal sequence which encodes a signal peptide. As described in the Examples below, the inventors have discovered that the level of expression of a transgene in seed or grain can be enhanced by the presence of a signal peptide. In one of the Examples described below, the $B_1$ hordein signal peptide was utilized. In particular, it was discovered that the expression of thioredoxin protein in seed or grain is enhanced when the ORF encoding the protein is operably linked to both a hordein promoter and a hordein signal sequence encoding the signal peptide. (For convenience, the nucleic acid sequence encoding a signal peptide is referred to herein as a signal sequence (SS).) While not wishing to be bound by theory, it is proposed that the hordein signal peptide directs expression of the thioredoxin protein to a protected subcellular location, such as a vacuole or protein body. It is further proposed that proteins directed to such vacuoles are protected from proteolysis during certain stages of seed or grain maturation. In addition, the sequestration of the BTRXh or NTR protein to such a location may also serve to protect the maturing seeds or grain from detrimental effects associated with over-expression of said proteins.

The hordein signal peptide typically comprises about the first 15–25 amino acids of the hordein gene ORF, more usually about 18–21 amino acids. The nucleotide and amino acid sequences of the hordein signal sequence and peptide of the prototypical barley $B_1$- and D-hordein genes are shown in SEQ ID NO:11–12 and FIGS. 11 and 12. One of skill in the art will appreciate that while the $B_1$-hordein signal sequence and signal peptide are utilized in the examples described below, the invention is not limited to these specific sequences. For example, homologous sequences may be used as effectively, as may sequences that differ in exact nucleotide or amino acid sequences, provided that such sequences result in enhanced levels of the encoded protein in immature seed or grain. Typically, "enhanced expression" will be expression that is about twice that observed with an equivalent construct lacking the signal sequence. Accordingly, the term "hordein signal sequence" and "hordein signal peptide" includes not only the particular sequences shown herein, but also homologs and variants of these sequences.

Furthermore, the invention is not limited to the use of hordein signal peptides. Other signal peptides that serve to localize the thioredoxin co-translationally or post-translationally to a selected seed, grain or cell compartment may be employed. Other such signal sequences include those associated with storage proteins in maize, rice, wheat, soybeans, beans, and tobacco (see for example: Bagga et al., 1997; Torrent et al., 1997; Wu et al., 1998; Zheng et al., 1995; Grimwade et al., 1996; Conrad et al., 1998; and Takaiwa et al., 1995.)

In a preferred embodiment, plant transformation vectors may also include RNA processing signals, for example introns, which may be positioned upstream or downstream of the ORF sequence in the transgene. In addition, the expression vectors may also include additional regulatory sequences from the 3' untranslated region of plant genes, e.g., a 3' terminator region to increase stability of the mRNA, such as the PI-II terminator region of potato or the octopine or nopaline synthase (nos) 3' terminator regions.

Finally, as noted above, plant transformation vectors may also include dominant selectable marker genes to allow for the ready selection of transformants. Such genes include those encoding antibiotic resistance genes (e.g, resistance to hygromycin, kanamycin, bleomycin, G418, streptomycin or spectinomycin) and herbicide resistance genes (e.g., phosphinothricin acetyltransferase).

The vector and transcriptional regulatory elements used for transgene expression is selected at the discretion of the practitioner. In some instances, enhanced BTRXh or NTR polypeptide expression and/or activity is desired, and the respective transgene encoding sequence is operably linked to a high-level promoter such as the maize ubiquitin 1 promoter. Enhanced BTRXh or NTR activity may also be achieved by introducing into a plant a transformation vector containing a variant form of the BTRXh or NTR polypeptide encoding sequence, for example a form which varies from an exemplified sequence but encodes a protein that retains BTRXh or NTR biological activity.

Over-expression of BTRXh or NTR in plant or other type of eukaryotic or procaryotic expression system is usually measured as the increase in the BTRXh or NTR activity present in a sample. Such over-expression can be measured using standard thioredoxin activity and NTR activity assays. As used here, cells, tissues, or plants over-expressing BTRXh or NTR, or homologous or derived proteins having BTRXh or NTR polypeptide activity, generally will have activity levels attributable of at least 5% over that found in the equivalent wild-type (nontransformed) sample. Where particularly high levels of over-expression are desired, transformed cells will express at least 30%, more preferably at least 50%, even more preferred at least 70% or most preferred at least 100% more thioredoxin or NTR activity attributable in comparison to an equivalent wild-type or null segregant sample. Overexpression of BTRXh or NTR polypeptide activity also may be measured by assessing the amount of protein in plant tissues using well-known procedures.

In an alternative embodiment, a reduction of BTRXh or NTR activity, preferably in a transgenic plant, may be obtained by introducing into plants an antisense construct based on a BTRXh or NTR encoding sequence. For antisense suppression, a BTRXh or NTR encoding sequence is arranged in reverse orientation relative to the promoter sequence in the transformation expression vector. The introduced sequence need not be a full length barley thioredoxin h or NTR encoding sequence, and need not be exactly homologous to the native thioredoxin h or NTR cDNA or gene found in the plant species, type, cultivar, varietal, or subspecies to be transformed. Generally, however, where the introduced sequence is of shorter length, a higher degree of homology to the native thioredoxin sequence will be needed for effective antisense suppression.

The introduced antisense sequence in the vector generally will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous thioredoxin or NTR gene in the plant cell. Although the exact mechanism by which antisense RNA molecules interfere with gene expression has not been elucidated, without being bound by theory, the antisense RNA molecules bind to the endogenous mRNA molecules and thereby inhibit translation of the endogenous mRNA. The production and use of anti-sense constructs-are disclosed, for instance, in U.S. Pat. Nos. 5,773,692 (using constructs encoding anti-sense RNA for chlorophyll a/b binding protein to reduce plant chlorophyll content), and U.S. Pat. No. 5,741,684 (regulating the fertility of pollen in various plants through the use of anti-sense RNA to genes involved in pollen development or function).

Suppression of endogenous thioredoxin or NTR gene expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. S,543,508 to Haselhoff. Inclusion of ribozyme sequences within antisense RNAs may be used to confer RNA cleaving activity on the antisense RNA, such that endogenous mRNA molecules that bind to the antisense RNA are cleaved, leading to an enhanced antisense inhibition of endogenous gene expression.

In another embodiment, constructs from which a BTRXh or NTR encoding sequence (or a variant thereof) is overexpressed may be used to obtain co-suppression of the endogenous thioredoxin gene in the manner described in U.S. Pat. No. 5,231,021 to Jorgensen. Such co-suppression (also termed sense suppression) does not require that the entire BTRXh or NTR encoding sequence be introduced into the plant cells, nor does it require that the introduced sequence be exactly identical to the endogenous thioredoxin gene. However, as with antisense suppression, the suppressive efficiency is enhanced as (1) the introduced sequence is lengthened and (2) the sequence similarity between the introduced sequence and the endogenous thioredoxin h gene is increased.

In another embodiment, constructs expressing an untranslatable form of a BTRXh or NTR message may also be used to suppress the expression of endogenous thioredoxin or NTR activity. Methods for producing such constructs are described in U.S. Pat. No. 5,583,021 to Dougherty. Preferably, such constructs are made by introducing a premature stop codon into the BTRXh or NTR ORF.

Methods of introducing exogenous nucleic acids into a plant host or plant host cells are known in the art. Accordingly, the transformation vector is introduced into plant cells by one of a number of techniques (e.g, electroporation) and progeny plants containing the introduced nucleic acid molecule are selected. Preferably all or part of the transformation vector will stably integrate into the genome of the plant cell. The part of the transformation vector that integrates into the plant cell, and which contains the introduced encoding sequence and associated expression controlling sequences (the introduced "transgene"), may be referred to as the recombinant expression cassette.

Selection of progeny plants containing the introduced transgene may be made based upon the detection of an altered phenotype. Such a phenotype may result directly from the expressed encoding sequence cloned into the transformation vector (for instance, altered thioredoxin h expression) or may be manifested as enhanced resistance to a chemical agent (such as an antibiotic) as a result of the inclusion of a dominant selectable marker gene incorporated into the transformation vector.

Successful examples of the modification of plant characteristics by transformation with cloned cDNA sequences are replete in the technical and scientific literature. Selected examples, which serve to illustrate the knowledge in this field of technology include:

U.S. Pat. No. 5,571,706 ("Plant Virus Resistance Gene and Methods")

U.S. Pat. No. 5,677,175 ("Plant Pathogen Induced Proteins")

U.S. Pat. No. 5,750,386 ("Pathogen-Resistant Transgenic Plants")

U.S. Pat. No. 5,597,945 ("Plants Genetically Enhanced for Disease Resistance")

U.S. Pat. No. 5,589,615 ("Process for the Production of Transgenic Plants with Increased Nutritional Value Via the Expression of Modified 2S Storage Albumins")

U.S. Pat. No. 5.750,871 ("Transformation and Foreign Gene Expression in Brassica Species")

U.S. Pat. No. 5,268,526 ("Over-expression of Phytochrome in Transgenic Plants")

U.S. Pat. No. 5,780,708 ("Fertile Transgenic Corn Plants")

U.S. Pat. No. 5,538,880 ("Method For Preparing Fertile Transgenic Corn Plants")

U.S. Pat. No. 5,773,269 ("Fertile Transgenic Oat Plants")

U.S. Pat. No. 5,736,369 ("Method For Producing Transgenic Cereal Plants")

U.S. Pat. No. 5,610,042 ("Methods For Stable Transformation of Wheat")

U.S. Pat. No. 5,780,709 ("Transgenic Maize with Increased Mannitol Content")

PCT publication WO 98/48613 ("Compositions and Methods for Plant Transformation and Regeneration").

These examples include descriptions of transformation vector selection, transformation techniques and the construction of vectors designed to express, over-express, or under-express the introduced nucleic acid molecule. In light of the foregoing and the provision herein of the BTRXh or NTR encoding sequence, it is thus apparent that one of skill in the art will be able to introduce these nucleic acid sequences, or homologous or derivative forms of this molecule, into plant cells in order to produce plants having altered or enhanced barley thioredoxin activity.

Transformation and regeneration of both monocotyledonous and dicotyledonous plant cells is routine in the art and the practitioner will determine the appropriate transformation technique. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; microinjection of plant cells; micro-projectile bombardment of plant cells; vacuum infiltration; and *Agrobacterium tumefaciens* (AT)-mediated transformation. Typical procedures for transforming and regenerating plants are described in the patent documents listed at the beginning of this section. In addition, certain developments particularly enhance regeneration techniques for monocot plants (see, for instance, U.S. Pat. Nos. 4,666,844 and 5,589,617, and PCT application WO 98/48613). For instance, a vector comprising a barley thioredoxin h-encoding nucleic acid can be stably introduced to barley plants as described in a number of published protocols, including Wan and Lemaux 1994; Lemaux et al., 1996; and Cho et al., 1998a–c).

Depending on the transformation and regeneration protocol followed, transformed plants may be selected using a dominant selectable marker incorporated into the transformation vector or carried on a companion vector used for co-transformation. Typically, such a marker will confer antibiotic or herbicide resistance on the seedlings of transformed plants, and selection of transformants can be accomplished by exposing the seedlings to appropriate concentrations of the antibiotic.

After transformed plants are selected-and grown to maturity, they can be assayed using the methods described herein to determine whether expression of thioredoxin h has been altered as a result of the introduced transgene. Expression of the transformed barley thioredoxin h protein can be determined by Western blot analysis of transformed plant tissues or extracts using standard procedures. BTRXh and NTR activity assays, as discussed above, can be used to determine the activity of the expressed transgenic Btrwx or NTR. Untransformed and negative segregant plants also are preferably assayed for activity so the background level of BTRXh or NTR activity (provided by expression of endogenous genes, when present and being expressed) can be determined.

In a preferred embodiment, the BTRXh or NTR proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for BTRXh or NTR protein into mRNA. A promoter will have a transcription initiating region, which is usually placed proximal to the 5' end of the coding sequence, and a TATA box, usually located about 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, BTRXh or NTR proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of BTRXh or NTR protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence about 3–9 nucleotides in length located about 3–11 nucleotides upstream of the initiation codon.

The expression vector may also include a signal peptide sequence that provides for secretion of the BTRXh or NTR protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, BTRXh or NTR proteins are produced in insect cells. Expression vectors for the transformation of insect cells, and in particular, baculovirus-based expression vectors, are well known in the art.

In a preferred embodiment, BTRXh or NTR protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and acid phosphatase genes. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The BTRXh or NTR protein may also be made as a fusion protein, using techniques well known in the art. Thus, for example, for the creation of monoclonal antibodies, if the desired epitope is small, the BTRXh or NTR protein may be fused to a carrier protein to form an immunogen. Alternatively, the BTRXh or NTR may be made as a fusion protein to increase expression, or for other reasons. For example, when the BTRXh or NTR protein is an *H. vulgare* BTRXh or NTR peptide, the nucleic acid encoding the peptide may be linked to another nucleic acid for expression purposes. Similarly, BTRXh or NTR proteins of the invention can be linked to protein labels, such as green fluorescent protein (GFP), red fluorescent protein (RFP), blue fluorescent protein (BFP), yellow fluorescent protein (YFP), etc.

In one embodiment, the BTRXh or NTR nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the BTRXh or NTR protein is purified or isolated after expression. BTRXh or NTR proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the BTRXh or NTR protein may be purified using a standard anti-NTR antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the BTRXh or NTR protein. In some instances no purification will be necessary.

Once expressed and purified, if necessary, the BTRXh or NTR proteins and nucleic acids are useful in a number of applications.

The nucleotide sequences (or their complement) encoding BTRXh or NTR proteins have various applications in the art of molecular biology, including uses as hybridization probes, in chromosome and gene mapping and in the generation of anti-sense RNA and DNA. BTRXh or NTR protein nucleic acid will also be useful for the preparation of BTRXh or NTR proteins by the recombinant techniques described herein.

The full-length native sequence BTRXh or NTR protein gene, or portions thereof, may be used as hybridization probes for a cDNA library to isolate other genes (for instance, those encoding naturally-occurring, for example, allelic variants of BTRXh or NTR protein or BTRXh or NTR proteins from other genus or species) which have a desired sequence identity to the BTRXh or NTR protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the BTRXh or NTR protein gene using the known DNA sequence to synthesize a selected probe of about 40 bases. Hybridization probes may be labeled by a variety of labels, including radionuclides such as $^{32}P$ or $^{35}S$, or enzymatic labels such as alkaline phosphatase coupled to the probe via avidin/biotin coupling systems. Labeled probes having a sequence complementary to that of the BTRXh or NTR protein gene of the present invention can be used to screen libraries of human cDNA, genomic DNA or mRNA to determine to which members of such libraries the probe hybridizes.

Nucleotide sequences encoding a BTRXh or NTR protein can also be used to construct hybridization probes for mapping the gene which encodes that BTRXh or NTR protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode BTRXh or NTR protein or its modified forms can also be used to generate either transgenic plants, preferably as described above and in the Examples.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, microparticle bombardment (biolistic) etc. The currently preferred in vivo gene transfer techniques include transfection with viral (typically retroviral) vectors and viral coat protein-liposome mediated transfection (Dzau et al., Trends in Biotechnology 11, 205–210 [1993]). In some situations it is desirable to provide the nucleic acid source with an agent that targets the target cells to be transformed, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

In a preferred embodiment, the BTRXh or NTR proteins, nucleic acids, variants, modified proteins, cells and/or transgenics containing the said nucleic acids or proteins are used in screening assays. Identification of the BTRXh or NTR protein provided herein permits the design of screening assays for compounds that bind or modulate BTRXh or NTR activity.

"Modulating the activity of a BTRXh or NTR protein" includes an increase in activity, a decrease in activity, or a change in the type or kind of activity present. Thus, in this embodiment, the candidate agent should both bind to BTRXh or NTR protein (although this may not be necessary), and alter its biological or biochemical activity as defined herein. The methods include both in vitro screening methods, as are generally outlined above, and in vivo screening of cells for alterations in the presence, distribution, activity or amount of the BTRXh or NTR protein.

Methods of assaying a biological activity of a thioredoxin h protein are known in the art. Thioredoxins lack a directly measurable catalytic property that can be used in their detection and quantification. Therefore, a specific companion enzyme reaction is necessary to demonstrate and measure the activity of thioredoxin proteins. One of ordinary skill in the art will be aware that there are many well-established systems that can be employed to measure thioredoxin-mediated reduction of substrates. See, for instance, U.S. Pat. No. 5,792,506 to Buchanan; Horecka et al. (1996); Rivera-Madrid et al. (1995); Wong et al. (1995); Jacquot et al. (1990); Florencio et al. (1988); Florencio et al. (1988); Johnson et al. (1987); Schwenn and Schriek (1986); and Berstermann et al. (1983). Appropriate assay systems may be broken down into four major classes: 1) enzyme activation (using thioredoxin to modulate another enzyme in a measurable way); 2) ribonucleotide reduction (using thioredoxin as a co-substrate by ribonucleotide reductase); 3) protein disulfide reduction (using thioredoxin for insulin A-B chain reduction) (Schwenn and Schriek, 1987); and 4) direct measurement of disulfide reduction using monobromobimane (mBBr)-derivative fluorescence (Wong et al., 1995). Any such system can be used to measure thioredoxin activity. Different techniques will be more or less appropriate to specific plants and tissues. The appropriate technique will be determined at the discretion of the practitioner. By way of example, the following techniques are appropriate for measuring the activity of thioredoxin.

Because of interference from other enzymes that use NADPH, the activity of thioredoxin h cannot be accurately assayed in crude plant extracts. Thus, at least partial purification of the thioredoxin h protein is necessary. Such partial purification can be carried out using standard protein purification techniques, for instance $(NH_4)_2SO_4$ extraction and column chromatography. See, for example, Florencio et al. (1988) and Johnson et al. (1 987a,b).

Thioredoxin h activity-assayable transgenic barley seed extracts can be prepared in the following manner. In the embodiment, wherein Btrwh activity is assayed in a plant or plant tissue, such as a seed or grain, about fifteen grams of barley grains, may be ground to powder in a coffee grinder or other like device. Protein is subsequently extracted from this powder with 80 ml (1:4 w/v) of buffer (50 mM Tris-HCl buffer, pH 7.9, 1 mM EDTA, 0.5 mM PMSF (phenylmethysulfonyl fluoride), 2 mM e-amino-n caproic acid, 2 mM benzamidine-HCl) by stirring for three hours at 4° C. The slurry plus the rinse is then subjected to centrifugation at 25,400×g for 20 minutes, and the resultant supernatant solution decanted through glass wool. The pellet is resuspended in a small volume of buffer and then clarified by centrifugation as before. The two supernatant fractions are combined, an aliquot removed as a control, and the remainder subjected to acidification by adjusting the pH from about 7.83 to about 4.80 with 2 N formic acid. Denatured proteins should be removed from the acidified solution by centrifugation as above prior to assaying for enzyme activity. The pH of the acidified supernatant solution is then readjusted to 7.91 with 2 N $NH_4OH$ and an aliquot is removed for enzyme assay. Powdered $(NH_4)_2SO_4$ is added to a final concentration of 30% (w/v) and the sample stirred for 20 minutes at 4° C., followed by centrifugation as described above. Additional $(NH_4)_2SO_4$ is then added to bring the decanted supernatant solution to 90% (w/v) saturation, and the sample stirred for 16 hours at 4° C. This sample is centrifuged again as described above to yield a thioredoxin h-enriched pellet.

The supernatant solution from the thioredoxin h-enriched pellet is discarded, and the pellet re-suspended in 30 mM Tris-HCl, pH 7.9 buffer. This is then clarified by centrifugation at 40,000×g for 15 minutes. The resulting supernatant (30–50% $(NH_4)_2SO_4$ fraction) should then be placed in dialysis tubing (6,000–8,000 MW cut-off) and exposed to solid sucrose at 4° C. to obtain an approximate 10-fold reduction in volume. An aliquot (about 1 ml) of the clarified and concentrated 30–90% $(NH_4)_2SO_4$ sample should be reserved. The remaining sample is applied to a pre equilibrated (30 mM Tris-HCl, pH 7.9, 200 mM NaCl) Sephadex G-50 superfine column (2.5×90 cm; ~400 ml bed volume) with a peristaltic pump at a flow rate of 0.5 ml/min. Protein is eluted from the loaded column with the same buffer at the same flow rate, and 150-drop fractions collected. Each fraction can be tested for thioredoxin h activity using standard techniques, for instance the NADP-MDH activation protocol (see below). Storage of the prepared fractions should be at 4° C.

Thioredoxin h extracted from *E. coli* is stable after treatment at 60° C. for 10 minutes (Mark and Richardson, 1976). Using this feature of thioredoxin h proteins, the level of background (non-thioredoxin h) enzyme activity in crude plant extracts can be decreased by heating the crude extract at 60° C. for about ten minutes, using the following protocol. In the example of expression of BTRXh in transgenic grain, approximately ten grams of, for example, barley grain are ground to powder for about 30 seconds in a coffee grinder and extracted by shaking for 1 hour at room temperature in 50 ml buffer (50 mM Tris-HCl buffer, pH 7.9, 1 mM EDTA, 0.5 mM PMSF, 2 mM e-amino-n caproic acid, 2 mM benzamidine-HCl). The slurry plus the rinse is then subjected to centrifugation at 27,000×g for 20 minutes and the supernatant solution decanted through glass wool. A 20 ml aliquot of the supernatant is then heated at 65° C. until sample temperature reaches 60+1° C. (~10 minutes). The sample is then held at 60° C. for 10 additional minutes, then cooled in an ice/water bath. The cooled sample is centrifuged and the supernatant solution concentrated using solid sucrose as above. The resultant heat-treated, concentrated supernatant may be stored at −20° C. Frozen samples are thawed and clarified by centrifugation at 14,000 rpm for 10 minutes at 4° C. Total thioredoxin h activity can then be measured in these concentrated supernatant fractions.

Methods and techniques of measuring thioredoxin h activity have previously been described (see, for instance, Berstermann et al. 1983; Johnson et al. 1987; and Florencio et al. 1988). For each technique, about fifty to 120 µl (depending on activity) of partially purified or heat-treated plant extract as prepared above is pre-incubated with DTT, and 0.16 to 0.32 µl of this pre-incubation mixture is then used in the assay.

In general, thioredoxin h activity is assayed by adding thioredoxin-bearing sample to an NADP-thioredoxin reductase (NTR) assay system (Florencio et al., 1988; Gautier et al., 1998), and the reduction of DTNB measured. Essentially, NADPH provides the reducing equivalents needed for thioredoxin reductase to reduce thioredoxin h by converting it from the disulfide (—S—S—) to the sulthydryl (—SH) form. This reduced (sulthydryl) thioredoxin h then reduces DTNB directly. Reduction of DTNB is measured as an increase in absorbance of the sample at 412 nm.

By way of example, 1 ml reaction mixtures containing 100 µM potassium phosphate (pH 7.1), 10 µl mol @@@ 150 nmol EDTA, 150 nmol NADPH, 200 nmol DTNB (dissolved in 95% ethanol) and variable amounts of thioredoxin h-bearing samples are initiated by the addition of 10 pmol of wheat or *E. coli* NTR, and the reduction of DTNB determined by monitoring the absorbance change at 412 nm. The activity can then be expressed as µmol thioredoxin reduced per minute using 13,600 $M^{-1}$ $cm^{-1}$ as the molar absorption coefficient of DTNB (2-SH being formed/mol reduced thioredoxin).

In the NADP-Malate Dehydrogenase (MDH) Activation Assay, thioredoxin h activity is assayed by adding thioredoxin-bearing sample to an NADP-malate dehydrogenase (MDH) assay system (Johnson et al., 1987; Berstermann et al. 1983). This system is similar to that used in an NADP-NTR activation assay.

In vitro monobromobimane (mBBr) labeling of proteins is an alternate to indirectly measuring thioredoxin h protein activity using a companion-enzyme assay, thioredoxin-mediated disulfide reduction can be measured using monobromobimane (mBBr) derivative fluorescence (Crawford et al., 1989; Kobrehel et al., 1992; U.S. Pat. No. 5,792,506 "Neutralization of food allergens by thioredoxin"). By way of example only, the following describes an appropriate procedure as it relates to transgenic plants. Immature, mature, or germinating seeds or grain from nontransformed (control) and transgenic plants are ground in 100 mM Tris-HCl buffer, pH 7.9. Assay reactions may then be carried out essentially as described in Kobrehel et al. (1992). In general, 70 µL of the buffer mixture containing a known amount of protein is either untreated or treated with DTT to a final concentration of 0.5 mM. After incubation for 20 minutes, 100 nmol of mBBr is added, and the reaction continued for another 15 minutes. To stop the reaction and derivatize excess mBBr, 10 µl of 10% SDS and 100 µl of 100 mM 2-mercaptoethanol are added. The samples are then applied to a 15% SDS-PAGE gel. Fluorescence of mBBr may be visualized by placing gels on a light box fitted with a UV (365 nm) light source. Protein quantification can be carried out by the Bradford dye-binding method (Bradford, 1976) using, for instance, bovine serum albumin or gamma globulin as standards. This protocol has been adapted for barley as described by Cho et al, ((1999) Proc. Natl. Acad. Sci. USA 96:14641–14646).

Methods of measuring NTR activity also are known in the art. In a preferred embodiment, NTR activity is determined with the DNTB assay (Florencio et al., 1988). The system contains the amount of an extract, as needed, spinach thioredoxin h (2–5 µg) and the following: 100 µmol potassium phosphate buffer (pH 7.9). Ten µmol Na-EDTA; 0.25 µmol NADPH; 0.2 µmol DTNB. The reaction is started by the addition of thioredoxin h (final volume, 1.0 ml). Increase in absorbance is followed at 412 nm.

The content and activity of BTRXh and NTR is alternatively assessed by Western blot and activity measurements. In the example of transgenic seeds or grains, western blots are performed on extracts selected transgenic seeds or grain as well as non-transgenic seeds or grains, including null segregants. Lots of about 10–20 intacts seeds are grains are processed and analyzed for content of BTRXh and NTR by SDS-PAGE and western blot procedures (Cho et al, (1999) Proc. Natl. Acad. Sci. USA 96:14641–14646). Grain or seeds extract are preferably prepared as described by Cho et al., (1999) Plant Sci. 148:9–17).

Thus, in the embodiment of identifying a bioactive agent the alters a biological activity of a BTRXh or NTR polypeptide, the methods comprise combining an BTRXh or NTR sample and a candidate bioactive agent, and evaluating the effect on the BTRXh or NTR activity. By "BTRXh or NTR activity" or grammatical equivalents herein is meant one of the BTRXh or NTR protein's biological activities, including, but not limited to those described above and, for example, a BTRXh or NTR proteins ability to alter the oxidation/reduction state of $NADPH_2$ or thioredoxin in vitro or in vivo. Other biological activities include altering the oxidation/reduction state of a cell of a transgenic plant in which it is expressed, altering the digestibility of the starch or protein components of a transgenic seed or grain; redistribution of the proteins of a transgenic seed or grain to the more soluble albumin/globulin fraction and decreasing the allergenicity of a transgenic seed or grain.

In a preferred embodiment, the activity of the BTRXh or NTR protein is decreased; in another preferred embodiment, the activity of the BTRXh or NTR protein is increased. Thus, bioactive agents that are antagonists are preferred in some embodiments, and bioactive agents that are agonists may be preferred in other embodiments.

The assays described herein preferably utilize the *H. vulgare* BTRXh or NTR protein, although other plant proteins may also be used, including dicotyledonous plants (e.g. tomato, potato, soybean, cotton, tobacco, etc.) and monocotyledonous plants, including, but not limited to graminaceous monocots such as wheat (Triticum spp.), rice (Oryza spp.), barley (Hordeum spp.), oat (Avena spp.), rye (Secale spp.), corn (*Zea mays*), sorghum (Sorghum spp.) and millet (Pennisetum spp). For example, the present invention can be employed with barley genotypes including, but not limited to Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals. These latter embodiments may be preferred in the development of models of grain germination.

In a preferred embodiment, the methods comprise combining a BTRXh or NTR protein and a candidate bioactive agent, and determining the binding of the candidate agent to the BTRXh or NTR protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to alter or modulate BTRXh or NTR activity, may be used.

Candidate agents encompass numerous chemical classes, though typically they are organic molecules, preferably small organic compounds having a molecular weight of more than about 100 daltons and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an inter-action library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of plant, bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By nucleic acid"or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Left.*, 805 (1984), Letsinger, et al., *J. Am. Chem. Soc.*, 110:4470 (1988); and Pauwels, et al., *Chemica ScriDta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321

(1989)), 0-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Dempsey, et al., *Proc. Natl. Acad. Sci. USA*, 92:6097 (1995)); non-ionic backbones (U.S.,Pat. Nos. 5,386,023; 5,637,684; 5,602,240; 5,216,141; and 4,469,863; Kiedrowshi, et al., *Angew. Chem. Intl. Ed. English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Let:.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al, *Chem. Soc. Rev.*, (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, winch confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In one embodiment of the methods described herein, portions of BTRXh or NTR proteins are utilized; in a preferred embodiment, portions having BTRXh or NTR activity are used to identify agents that bind to BTRXh or NTR. In addition, the assays described herein may utilize either isolated BTRXh or NTR proteins or cells comprising the BTRXh or NTR proteins.

Generally, in a preferred embodiment of the methods herein, for example for binding assays, the BTRXh or NTR protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to “sticky” or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the BTRXh or NTR protein is bound to the support, and a candidate bioactive agent is added to the assay. Alternatively, the candidate agent is bound to the support and the BTRXh or NTR protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays, preferably oxidation/reduction assays.

The determination of the binding of the candidate bioactive agent to the BTRXh or NTR protein may be done in a number of ways. In a preferred embodiment, the candidate bioactive agent is labelled, and binding determined directly. For example, this may be done by attaching all or a portion of the BTRXh or NTR protein to a solid support, adding a labelled candidate agent (for example a radio or fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using 1251, or with fluorophores. Alternatively, more than one component may be labeled with different labels; using 1251 for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. BTRXh or NTR protein), such as an antibody peptide, binding partner, ligand, etc. Under certain circumstances, there may be competitive binding as between the bioactive agent and the binding moiety, with the binding moiety displacing the bioactive agent. This assay can be used to determine candidate agents which interfere with binding between BTRXh or NTR proteins and binding partners. "Interference of binding" as used herein means that native binding of the BTRXh or NTR protein differs in the presence of the candidate agent. The binding can be eliminated or can be with a reduced affinity. Therefore, in one embodiment, interference is caused by, for example, a confirmation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between about 0.1 and about 1.0 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the NTR protein and thus is capable of binding to, and potentially modulating, the activity of the NTR protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the BTRXh or NTR protein with a higher affinity. Thus, if the candidate bioactive agent is labeled, the presence of the label on the support, coupled with a lack of competitor binding, may indicate that the candidate agent is capable of binding to the BTRXh or NTR protein.

In a preferred embodiment, the methods comprise differential screening to identity bioactive agents that are capable of modulating the activity of the BTRXh or NTR proteins. Such assays can be done with the BTRXh or NTR protein or cells comprising said BTRXh or NTR protein. In one embodiment, the methods comprise combining an BTRXh or NTR protein and a competitor in a first sample. A second sample comprises a candidate bioactive agent, an BTRXh or NTR protein and a competitor. The binding of the competitor is determined for both samples, and a change, or difference in binding between the two samples indicates the presence of an agent capable of binding to the BTRXh or NTR protein and potentially modulating its activity. That is, if the binding of the competitor is different in the second sample relative to the first sample, the agent is capable of binding to the BTRXh or NTR protein.

Alternatively, a preferred embodiment utilizes differential screening to identify candidates that bind to the native BTRXh or NTR protein, but cannot bind to modified BTRXh or NTR proteins. The structure of the BTRXh or NTR protein may be modeled, and used in rational design and synthesis of agents that interact with that site. Drug candidates that affect BTRXh or NTR bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In a preferred embodiment, the invention provides methods of screening for bioactive agents capable of modulating the activity of an BTRXh or NTR protein. The methods comprise adding a candidate bioactive agent, as defined above, to a cell comprising BTRXh or NTR proteins. Preferred cell types include almost any cell. The cells contain a recombinant nucleic acid that encodes an BTRXh or NTR protein. In a preferred embodiment, a library of candidate agents are tested on a plurality of cells.

Detection of BTRXh or NTR regulation may be done as will be appreciated by those in the art. In one embodiment, indicators of the NTR activity are used, for example, oxidation of NADPH or reduction of thioredoxin, preferably thioredoxin h. In one embodiment, indicators of the BTRXh activity are used, for example, using the NADP-malate dehydrogenase activation assay as described by Florencio et al. 1988 and Johnson et al. (1987a). There are a number of parameters that may be evaluated or assayed to allow the detection of alterations in BTRXh or NTR regulation, including, but not limited to, cell viability assays, germination characteristics of a transgenic grain or seed, redox status of transgenic grain or seed, digestibility of a transgenic seed or grain, the expression of gibberellic acid inducible enzyme in a transgenic seed or grain. Other parameters include mRNA synthesis, translation, peptides, activity of a protein or enzyme, distribution of protein in, for example, more soluble verses less soluble fractions. By assaying or measuring one or more of these parameters, it is possible to detect not only alterations in BTRXh or NTR regulation, but alterations of different steps of the BTRXh or NTR regulation pathway. In this manner, rapid, accurate screening of candidate agents may be performed to identify agents that modulate BTRXh or NTR regulation.

Accordingly, the invention provides methods of screening for alterations in BTRXh or NTR regulation of a population of cells. By "alteration" or "modulation" (used herein interchangeably), is generally meant a change, for example, in the redox state of a substrate or co-factor of the BTRXh or NTR protein. In another embodiment, is meant a change in the redox state in a pathway affected by BTRXh or NTR activity.

The measurements can be determined wherein all of the conditions are the same for each measurement, or under various conditions, with or without bioactive agents, or at different stages of the cell cycle process. For example, a measurement of BTRXh or NTR regulation can be determined in a cell or cell population wherein a candidate bioactive agent is present and wherein the candidate bioactive agent is absent. In another example, the measurements of BTRXh or NTR regulation are determined wherein the condition or environment of the cell or populations of cells differ from one another. For example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the measurements of BTRXh or NTR regulation are determined at different stages of the cell cycle process. In yet another example, the measurements of BTRXh or NTR regulation are taken wherein the conditions are the same, and the alterations are between one cell or cell population and another cell or cell population.

By a "population of cells" or library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. The cells may be in any cell phase, either synchronously or not, including M, G1, S, and G2. In a preferred embodiment, cells that are replicating or proliferating are used; this may allow the use of retroviral vectors for the introduction of candidate bioactive agents. Alternatively, non-replicating cells may be used, and other vectors (such as adenovirus, lentivirus, and Agrobacterium vectors) can be used. In addition, although not required, the cells are compatible with dyes and antibodies.

Preferred cell types for use in the invention include, but are not limited to, plant cells, including mono- and dicot plants such as (cereal grains, barley, wheat sorghum, soybeans, sugar beets, peanuts, canola and as described above), and mammalian cells, including animal (rodents, including mice, rats, hamsters and gerbils), primates, and human cells, particularly including tumor cells of all types, including breast, skin, lung, cervix, colon-rectal, leukemia, brain, etc.

In a preferred embodiment, the methods comprise assaying one or more of several different cell parameters, including, but not limited to, cell viability, cell proliferation, and cell phase.

In a preferred embodiment, cell viability is assayed, to ensure that a lack of cellular change is due to experimental conditions (i.e. the introduction of a candidate bioactive agent) not cell death. There are a variety of suitable cell viability assays which can be used, including, but not limited to, light scattering, viability dye staining, and exclusion dye staining.

In a preferred embodiment, a light scattering assay is used as the viability assay, as is well known in the art For example, when viewed in the FACS, cells have particular characteristics as measured by their forward and 90 degree (side) light scatter properties. These scatter properties represent the size, shape and granule content of the cells. These properties account for two parameters to be measured as a readout for the viability. Briefly, the DNA of dying or dead cells generally condenses, which alters the 90° scatter; similarly, membrane blebbing can alter the forward scatter. Alterations in the intensity of light scattering, or the cell-refractive index indicate alterations in viability.

Thus, in general, for light scattering assays, a live cell population of a particular cell type is evaluated to determine it's forward and side scattering properties. This sets a standard for scattering that can subsequently be used.

In a preferred embodiment, the viability assay utilizes a viability dye. There are a number of known viability dyes that stain dead or dying cells, but do not stain growing cells. For example, annexin V is a member of a protein family which displays specific binding to phospholipid (phosphotidylserine) in a divalent ion dependent manner. This protein has been widely used for the measurement of apoptosis (programmed cell death) as cell surface exposure of phosphotidylserine is a hallmark early signal of this process. Suitable viability dyes include, but are not limited to, annexin, ethidium homodimer-1, DEAD Red, propidium iodide, SYTOX Green, etc., and others known in the art; see the Molecular Probes Handbook of Fluorescent Probes and Research Chemicals, Haugland, Sixth Edition, hereby incorporated by reference; see Apoptosis Assay on page 285 in particular, and Chapter 16.

Protocols for viability dye staining for cell viability are known, see Molecular Probes catalog, supra. In this embodiment, the viability dye such as annexin is labeled, either directly or indirectly, and combined with a cell population. Annexin is commercially available, i.e., from PharMingen, San Diego, Calif., or Caltag Laboratories, Millbrae, Calif. Preferably, the viability dye is provided in a solution wherein the dye is in a concentration of about 100 ng/ml to about 500 ng/ml, more preferably, about 500 ng/ml to about 1 $\mu$g/ml, and most preferably, from about 1 $\mu$g/ml to about 5 $\mu$g/ml. In a preferred embodiment, the viability dye is directly labeled; for example, annexin may be labeled with a fluorochrome such as fluorecein isothiocyanate (FITC), Alexa dyes, TRITC, AMCA, APC, tri-color, Cy-5, and others known in the art or commercially available. In an alternate preferred embodiment, the viability dye is labeled with a first label, such as a hapten such as biotin, and a secondary fluorescent label is used, such as fluorescent streptavidin. Other first and second labeling pairs can be used as will be appreciated by those in the art.

Once added, the viability dye is allowed to incubate with the cells for a period of time, and washed, if necessary. The cells are then sorted as outlined below to remove the non-viable cells.

In a preferred embodiment, exclusion dye staining is used as the viability assay. Exclusion dyes are those which are excluded from living cells, i.e. they are not taken up passively (they do not permeate the cell membrane of a live cell). However, due to the permeability of dead or dying cells, they are taken up by dead cells. Generally, but not always, the exclusion dyes bind to DNA, for example via intercalation. Preferably, the exclusion dye does not fluoresce, or fluoresces poorly, in the absence of DNA; this eliminates the need for a wash step. Alternatively, exclusion dyes that require the use of a secondary label may also be used. Preferred exclusion dyes include, but are not limited to, ethidium bromide; ethidium homodimer-1; propidium iodine; SYTOX green nucleic acid stain; Calcein AM, BCECF AM; fluorescein diacetate; TOTO® and TO-PRO™ (from Molecular Probes; supra, see chapter 16) and others known in the art.

Protocols for exclusion dye staining for cell viability are known, see the Molecular Probes catalog, supra. In general, the exclusion dye is added to the cells at a concentration of from about 100 ng/ml to about 500 ng/ml, more preferably, about 500 ng/ml to about 1 µg/ml, and most preferably, from about 0.1 µg/ml to about 5 µg/ml, with about 0.5 µg/ml being particularly preferred. The cells and the exclusion dye are incubated for some period of time, washed, if necessary, and then the cells sorted as outlined below, to remove non-viable cells from the population.

In addition, there are other cell viability assays which may be run, including for example enzymatic assays, which can measure extracellular enzymatic activity of either live cells (i.e. secreted proteases, etc.), or dead cells (i.e. the presence of intracellular enzymes in the media; for example, intracellular proteases, mitochondrial enzymes, etc.). See the Molecular Probes Handbook of Fluorescent Probes and Research Chemicals, Haugland, Sixth Edition, hereby incorporated by reference; see chapter 16 in particular.

In a preferred embodiment, at least one cell viability assay is run, with at least two different cell viability assays being preferred, when the fluors are compatible. When only 1 viability assay is run, a preferred embodiment utilizes light scattering assays (both forward and side scattering). When two viability assays are run, preferred embodiments utilize light scattering and dye exclusion, with light scattering and viability dye staining also possible, and all three being done in some cases as well. Viability assays thus allow the separation of viable cells from non-viable or dying cells.

In addition to a cell viability assay, a preferred embodiment utilizes a cell proliferation assay. By proliferation assay herein is meant an assay that allows the determination that a cell population is either proliferating, i.e. replicating, or not replicating.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook, supra; chapter 15 in particular.

In general, inclusion dyes are provided to the cells at a concentration ranging from about 100 ng/ml to about 5 µg/ml, with from about 500 ng/ml to about 1 µg/ml being preferred. A wash step may or may not be used. In a preferred embodiment, a candidate bioactive agent is combined with the cells as described herein. The cells and the inclusion dye are incubated for some period of time, to allow cell division and thus dye dilution. The length of time will depend on the cell cycle time for the particular cells; in general, at least about 2 cell divisions are preferred, with at least about 3 being particularly preferred and at least about 4 being especially preferred. The cells are then sorted as outlined below, to create populations of cells that are replicating and those that are not. As will be appreciated by those in the art, in some cases, for example when screening for anti-proliferation agents, the bright (i.e. fluorescent) cells are collected; in other embodiments, for example for screening for proliferation agents, the low fluorescence cells are collected. Alterations are determined by measuring the fluorescence at either different time points or in different cell populations, and comparing the determinations to one another or to standards.

In a preferred embodiment, the proliferation assay is an antimetabolite assay. In general, antimetabolite assays find the most use when agents that cause cellular arrest in G1 or G2 resting phase is desired. In an antimetabolite proliferation assay, the use of a toxic antimetabolite that will kill dividing cells will result in survival of only those cells that are not dividing. Suitable antimetabolites include, but are not limited to, standard chemotherapeutic agents such as methotrexate, cisplatin, taxol, hydroxyurea, nucleotide analogs such as AraC, etc. In addition, antimetabolite assays may include the use of genes that cause cell death upon expression.

The concentration at which the antimetabolite is added will depend on the toxicity of the particular antimetabolite, and will be determined as is known in the art. The antimetabolite is added and the cells are generally incubated for some period of time; again, the exact period of time will depend on the characteristics and identity of the antimetabolite as well as the cell cycle time of the particular cell population. Generally, a time sufficient for at least one cell division to occur.

In a preferred embodiment, at least one proliferation assay is run, with more than one being preferred. Thus, a proliferation assay results in a population of proliferating cells and a population of arrested cells. Moreover, other proliferation assays may be used, i.e., colorimetric assays known in the art.

In a preferred embodiment, either after or simultaneously with one or more of the proliferation assays outlined above, at least one cell phase assay is done. A "cell phase" assay determines at which cell phase the cells are arrested, M, G1, S, or G2.

In a preferred embodiment, the cell phase assay is a DNA binding dye assay. Briefly, a DNA binding dye is introduced to the cells, and taken up passively. Once inside the cell, the DNA binding dye binds to DNA, generally by intercalation, although in some cases, the dyes can be either major or minor groove binding compounds. The amount of dye is thus directly correlated to the amount of DNA in the cell, which varies by cell phase; G2 and M phase cells have twice the DNA content of G1 phase cells, and S phase cells have an intermediate amount, depending on-at what point in S phase the cells are. Suitable DNA binding dyes are permeant, and include, but are not limited to, Hoechst 33342 and 33258, acridine orange, 7-AAD, LDS 751, DAPI, and SYTO 16, Molecular Probes Handbook, supra; chapters 8 and 16 in particular.

In general, the DNA binding dyes are added in concentrations ranging from about 1 µg/ml to about 5 µg/ml. The dyes are added to the cells and allowed to incubate for some period of time; the length of time will depend in part on the dye chosen. In one embodiment, measurements are taken immediately after addition of the dye. The cells are then sorted as outlined below, to create populations of cells that contain different amounts of dye, and thus different amounts of DNA; in this way, cells that are replicating are separated from those that are not. As will be appreciated by those in the art, in some cases, for example when screening for anti-proliferation agents, cells with the least fluorescence (and thus a single copy of the genome) can be separated from those that are replicating and thus contain more than a single genome of DNA. Alterations are determined by measuring the fluorescence at either different time points or in different cell populations, and comparing the determinations to one another or to standards.

In a preferred embodiment, the cell phase assay is a cyclin destruction assay. In this embodiment, prior to screening (and generally prior to the introduction of a candidate bioactive agent, as outlined below), a fusion nucleic acid is introduced to the cells. The fusion nucleic acid comprises nucleic acid encoding a cyclin destruction box and a nucleic acid encoding a detectable molecule. "Cyclin destruction boxes" are known in the art and are sequences that cause destruction via the ubiquitination pathway of proteins containing the boxes during particular cell phases. That is, for example, G1 cyclins may be stable during G1 phase but degraded during S phase due to the presence of a G1 cyclin destruction box. Thus, by linking a cyclin destruction box to a detectable molecule, for example green fluorescent protein, the presence or absence of the detectable molecule can serve to identify the cell phase of the cell population. In a preferred embodiment, multiple boxes are used, preferably each with a different fluor, such that detection of the cell phase can occur.

A number of cyclin destruction boxes are known in the art, for example, cyclin A has a destruction box comprising the sequence RTVLGVIGD (SEQ ID NO:48); the destruction box of cyclin B1 comprises the sequence RTALGDIGN (SEQ ID NO:51). See Glotzer et al., Nature 349:132–138 (1991). Other destruction boxes are known as well: YMTVSIIDRFMQDSCVPKKMLQLVGVT (SEQ ID NO:36; rat cyclin B); KFRLLQETMYMTVSIIDRFMQN-SCVPKK (SEQ ID NO:37; mouse cyclin B); RAILID-WLIQVQMKFRLLQETMYMTVS (SEQ ID NO:38; mouse cyclin B1); DRFLQAQLVCRKKLQWGI-TALLLASK (SEQ ID NO:39; mouse cyclin B2); and MSV-LRGKLQLVGTAAMLL (SEQ ID NO:40; mouse cyclin A2).

The nucleic acid encoding the cyclin destruction box is operably linked to nucleic acid encoding a detectable molecule. The fusion proteins are constructed by methods known in the art. For example, the nucleic acids encoding the destruction box is ligated to a nucleic acid encoding a detectable molecule. By "detectable molecule" herein is meant a molecule that allows a cell or compound comprising the detectable molecule to be distinguished from one that does not contain it, i.e., an epitope, sometimes called an antigen TAG, a specific enzyme, or a fluorescent molecule. Preferred fluorescent molecules include but are not limited to green fluorescent protein (GFP), blue fluorescent protein (BFP), yellow fluorescent protein (YFP), red fluorescent protein (RFP), and enzymes including luciferase and β-galactosidase. When antigen TAGs are used, preferred embodiments utilize cell surface antigens. The epitope is preferably any detectable peptide which is not generally found on the cytoplasmic membrane, although in some instances, if the epitope is one normally found on the cells, increases may be detected, although this is generally not preferred. Similarly, enzymatic detectable molecules may also be used; for example, an enzyme that generates a novel or chromogenic product.

Accordingly, the results of sorting after cell phase assays generally result in at least two populations of cells that are in different cell phases.

The proteins and nucleic acids p provided herein n also be used for screening purposes wherein the protein-protein interactions of the BTRXh or NTR proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89 :795 8 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463a preferred system is described in Ser. No. 09/050,863, filed Mar. 30, 1988 and Ser. No. 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding an BTRXh or NTR protein or a portion thereof, and the other encodes a test candidate. Only if the two expression products bind to one another will an indicator, such as a fluorescent protein, be expressed. Expression of the indicator indicates when a test candidate binds to the BTRXh or NTR protein and can be identified as an BTRXh or NTR protein. Using the same system and the identified BTRXh or NTR proteins the reverse can be performed. Namely, the BTRXh or NTR proteins provided herein can be used to identify new baits, or agents which interact with BTRXh or NTR proteins. Additionally, the two-hybrid system can be used wherein a test candidate is added in addition to the bait and the BTRXh or NTR protein encoding nucleic acids to determine agents which interfere with the bait and the BTRXh or NTR protein interactions.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Expression in various cell types, and assays for BTRXh or NTR activity are described above. The activity assays, such as having an effect on, for example, the oxidation/reduction state of a cell or cell component, organelle, or molecule performed to confirm the activity of BTRXh or NTR proteins which have already been identified by their sequence identity/similarity or binding to BTRXh or NTR as well as to further confirm the activity of lead compounds identified as modulators of BTRXh or NTR.

In one embodiment, the BTRXh or NTR proteins of the present invention may be used to generate polyclonal and monoclonal antibodies to BTRXh or NTR proteins, which are useful as described herein. Similarly, the BTRXh or NTR proteins can be coupled, using standard technology, to affinity chromatography columns. These columns may then be used to purify BTRXh or NTR antibodies. In a preferred embodiment, the antibodies are generated to epitopes unique to the NTR protein; that is, the antibodies show little or no cross-reactivity to other proteins. These antibodies find use in a number of applications. For example, the BTRXh or NTR antibodies may be coupled to standard affinity chromatography columns and used to purify BTRXh or NTR proteins as further described below. The antibodies may also be used as blocking polypeptides, as outlined above, since they will specifically bind to the BTRXh or NTR protein.

The anti-NTR protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the BTRXh or NTR protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-Btrxh or anti-NTR protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the BTRXh or NTR protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against NTR protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-NTR protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boemer et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al., Nature 368 856–859 (1994); Morrison, Nature 368, 812–13 (1994); Fishwild et al., Nature Biotechnology 14, 845–51 (1996); Neuberger, Nature Biotechnology 14, 826 (1996); Lonberg and Huszar, Intern. Rev. Immunol. 13 65–93 (1995).

Bispecific antibodies are monoclonal, preferably human or humanized, antibodies that have binding specificities for at least two different antigens. In the present case, one of the binding specificities is for the NTR protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-NTR protein antibodies of the invention have various utilities. For example, anti-NTR protein antibodies may be used in diagnostic assays for a NTR protein, e.g., detecting its expression in specific cells or tissues etc. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-Btrxh or anti-NTR protein antibodies also are useful for the affinity purification of BTRXh or NTR protein from recombinant cell culture or natural sources. In this process, the antibodies against NTR protein are immobilized on a suitable support, such a Sephadex resin or filter paper, using methods well known in the art. The immobilized antibody then is contacted with a sample containing the BTRXh or NTR protein to be purified, and thereafter the support is washed with a suitable solvent that will remove substantially all the material in the sample except the BTRXh or NTR protein, which is bound to the immobilized antibody. Finally, the support is washed with another suitable solvent that will release the BTRXh or NTR protein from the antibody.

III. Use of Plants Expressing Elevated Levels of Thioredoxin and/or NTR

In one embodiment, the transgene protein, for example BTRXh or NTR transgene expressed in plants (see for example U.S. Ser. No. 60/126,736), especially seeds or grains, using the methods described herein, is used in the production and synthesis of BTRXh or NTR. The BTRXh or NTR transgene expressed by the recombinant nucleic acid of the invention may be harvested at any-point after expression of the protein has commenced. When harvesting from the seed or grain or other part of a plant for example, it is not necessary for the seed or grain or other part of the plant to have undergone maturation prior to harvesting. For example, transgene expression may occur prior to seed or grain maturation or may reach optimal levels prior to seed or grain maturation. The transgene protein may be isolated from the seeds or grain, if desired, by conventional protein purification methods. For example, the seed or grain can be milled, then extracted with an aqueous or organic extraction medium, followed by purification of the extracted thioredoxin protein. Alternatively, depending on the nature of the intended use, the transgene protein may be partially purified, or the seed or grain may be used directly without purification of the transgene protein for food processing or other purposes.

The overexpression of the BTRXh or NTR either alone or, preferably in combination, in a seed of grain increases the redox status (SH:SS ratio) of the seed or grain. The combination can be achieved by, for example, breeding plants individually transformed with either BTRXh or NTR, co-transformation with BTRXh and NTR expression vectors, or by mixing the products of the individually transformed plants. In a preferred embodiment, the transgenic seed or grains of the invention find use in the production of food or feed products with increased digestibility, decreased allergenicity, a redistribution of the protein of a seed or grain to the more soluble faction.

For example, the addition of thioredoxin promotes the formation of a protein network that produces flour with enhanced baking quality. Kobrehel et al., (1994) have shown that the addition of thioredoxin to flour of non-glutenous cereal such as rice, maize, and sorghum promotes the formation of a dough-like product. Accordingly, the addition of thioredoxin expressed in seeds using the methods described herein find use in the production of flour with improved baking quality such as increased strength and/or volume.

The enhanced expression of thioredoxin also produces a seed having an altered biochemical composition. For example, enhanced thioredoxin expression produces seed with increased enzymatic activity, such as, increased pullulanase and alpha-amylase A. Enhanced thioredoxin expression also produces seed with early alpha-amylase B activation. Pullulanase ("debranching enzyme") is an enzyme that breaks down branched starch of the endosperm of cereal seeds by hydrolytically cleaving alpha-1,6 bonds. Alpha-amylases break down starch 1–4 linkages. Pullulanase and amylases are enzymes fundamental to the brewing and baking industries. Pullulanase and amylases are required to break down starch in malting and in certain baking procedures carried out in the absence of added sugars or other carbohydrates. Obtaining adequate activity of these enzymes is problematic especially in the malting industry. It has been known for some time that dithiothreitol (DTT, a chemical reductant that reduces and sometimes replaces thioredoxin) activates pullulanase of cereal preparations (e.g., barley, oat, and rice flours). A method of adequately increasing the activity of pullulanase and alpha-amylase A and shortening the activation time of alpha-amylase B with a physiologically acceptable system, leads to more rapid malting methods and, owing to increased sugar availability, to alcoholic beverages such as beers with reduced carbohydrate content.

Accordingly, seeds or grains with enhanced thioredoxin expression provide advantages in the production of malt and beverages produced by a fermentation process. Enhanced pullulanase and alpha-amylase A and earlier induction of alpha-amylase B in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey. Early alpha-amylase B activation would reduce the total time for malting by about 20%. Enhanced fermentation processes also find use in the production of alcohols that are not intended for human consumption, i.e., industrial alcohols.

In another embodiment, seed or grains with enhanced thioredoxin expression provide advantages in enhancing the onset and efficiency of germination.

The overexpression of thioredoxin in seed or grains results in an increase in the total protein. It also promotes the redistribution of proteins to the most soluble albumin/globulin fraction and the production of flour and other food products, feed, and beverages with improved digestibility in comparison to edible products made from non-transformed grains. Such edible products find use in amelioration and treatment of food malabsorptive syndromes, for example, sprue or catarrhal dysentery. Sprue is a malabsorptive syndrome affecting both children and adults, precipitated by the ingestion of gluten-containing foods. Edible products that are more readily digested and readily absorbed avoid or ameliorate the disease symptoms. Edible products with improved digestibility also ameliorate or reduce symptoms associated with celiac disease in which storage proteins that are not readily digested in afflicted individuals result in inflammation of the GI tract.

The expression of thioredoxin in seed grains results in the production of foods and other edible products with reduced allergenicity in comparison to edible products made from non-transformed grains. Food allergies are a significant health and nutrition problem (Lehrer et al., 1996). Up to 2% of adults and 8% of children have a food allergy causing serious symptoms including death. Wheat protein is one of the principal allergens. Food allergies are defined by the American academy of Allergy and Immunology Committee on Adverse Reactions to Food as "an immunological reaction resulting from the ingestion of a food or a food additive" (Fenema, 1996; Lasztity, 1996). Most true allergic responses to food proteins appear to be caused by a type-I immunoglobulin E (IgE)-mediated hypersensitivity reaction (Sicherer, 1999). These responses may occur within minutes or a few hours after eating the offending food (Furlong-Munoz, 1996). When the offending food is ingested by allergy-sensitive individuals the body releases histamines and other biochemicals, resulting in itchy eyes, rash or hives; runny nose; swelling of the lips, tongue, and face; itching or tightness of the throat; abdominal pain; nausea; diarrhea; and shortness of breath. Some individuals have severe, anaphylactic reactions, resulting in approximately 135 deaths per year in the United States. In the U.S. over 2,500 emergency rooms visits per year are allergy-related. There is no cure for food allergies, only avoidance of the food will prevent symptoms. For example, patients with wheat allergy must avoid wheat- or gluten-containing foods; wheat gluten is a very common ingredient in many processed foods (Marx et al., 2000).

A feature common to many allergens is the presence of one or more disulfide bonds that contribute to the resistance of allergens to digestion (Astwood et al., 1996), allowing them to be mostly intact when they react the small intestine where they are presented to mucosal cells that mount an IgE immune response. The major allergens were found to be insoluble storage proteins, gliadins and glutenins.

The soluble storage proteins, albumins and globulins were considerably weaker (Buchanan et al., 1997). Allergenicity of these proteins is substantially decreased after thioredoxin treatment and disulfide bond reduction.

Edible products, for example, bread, cookies, dough, thickeners, beverages, malt, pasta, food additives, including animal feeds, made using the transgenic plants or parts of a transgenic plant of the invention have decreased allergenicity and accordingly can be used to in the treatment of an allergic response. By "treatment" or "alleviating" symptoms herein is meant prevention or decreasing the probability of symptoms.

Increased digestibility of seeds or grains also provides wider consumption of grains by man and animals who otherwise can not consume such grains. For example, sorghum is the world's fifth leading grain in terms of metric tons after wheat, rice, maize, and barley and third in production in the United States after maize and wheat. The use of sorghum is constrained in part because of the difficulty associated with the digestibility of its protein and starch compared to other grains. This difficulty with the digestibility of sorghum protein and starch has to do with the structure of the seed and the manner in which the proteins are associated with the starch. The digestibility of the starch flour from sorghum cultivars is 15–25% lower in digestibility than, for example, maize. Perhaps more notable is the fact that, unlike other grains, the indigestibility of unprocessed sorghum flour increases dramatically after boiling in water, a common practice in Africa. A study with human subjects showed that protein digestibility in cooked sorghum porridge can be as low as 46%, whereas the percent digestibility for cooked wheat, maize, and rice was 81%, 73%, and 66% respectively (Mertz et al. 1984, MacLean et al. 1981). Exogenous addition of reducing agents increases the digestibility of the starch (Hamaker et al. 1987). However, the efficacy of manipulating the thioredoxin system in vivo in the seed by expressing increased amounts of thioredoxin in a manner which does not adversely affect plant development or morphology had rot previously been demonstrated. Accordingly, the transgenic plants of the invention provide wider use of seeds or grains as food sources by increasing the digestibility of the starch and/or protein component. The transgenic seeds or grains of the present invention also provide the advantage of increasing the digestibility of food products for human and feed for animals made of these grains without the addition of exogenous reducing agents. In addition, the increased digestibility results in greater utilization of the food or feed, i.e., a human or animal consuming an edible product comprising a transgenic seed or grain of the invention or an extract thereof more efficiently absorbs nutrients and therefore requires to consume less in comparison to a non-transgenic food product. In another embodiment the transgenic seed, grain or extracts thereof of the present invention and extracts or food products thereof are used as a food or feed additives. For example, an extract or flour or malt produced from a transgenic seed or grain of the invention is added to a non-transgenic food or feed product to improve the digestibility or decrease the allergenicity of the nontransgenic food product or to improve the quality of the total food product, such as, by increasing the strength and/or volume of the food product.

Illustrative embodiments of the invention are described below,

EXAMPLES

Example 1

Barley Gene for Thioredoxin h

Barley thioredoxin h was cloned using PCR with primers derived from the known sequences of two thioredoxin h wheat genes (Gautier et al., 1998). When these two sequences were compared, conserved amino acid regions were found. The following primers were prepared that hybridized to these regions:

wtrh4: 5'-CCAAGAAGTTCCCAGCGTC-3'0 (SEQ ID NO:32)

wtrh2R 5'-CACGCGGCGGCCCAGTAA-3' (SEQ ID NO:58).

These primers were used in an amplification reaction essentially as described by Sambrook et al. (1989). A scutellum barley (*Hordeum vulgare L.*) CDNA library was used as template. The resultant PCR product, corresponding to part of the barley thioredoxin h sequence highly homologous to the wheat cDNAs (FIG. 2), was gel-purified using QIAquick Gel extraction kit (Quiagen, UK) and sequenced using an automated sequencer (Perken Elmer, California, USA). This amplification product was then used to build a gene-specific probe according to a random priming protocol (Promega, Madison, Wis., USA) using $^{32}$P-dCTP. The synthesized probe was purified with a TE Midi Select-D, 650 column (5 Prime-3 Prime, Inc., Colorado, USA), and used to screen the barley scutellum λZapII cDNA library. Plaques were transferred onto nitrocellulose filters (NitroPure, MSI, Westboro, Mass., USA) by standard methods (Sambrook et al, 1989). The DNA was fixed onto the filters using a Stratalinker UV crosslinking apparatus (Stratagene, La Jolla; Calif., USA) and prehybridized for 3.5 hours at 55° C. in a MKII Mini Oven (Hybaid, Woodridge, N.J., USA) using a solution containing 6×SSC, 10 mM EDTA, 5×Denhardt's solution, 0.5% SDS and 100 μg/ml of boiled calf thymus DNA (Sambrook et al., 1989). Hybridization was carried out at 68° C. for 15 hours with 30 μl of the barley thioredoxin h probe-solution per hybridization. Blots were washed twice in 2×SSC, 0.1% SDS at room temperature for 30 minutes, twice in 1×SSC, 0.1% SDS at 65° C. for 30 minutes, and once in 0.1 ×SSC, 0.1% SDS, then exposed to X-ray film at −70° C. with two intensifying screens for 18 hours.

Hybridizing plaques were isolated separately using a Pasteur pipette and resuspended in 500 μl SM (Sambrook et al, 1989) with 20 μl chloroform in an Eppendorf tube. The samples were then vortexed for two minutes and stored at 4° C. overnight. The phage suspension was diluted so that approximately 100 plaques were contained on each 100 mm plate (one cored plaque in 1 ml SM buffer represents about 0.10$^6$ pfu (plaque forming unit(s); *Lambda ZapII Library Instruction Manual*, Stratagene, La Jolla, Calif.). Two positive clones per 20,000 plaque-forming units (pfu) were found. After a second screening purification, the size of the insert in the positive clones was determined using the T3 and T7 primers which hybridize to the extremities of the λ ZapII polylinker site. Two 1.5 kb fragments were obtained. Sequencing revealed that these two clones contained the same full-length thioredoxin h cDNA.

The full-length barley thioredoxin h cDNA is 369 bp (FIG. 2) and encodes a protein of MW 13,165 Daltons (FIG. 1) with a theoretical pI of 5.12. It shares homology with the Arabidopsis and wheat thioredoxin h cDNAs, but is unique in its nucleic and amino acid sequences. The putative corresponding amino acid sequence contains the conserved thioredoxin active site (FIG. 1). The barley amino acid and cDNA sequences are homologous to known wheat thioredoxins h sequences (FIGS. 1 and 2). Nevertheless, the alanine enriched amino-terminal region is shorter in the barley thioredoxin h (by 5 amino acids compared to pTaM1338 (accession number X69915) and by 8 amino acids compared to pTd14132 (accession number AJ001903) (FIG. 1)).

Example 2

Nucleotide Sequence of a cDNA Encoding an NADP-Thioredoxin Reductase (NTR) from Barley (*Hordeum vulgare L.*)

Figure 3:
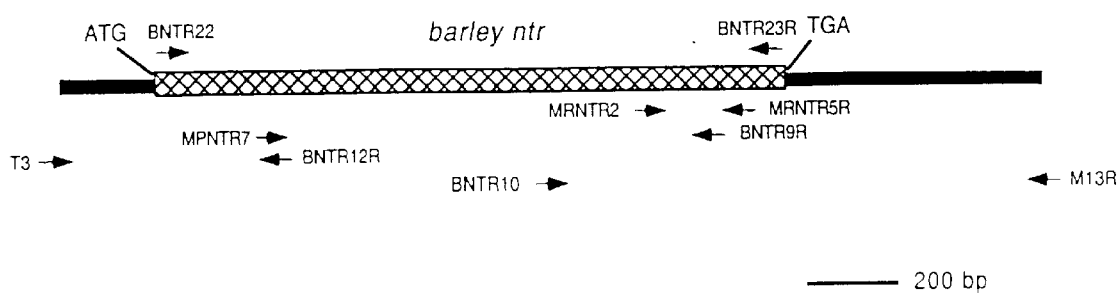
FIG. 3 shows the positions of primers used for PCR amplification to isolate *H. vulgare* NADP-thioredoxin reductase (NTR).

A cDNA library from barley (*Hordeum vulgare L.*, cv. Himalaya) scutellum tissues was constructed by in λ Zap II (Stratagene, La Jolla, Calif.) from poly(A)+RNA. The CDNA library was screened by PCR using a set of degenerate primers, mRNTR2 (5'-TTCTTCGCSATCGGMCAYGARCC-3'; SEQ ID NO:13) plus mRNTR5R (5'-GCGTCSARRGCRGCCATGCASCC-3'; SEQ ID NO:14), producing the internal 201-bp fragment. It was re-screened using a set of primers, MPNTR7 (5'-ACSACSACSACSGACGTSGARAA-3'; SEQ ID NO:15) plus BNTR9R (5'-ACTGGTATGTGTAGAGCCC-3'; SEQ ID NO:16), producing the internal 693-bp fragment (FIG. 3). The sequences of 5'- and 3'-cDNA ends with CDNA library were obtained by PCR using primer sets, T3 (5'-AATTAACCCTCACTAAAGGG-3'; SEQ ID NO:17) plus BNTR12R (5'-AAGTTCTCGACGTCGGTGGTG-3'; SEQ ID NO:18) and M13R (5'-CAGGAAACAGCTATGAC-3'; SEQ ID NO:19) plus BNTR10 (5'-ATTATGCAGGCTAGGGCGCTC-3'; SEQ ID NO:20), respectively. A full-length barley scutellum NTR CDNA clone was amplified by PCR using a primer set, BNTR22 (5'-TATCTAGAATGGAGGGATCCGCCGCGGCGC-3'; SEQ ID NO:21) plus BNTR23R (5'-TTGGTACCTCAATCAGACTTGCCCACCTGT-3'; SEQ ID NO:22), was subcloned into the pAct1INosKmf(−) vector at the XbaI-KpnI sites and the PCR-amplified NTR sequence was then identified by DNA sequencing analysis.

The barley scutellum NTR cDNA clone has an open reading frame (ORF) of 332 amino acids (SEQ ID NO:23) (FIG. 5A–B; Table 1). The calculated molecular weight determined for the translation product of that ORF was 34,900 daltons and the predicted PI is 6.03 (Table 1). The barley scutellum deduced amino acid sequence has 71% similarity with the *A. thaliana* NTR (SEQ ID NO:24) and 39% with *E. coli* NTR (SEQ ID NO:25) (FIG. 4B) using the CLUSTAL-V method set at default parameters (Higgins and Sharp. (1989) Comput. Appl. Biosci., 5(2):151–153). A gene tree analysis suggested that the sequence of *H. vulgare* NTR is more closely related to that of *A. thaliana* NTR than *E. coli* NTR (FIG. 4C).

Figures 5C, 5D:
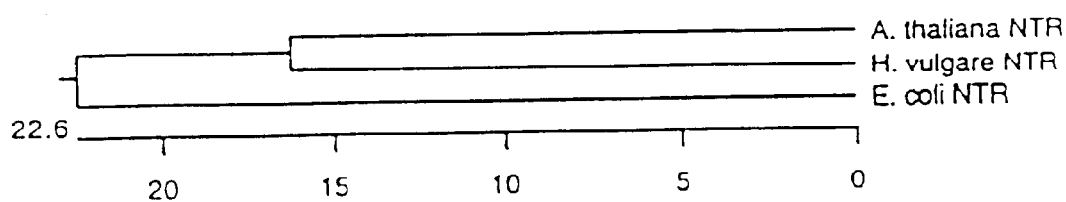

FIGS. 5A and 5B show the nucleotide sequence of the barley scutellum NTR (SEQ ID NO:10) isolated from a cDNA library. At the nucleotide level, *H. vulgare* NTR shows 58% similarity to *A. thaliana* NTR (SEQ ID NO:26) and 41% to *E. coli* NTR (SEQ ID NO:27) (FIG. 5C) as determined by CLUSTAL-V default parameters. Shaded residues in FIG. 5B indicate nucleotide sequences conserved in all three NTR genes from *H. vulgare, A. thaliana* and *E. coli.*

TABLE 1

Predicted Structural Class of the Whole Protein: Alpha Deléage & Roux Modification of Nishikawa and Ooi (1987)

| Analysis | Whole Protein |
|---|---|
| Molecular Weight | 34899.50 m.w. |
| Length | 332 |
| 1 microgram = | 28.654 pMoles |
| Molar Extinction Coefficient | 27910 ± 5% |
| 1 A(280) | 1.25 mg/ml |
| Isoelectric Point | 6.03 |
| Charge ay pH 7 | −4.05 |

| Amino Acid(s) | Number Count | % by Weight | % by Frequency |
|---|---|---|---|
| Whole Protein Composition Analysis: | | | |
| Charged (R, K, H, Y, C, D, E) | 81 | 31.07 | 24.49 |
| Acidic (D, E) | 33 | 11.53 | 9.94 |
| Basic (K, R) | 28 | 11.57 | 8.43 |
| Polar (N, C, Q, S, T, Y) | 80 | 25.05 | 24.10 |
| Hydrophobic (A, I, L, F, W, V) | 127 | 36.67 | 38.25 |
| A Ala | 44 | 8.96 | 13.25 |
| C Cys | 5 | 1.48 | 1.51 |
| D Asp | 17 | 5.61 | 5.12 |
| E Glu | 16 | 5.92 | 4.82 |
| F Phe | 14 | 5.90 | 4.22 |
| G Gly | 37 | 6.05 | 11.14 |
| H His | 7 | 2.75 | 2.11 |
| I Ile | 17 | 5.51 | 5.12 |
| K Lys | 12 | 4.41 | 3.61 |
| L Leu | 19 | 6.16 | 5.72 |
| M Met | 7 | 2.63 | 2.11 |
| N Asn | 11 | 3.60 | 3.31 |
| P Pro | 12 | 3.34 | 3.61 |
| Q Gln | 11 | 4.04 | 3.31 |
| R Arg | 16 | 7.16 | 4.82 |
| S Ser | 21 | 5.24 | 6.33 |
| T Thr | 24 | 6.95 | 7.23 |
| V Val | 30 | 8.52 | 9.04 |
| W Trp | 3 | 1.60 | 0.90 |
| Y Tyr | 8 | 3.74 | 2.41 |
| B Asx | 0 | 0.00 | 0.00 |
| Z Glx | 1 | 0.37 | 0.30 |
| X Xxx | 0 | 0.00 | 0.00 |
| Ter | 0 | 0.00 | 0.00 |

Example 3

Expression of Wheat thioredoxin h (WTRXh) in Transgenic Barley

Figure 6:
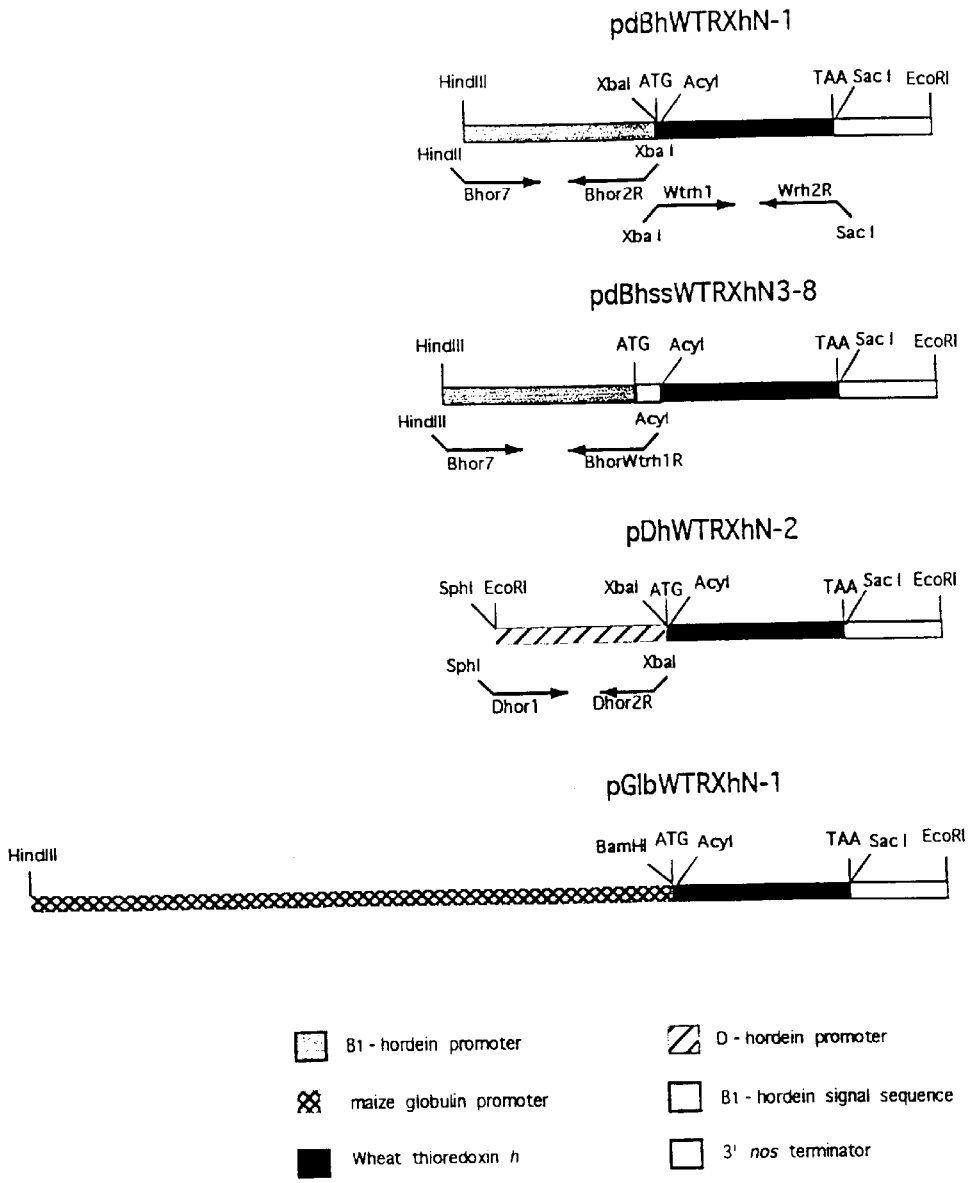
FIG. 6 shows the thioredoxin h constructs used for transformation.

Four different DNA constructs were produced, each containing a 384-bp wtrxh fragment encoding the 13.5-KDa WTRXh protein. The four constructs are illustrated in FIG. 6 and described below. Each construct comprised the 384-bp wtrxh fragment operably linked to a seed-specific promoter (either the barley endosperm-specific D-hordein or B1-hordein promoters or the maize embryo-specific globulin promoter). An additional construct comprised the 384-bp wtrxh fragment operably linked to the B1-hordein promoter and the B1-hordein signal sequence (FIG. 6). The transformation vector used included the bar gene, conferring resistance to bialaphos. Twenty-eight independent regenerable barley lines were obtained after bialaphos selection and all were PCR-positive for the bar gene. The presence of the wtrxh gene was confirmed in the genome of the 28 independent lines by PCR and DNA hybridization analyses. The expression of the WTRXh protein was assessed by western blot analysis, using purified wheat thioredoxin as a control. The WTRXh expressed in transgenic barley had a molecular mass that differed from native barley TRXh but was identical to WTRXh. The WTRXh was found to be highly expressed in developing and mature seed of transgenic barley plants although levels of expression varied among the transgenic events. On average, higher expression levels were observed in lines transformed with the DNA construct containing the B1-hordein promoter plus the signal peptide sequence than the same promoter without the signal peptide sequence. The WTRXh purified from transgenic barley seed was confirmed to be biochemically active.

A. MATERIALS AND METHODS

Plant Materials for Transformation

A two-rowed spring cultivar of barley, Golden Promise, was grown in growth chambers as described previously (Wan and Lemaux 1994; Lemaux et al., 1996).

Construction of Wheat Thioredoxin h Expression Vectors and DNA Sequencing

Expression vectors were constructed containing the wheat thioredoxin h gene (wtrxh) driven by the barley endosperm-specific B1- or D-hordein promoter or the maize embryo-specific globulin promoter.

The plasmids were constructed as follows.
(1) pDhWTRXN-2: A 384-bp wtrxh coding region was amplified by PCR from pTaM13.38 (Gautier et al., 1998). This plasmid contained a cDNA of wtrxh, which was used as a template, creating XbaI and SacI sites with the following primers Wtrxh1 (5'-atatctaga ATGGCGGCGTCGGCGGCGA) (SEQ ID NO:28) and Wtrxh2R (5'-atagagctcTTACTGGGCCGCGTGTAG) (SEQ ID NO:29), respectively (FIG. 6). Small letters in the primer denote a restriction enzyme site for subcloning of the DNA fragment containing the wtrxh gene; underlined letters denote wtrxh sequences. The ATG initiation codon for wtrxh expression was included in the Wtrxh1 primer. PCR reactions were performed on a thermocycler (MJ Research Inc., Watertown, Mass.) using recombinant Taq DNA polymerase (Promega. Madison, Wis.) in a 100-µl reaction volume. The reaction buffer contained 10 mM Tris-HCl (pH 9.0), 50 mM KCl, 1.5 mM MgCl$_2$, 0.1% Triton-X-100, and 50 µM of each deoxyribonucleoside triphosphate. PCR conditions utilized 25 cycles of 94° C. for 1 min, 55° C. for 1 min and 72° C. for 2 min, with a final extension step at 72° C. for 7 min. The wtrxh fragment, which was amplified with the primers Wtrxh1 and Wtrxh2R, was purified from a 0.7% agarose gel using a QIAquick® gel extraction kit (Qiagen Inc., Chatsworth, Calif.), digested with XbaI and SacI and ligated into XbaI/SacI-digested pUC19 to generate the pWTRXh-1 plasmid. Nucleotide sequences of the PCR-amplified wtrxh coding region fragment were determined by the dideoxynucleotide chain termination method using Sequenase according to manufacturer's instructions (United States Biochemical, Cleveland, Ohio) with double-stranded plasmid templates and regularly spaced primers.

pDhWTRXN-2 was made by replacing the uidA gene in pDhGN-2 (containing barley endosperm-specific D-hordein promoter (FIG. 12) and nos 3'terminator) with the XbaI/SacI fragment containing the wtrxh coding sequence from pWTRXh-I, which contains the PCR-amplified wtrxh coding sequence in pUC19. To construct pDhGN-2, a 0.4-kb D-hordein promoter was amplified by PCR from pDII-Hor3 (Sørenson et al., 1989, 1996; Cho et al., 1999a). This plasmid contained the D-hordein promoter sequence, which was used as a template, creating SphI and XbaI sites with the following primers: Dhor1 (5'-ggcgcatgcgaattc GAATTCGATATCGATCTTCGA-3') (SEQ ID NO:30) and Dhor2 (5'-aactctagaCTCGGTGGACTGTCAATG-3') (SEQ ID NO:31), respectively. Small letters in the primers contain restriction enzyme sites for subcloning of the DNA fragment containing the D-hordein promtoer; underlined letters denote D-hordein promoter sequences. The PCR amplified D-hordein promoter fragment was digested with SphI and XbaI and replaced with the cauliflower mosaic 35S (CaMV 35S) promoter in p35SGN-3 to generate the pDhGN-2 plasmid. p35SGN-3 was made by ligating the 3.0-kb SphI-EcoRI fragment containing the CaMV 35S promoter, uidA (beta-glucuronidase, gus) gene and nos into the SphI/EcoRI-digested pUC18.

(2) pdBhWTRX-1: The construction of pdBhWTRXN-1 started by using pBhWTRXN-1. pBhWTRXN-1 was made by replacing the uidA gene in pBhGN-1, which contains uidA driven by the barley endosperm-specific B1-hordein promoter and terminated by the nos 3' terminator, with the XbaI/SacI fragment from pWTRXh-1, which contains the wtrxh coding sequence. The 120-bp HindIII-5' B1-hordein flanking region was deleted from the pBhWTRXN-1 and religated to make the pdBhWTRXN-1 construct.

(3) pdBhssWTRXN3-8: Primers Bhor7 (5'-GTAAAGCITTAACAACCCACACATTG) (SEQ ID NO:7) and BhorWtrxh1R (5'-CCGACGCCGCTGCAATCGTACTTGTTGCCGCAAT) (SEQ ID NO:8) containing HindIII and Acyl sites, respectively, were used for amplification of a 0.49-kb B1-hordein 5'-region, which included the B1-hordein signal peptide sequence (FIG. 11). A λ2-4/HindIII plasmid containing a genomic clone of B1-hordein (Brandt et al., 1985; Cho and Lemaux, 1997) was used as a template for the amplification. The primer BhorWtrxh1R is an overlapping primer, which contains the wtrxh coding sequence (underlined) and a partial signal peptide sequence from the B1-hordein promoter, but lacks the ATG initiation codon for wtrxh. pdBhssWTRXN3-8 was made by replacing the D-hordein promoter (FIG. 6) in pDhWTRXN-2 with the 0.49-kb PCR-amplified HindIII/Acyl fragment, which contains the B1-hordein promoter, its signal peptide sequence and the junction region from the 5' trxh gene. Thus, construct pdBhssWTRXN3-8 contains the barley endosperm-specific B1-hordein promoter with its signal peptide sequence (FIG. 6), wtrxh, and nos (FIG. 6). The signal peptide sequence containing the ATG initiation codon was directly combined with the sequence of wtrxh, with no extra amino acid sequences being introduced between the two. This ensures that the WTRXh protein has a precise cleavage site in the lumen of the endoplasmic reticulum (ER). The authenticity of a PCR-amplified fragment from the chimeric product was confirmed by DNA sequencing.

(4) pGIb1WTRXN-1: The 1.42-kb HindIII/BamHI fragment containing the maize embryo-specific globulin promoter from the ppGIb1GUS plasmid (Liu and Kriz, 1996) was ligated into pBluescript II KS(+) to create HindIII and XbaI sites. pGIbWTRXN-1 was made by (restricting pDhWTRXN-2 with HindIII and XbaI in order to remove the 0.49-kb HindIII/XbaI barley D-hordein promoter from the pDhWTRXN-2. In place of the 0.49-kb HindIII/XbaI D-hordein promoter fragment (FIG. 6), the 1.42-kb HindIII/XbaI maize globulin promoter was ligated into the HindIII/XbaI digested pDhWTRXN-2 to form the pGIbWTRXN-1 plasmid.

Stable Barley Transformation

Stable transgenic lines of barley expressing WTRXh driven by the B1-hordein promoter with and without the signal peptide sequence (FIG. 11 SEQ ID NO:11), by the D-hordein promoter (FIG. 12 SEQ ID NO:12) and by the maize globulin promoter were obtained following modifications of published protocols (Wan and Lemaux 1994; Lemaux et al., 1996; Cho et al., 1998a–c). Whole immature embryos (IEs) (1.0–2.5 mm) were aseptically removed, placed scutellum-side down on DC callus-induction medium containing 2.5 mg/L 2,4-D and 5 $\mu$M CuSO$_4$ (Cho et al., 1998a–c). One day after incubation at 24±1° C. in the dark, the IEs were transferred scutellum-side up to DC medium containing equimolar amounts of mannitol and sorbitol to give a final concentration of 0.4 M. Four hours after treatment with the osmoticum, the IEs were used for bombardment Gold particles (1.0 $\mu$m) were coated with 25 pg of a 1:1 molar ratio of pAHC20 (Christensen and Quail, 1996) and one of the following plasmids, pdBhWTRXN-1, pdBhssWTRXN3-8, pDhWTRXN-2 and pGIbWTRXN-1. The microprojectiles were bombarded using a PDS-1000 He biolistic device (Bio-Rad, Inc., Hercules, Calif.) at 1100 psi. Bombarded IEs were selected on DC medium with 5 mg/L bialaphos for 2 to 3 months. Bialaphos-resistant callus was transferred onto an intermediate culturing medium (DBC2; Cho et al., 1998a–c), containing 2.5 mg/L 2,4-D, 0.1 mg/L BAP and 5.0 $\mu$M CuSO4, between the selection [DC medium plus bialaphos (Meiji Seika Kaisha, Ltd., Yokohama, Japan)] and regeneration (FHG medium; Hunter, 1988) steps. The culturing after callus induction and selection on DC medium were carried out under dim light conditions (approximately 10 to 30 $\mu$E, 16 h-light) (Cho et al., 1998a–c). Regenerated shoots were transferred to Magenta boxes containing rooting medium (callus-induction medium without phytohormones) containing 3 mg/L bialaphos. When shoots reached the top of the box, plantlets were transferred to soil in the greenhouse.

Cytological Analysis

For cytological analysis of transgenic barley plants, healthy root meristems were collected from young plants grown in the greenhouse. After pre-treatment at 4° C. in saturated 1-bromonaphthalene solution overnight, root meristems were fixed in 1:3 glacial acetic acid:ethanol and stored at 4° C. Root meristems were hydrolyzed in 1 M HCl at 60° C. for 5–7 min, stained in Feulgen solution and squashed on a glass slide in a drop of 1% aceto-carmine. Chromosomes were counted from at least five well-spread cells per plant.

Herbicide Application

To determine herbicide sensitivity of To plants and their progeny, a section of leaf blade at the 4- to 5-leaf stage was painted using a cotton swab with 0.25% (v/v) Basta™ solution (starting concentration 200 g/L phophinothricin, Hoechst AG, Frankfurt, Germany) plus 0.1% Tween 20. Plants were scored 1 week after herbicide application.

Polymerase Chain Reaction (PCR) and DNA Blot Hybridization

Total genomic DNA from leaf tissues was purified as described by Dellaporta (1993). To test for the presence of wtrxh in genomic DNA of putatively transformed lines, 250 ng of genomic DNA was amplified by PCR using one of two primer sets:

Set 1:

Wtrxh1 (5'-ATATCTAGAATGGCGGCGTCGGCGGCGA) (SEQ ID NO:28) and

Wtrxh2R (5'-ATAGAGCTCTTACTGGGCCGCGTGTAG) (SEQ ID NO:29); or

Set 2:

Wtrxh4 (5'-CCAAGAAGTTCCCAGCTGC) (SEQ ID NO:32) and

Wtrxh5R (5'-ATAGCTGCGACAACCCTGTCCTT) (SEQ ID NO:33).

The presence of bar was determined using the primer set:

BAR5F (5'-CATCGAGACAAGCACGGTCAACTTC3') (SEQ ID NO:34) and

BAR1R (5'-ATATCCGAGCGCCTCGTGCATGCG) (SEQ ID NO:35) (Lemaux et al., 1996).

Amplifications were performed with Taq DNA polymerase (Promega, Madison, Wis.) in a 25-μl reaction (Cho et al., 1998a–c). Twenty-five microliters of the PCR product with loading dye were subjected to electrophoresis in a 1.0% agarose gel with ethidium bromide and photographed using exposure to UV light. Presence of 0.4- and 0.14-kb fragments was consistent with intact and truncated wtrxh fragments, respectively; an internal 0.34-kb fragment was produced from the bar gene with bar primers. Homozygous lines for wtrxh were screened by PCR and western blot analysis in $T_2$ or $T_3$ plants.

For DNA hybridization analysis, 10 μg of total genomic DNA from leaf tissue of each line was digested with HindIII and SacI, separated on a 1.0% agarose gel, transferred to Zeta-Probe GT membrane (Bio-Rad, Hercules, Calif.) and hybridized with a radiolabeled wtrxh-specific probe following the manufacturer's instructions. The wtrxh-containing 0.4 kb XbaI-SacI fragment from pDhWTRXN-9 was purified by QIAEX gel extraction kit (QIAGEN, Chatsworth, Calif.) and labeled with $^{32}$P-dCTP using random primers.

Western Blot Analysis

Western blot analysis was performed on seeds from selected transgenic lines as well as from control barley seeds from non-transgenic Golden Promise grown under the same conditions as the transgenic plants and from control wheat seeds of a durum wheat cultivar, cv. Monroe, or a bread wheat cultivar cv. Capitale. Whole seeds were ground to a fine powder with a mortar and pestle under liquid nitrogen. Ten to 20 seeds were used for each sample; the volume-of extraction buffer (50 mM Tris HCl or phosphate buffer, pH 7.8, 0.5 mM phenylmethyl sulfonyl fluoride [PMSF], 1 mM EDTA) varied from 2 to 4 ml depending on the number of seeds used and the viscosity of the extract. Grinding was continued for an additional minute after buffer addition; the mixture was then centrifuged at 14,000×g for 10 minutes and the supernatant solution was saved as the albumin-globulin fraction that contained the thioredoxin.

SDS-PAGE of the albumin-globulin fraction was performed in 12–17% polyacrylamide gradient gels at pH 8.5 (Laemmli, 1970). From each sample equal amounts of protein (~40 μg) quantitated according to Bradford (1976) were diluted 1:2 v/v in Laemmli sample buffer, boiled for 3 minutes, loaded onto gels and subjected to electrophoresis at a constant current of 15 mA. Proteins were transferred to nitrocellulose at a constant voltage of 40 V for 4 hours at 4° C. using a Hoefer Transphor Transfer Unit (Alameda, Calif.). Nitrocellulose was blocked with 5% powdered milk in TBS for 2 hours at room temperature (RT), incubated in primary antibody for 4 hours at RT and in secondary antibody for 1 hour at RT. Primary antibody was wheat anti-thioredoxin h II Ab (Johnson et al., 1987b) diluted 1 to 500; secondary antibody was goat anti-rabbit alkaline phosphatase (Bio-Rad, Hercules Calif.) diluted 1:3000. Blots were developed in NBT/BCIP alkaline phosphatase color reagent (according to Bio-Rad instructions); gels were stained with Coomassie blue to assure transfer. Images were scanned using a Bio-Rad GelDoc 1000 (Hercules, Calif.) and analyzed using Bio-Rad Multi Analyst, version 1.0.2. All bands were scanned over the same area, using a rectangle of comparable density as background; results were expressed as % of volume scanned. The number shown represents the percent of the total volume (pixel density× area of scanned band).

WTRXh Activity Measurements

Preparation of Materials for Extraction

Mature grains from various heterozygous and homozygous transgenic lines served as starting materials for the assay. Heterozygous lines with a D-hordein promoter were: GPDhBarWtrx-5, GPDhBarWtrx-9-1, and GPDhBarWtrx-9-2. Heterozygous lines with a B-hordein promoter and no signal sequence were: GPdBhBarWtrx-2, -5, -9, -19 and GPdBhBarWtrx-20. Heterozygous lines with a B-hordein promoter plus a signal sequence were: GPdBhssBarWtrx-2, -7, GPdBhssBarWtrx-29, GPdBhssBarWtrx-20, GPdBhssBarWtrx-14, GPdBhssBarWtrx-22. Homozygous lines with a signal sequence were: GPdBhssBarWtrx-2-17, GPdBhssBarWtrx-2-17-1, GPdBhssBarWtrx-29-3 and GPdBhssBarWtrx-29-3-2. Control materials included a non-transformed tissue culture derived line, 4-96, a transformed line containing only bar, GPBar-I, and null segregant lines, GPdBhssBarWtrx-29-11 and GPdBhssBarWtrx-29-11-10, derived from line GPdBhssBarWtrx-29.

Preparation of $(NH_4)_2SO_4$ Extracts for Gel Filtration

Approximately fifteen grams of barley grains were ground to powder in a coffee grinder and extracted with 80 ml (1:4 w/v) of buffer [(50 mM Tris-HCl buffer, pH 7.9, 1 mM EDTA, 0.5 mM PMSF (phenylmethysulfonyl fluoride)], 2 mM e-amino-n caproic acid, 2 mM benzamidine-HCl) by stirring for 3 hrs at 4° C. The slurry plus the rinse was subjected to centrifugation at 25,400×g for 20 min, the supernatant solution was decanted through glass wool, pellets were resuspended in a small volume of buffer and then clarified by centrifugation as before. The supernatant fractions were combined, an aliquot was removed and the remainder was subjected to acidification by adjusting the pH from 7.83 to 4.80 with 2 N formic acid; denatured proteins were removed by centrifugation as above prior to assay. The pH of the acidified supernatant solution was readjusted to 7.91 with 2 N $NH_4OH$ and an aliquot was removed for assay. Powdered $(NH_4)_2SO_4$ was added to a final concentration of 30% and the sample was stirred for 20 min at 4° C., followed by centrifugation as described above. The pellet was discarded. Additional $(NH_4)_2SO_4$ was added to bring the decanted supernatant solution to 90% saturation; the sample was stirred for 16 hrs at 4° C., followed by centrifugation as described above.

The supernatant solution was discarded, the 30–90% $(NH_4)_2SO_4$ pellets were re-suspended in 30 mM Tris-HCl, pH 7.9 buffer and then subjected to centrifugation at 40,000×g for 15 min to clarify. The resulting supernatant (30–90% (NH$_4$)$_2$SO$_4$ fraction) was added to dialysis tubing (6,000–8,000 MW cut-off) and exposed to solid sucrose at 4° C. to obtain a 10-fold reduction in volume. An aliquot (1 ml) of the clarified and concentrated 30–90% (NH$_4$)$_2$SO$_4$) sample was saved and the remaining sample was applied to a pre-equilibrated (30 mM Tris-HCl, pH 7.9, 200 mM NaCl) Sephadex G-50 superfine column (2.5×90 cm; ~400 mL bed volume) with a peristaltic pump at a flow rate of 0.5 mL/min. Protein was eluted with the same buffer at the same flow rate; one hundred fifty drop-fractions were collected. Selected fractions were used to measure absorbance at 280 nm using a Pharmacia Biotech Ultrospec 4000 and to assay for TRXh activity following the NADP-MDH activation protocol (see below). Active fractions were pooled, stored at 4° C., and then assayed for total NADP-MDH activation activity.

Preparation of Heat-treated Extracts

Approximately 10 grams of barley grains were ground to powder for about 30 sec in a coffee grinder and extracted by shaking for 1 hr at room temperature in 50 mL buffer as above. The slurry plus the rinse was subjected to centrifugation at 27,000×g for 20 min and the supernatant solution decanted through glass wool. A 20 mL aliquot of each sample was heated at 65° C. until sample temperature reached 60±1° C. (~10 min). The sample was held at 60° C. for 10 additional min, followed by cooling in an ice/water bath. The cooled sample was centrifuged and the supernatant solution was concentrated by sucrose as above and stored at −20° C. Frozen samples were thawed and clarified by centrifugation at 14,000 rpm for 10 min at 4° C. Total TRXh activity was estimated on the concentrated, supernatant fractions.

NADP-malate Dehydrogenase Activation Assay

Thioredoxin h activity was assayed as previously described (Florencio et al., 1988; Johnson et al., 1987a). Fifty to 120 µl of extract (depending on activity) was preincubated with DTT, and 0.16 to 0.32 µl of the pre-incubation mixture was used for the NADP-MDH assay. Control assays were conducted on identical fractions in the absence of NADP-MDH. Western blot analysis was conducted as described above except that 10 to 20% SDS-polyacrylamide gels were used for electrophoresis and transfer to nitrocellulose paper was for 4 hrs at 40 V.

Sequential Extraction of Multiple Protein Fractions

Ten grams of barley grain were sequentially extracted for albumin (H$_2$O-soluble), globulin (salt-soluble), hordeins (alcohol-soluble) and glutelins (Shewry et al., 1980). Barley powder was stirred with 0.5 M NaCl for 1 h at 25° C. to remove salt-soluble proteins. Two sequential hordein fractions were extracted from the residue with 50% propanol in the absence (hordein-I) and presence (hordein-II) of 2% (v/v) 2-mercaptoethanol. Glutelins were extracted from the residue with 0.05 M borate buffer, pH 10, containing 1% (v/v) 2-mercaptoethanol and 1% (v/v) sodium dodecylsulphate.

In vitro Monobromobimane (mBBr) Labeling of Proteins

Immature, mature, or germinating seeds from nontransformed and transgenic plants were ground in 100 mM Tris-HCl buffer, pH 7.9. Reactions were carried out following the protocol of Kobrehel et al., (1992). Seventy microliters of the buffer mixture containing a known amount of protein was either untreated or treated with DTT to a final concentration of 0.5 mM. After incubation for 20 min, 100 nmol of mBBr was added, and the reaction was continued for another 15 min. To stop the reaction and derivatize excess mBBr, 10 µl of 10% SDS and 100 µl of 100 mM 2-mercaptoethanol were added. The samples were applied to a 15% SDS-PAGE gel. Fluorescence of mBBr was visualized by placing gels on a light box filtered with a UV light source (365 nm). Protein determination was carried out by the Bradford dye binding method (Bradford 1976) using bovine serum albumin or gamma globulin as standards.

Assay of Pullulanase and its Inhibitor

To measure pullulanase activity, grain was germinated in a dark chamber and retained for up to 5 days at 25° C. as described (Kobrehel et al., 1992; Lozano et al., 1996.). A set of plates from each line was removed for extract preparation each day. Cell-free endosperm extracts were prepared from lots of 10–20 germinated grains of equivalent root and coleoptile length within a given cohort. Endosperm was separated from the embryo and other tissues and added to Tris-HCl buffer (50 mM, pH 7.9) supplemented with 1 mM EDTA and 0.5 mM PMSF (1:3 to 1:6, wt/vol ratio of tissue to buffer depending on developmental stage). After grinding in a mortar on ice, the sample was clarified by centrifugation (10 min at 24,000×g); the supernatant fraction was recovered and stored in 0.5-ml aliquots −80° C. for pullulanase spectrophotometric or gel assays.

Pullulanase activity was determined spectrophotometrically at 37° C. by measuring dye released after 30 min at 534 nm using red pullulan (Megazyme, Bray, Ireland) as substrate in 50 mM citrate-phosphate buffer (pH 5.2) (Serre et al., 1990.). Pullulanase also was assayed on native activity gels of 7.5% acrylamide, 1.5 mm thickness, containing 1% red pullulan (Furegon et al., 1994.). Gels were scanned using a Bio-Rad Gel Doc 1000 and analyzed using Bio-Rad MULTI ANALYST, version 1.0.2. Pullulanase inhibitor activity was determined on fractions heated to inactivate pullulanase (70° C. for 15 min) by measuring their ability to inhibit added purified barley malt pullulanase. Endogenous pullulanase activity was shown to be completely eliminated by this heat-treatment while the inhibitor activity was not affected (Macri et al., 1993; MacGregor et al., 1994).

Alpha-amylase Activity in Barley Grain Overexpressing Thioredoxin h

Amylase activity from the null segregant and homozygous barley grains was analyzed during germination and early seedling growth by using gels containing starch. Native polyacrylamide electrophoresis gels [6% acrylamide, 1.5 mm thick] were prepared and developed according to the method of Laemmli (1970) except that SDS was omitted from all solutions. The separating gel contained 0.5% soluble starch (Lintner potato starch, Sigma Chemical Co., St. Louis, Mo.). Lyophilized samples were dissolved in distilled H$_2$O and mixed 1:1 with a buffer consisting of 0.25 M Tris-HCl, pH 6.8, 50% glycerol, 0.04% bromophenol blue, and 3 mM CaCl$_2$. Fifty micrograms of sample protein were loaded in each lane. Electrophoresis was carried out at 80 milliamps per gel at 4° C. until the dye front was at the edge of the gel (usually 4 to 5 hours). After electrophoresis, the gels were incubated in 100 ml of 0.1 M succinate buffer, pH 6.0, for 1–2 hours at 37° C. The gels were then stained for 5 min in a solution containing 2.5 mM I$_2$ and 0.5 M KI. Gels were washed in distilled H$_2$O. Except for the white regions containing amylase activity, gels were stained dark blue.

Isoelectricfocusing (IEF)

For determination of alpha-amylase isozyme patterns, extracts from both dry and germinating grain of transformed and control (untransformed) barley were separated by electrophoresis at 4° C. [1.0 mm thick, pH 3–10 isoelectric focusing (IEF) polyacrylamide gels, using the X cell II system (NOVEX, San Diego, Calif.)]. Cathode buffer contained 20 mM arginine, and 20 mM lysine; anode buffer was 7 mM phosphoric acid. Samples were mixed 1:1 and 2×IEF sample buffer pH 3–10 (NOVEX). After sample application (20 μg/lane) gels were developed at constant voltage [100 V for 1 hr, 200 V for an additional 1 hr, and 500 V for 30 min]. IEF standards (Bio-Rad) were used to determine the pH gradient of the gels.

Multiple Antibody Probing of IEF Gels

Western blot analysis of alpha-amylase isozymes was performed using a Mini Trans-Blot Electrophoretic Transfer Cell (Bio-Rad). Seed extracts from the null segregant and homozygous lines overexpressing wheat thioredoxin h were separated by IEF gels as described above. Proteins were transferred to nitrocellulose at a constant voltage of 100 V for 1 hr at 4° C. using 0.75% acetic acid as blotting buffer. Nitrocellulose was blocked with 5% powdered milk in Tris buffer solution (20 mM Tris-HCl, pH 7.5, supplemented with 0.15 M NaCl) for 1 hr at room temperature, incubated with primary antibody for 4 hours at room temperature and then with secondary antibody for 1 hour at room temperature. Primary antibody was anti-barley alpha-amylase B diluted 1:1000; secondary antibody was goat anti-rabbit alkaline phosphatase (Bio-Rad) diluted 1:3000. Blots were developed in NBT/BCIP alkaline phosphatase color reagent (according to Bio-Rad instructions) thereby rendering the cross-reacted alpha-amylase bluish-purple. To achieve full identity of isozyme pattern, blots were probed a second time with another primary antibody, anti-alpha-amylase A (diluted 1:1000) and the secondary antibody (as above). This time blots were developed in Naphthol Phosphate/Fast Red alkaline phosphatase color reagent (according to Bio-Rad instructions) which gave a pink stain to the alpha-amylase A. The blot shown was subject to this dual probing procedure.

B. RESULTS AND DISCUSSION

Production of Transgenic Plants

One day after bombardment, the whole embryos were transferred onto DC medium with 5 mg/L bialaphos. At transfer to the second selection plate (5 mg/L bialaphos), all material from individual callusing embryos was broken into small pieces (24 mm) using forceps and maintained separately. During the subsequent two to five selection passages on 5 mg/L bialaphos (at 10–20 d intervals). callus pieces showing evidence of more vigorous growth were transferred to new selection plates. During the second round of selection, some pieces of callus were inhibited in growth and in some cases pieces turned brown. In general, transformed tissues were observed after three or more rounds of selection. The bialaphos-resistant tissues were transferred onto an intermediate medium, DBC2 or DBC3 (Cho et al., 1998a–c) with bialaphos (5mg/L), and grown for 1 to 2 months before regeneration on FHG medium containing 3 mg/L bialaphos. Green plantlets were transferred into Magenta boxes containing 3 mg/L bialaphos. Twenty-eight independent putatively transformed, regenerable lines were produced after bialaphos selection (shown in Table 2).

TABLE 2

Transgenic Barley Lines Transformed with Wheat Thioredoxin h Gene.

| Plasmids for Bombardment | Transgenic Barley Line | DNA PCR $T_0$ leaf) bar | wtrxh | TRXh Expression in $T_1$ seeds | Ploidy | Comments |
|---|---|---|---|---|---|---|
| pdBhWTRXN-1 + pAHC20 | GPdBhBarWTRX-1 | + | + | n.d. | Tetraploid | |
| | GPdBhBarWTRX-2 | + | + | + | Tetraploid | |
| | GPdBhBarWTRX-3 | + | + | + | Diploid | |
| | GPdBhBarWTRX-5 | + | + | + | Tetraploid | Sterile |
| | GPdBhBarWTRX-16 | + | − | n.d. | Tetraploid | |
| | GPdBhBarWTRX-17 | + | + | n.d. | Tetraploid | |
| | GPdBhBarWTRX-19 | + | + | + | Diploid | |
| | GPdBhBarWTRX-20 | + | + | + | Diploid | |
| | GPdBhBarWTRX-22 | + | + | + | Diploid | |
| | GPdBhBarWTRX-23 | + | + | + | Diploid | − |
| pdBhssWTRXN3-8 + pAHC20 | GPdBhssBarWTRX-1 | + | − | − | Diploid | |
| | GpdBhssBarWTRX-2 | + | + | + | Diploid | Homozygous |
| | GPdBhssBarWTRX-3 | + | + | − | Diploid | |
| | GPdBhssBarWTRX-7 | + | + | + | Diploid | |
| | GPdBhssBarWTRX-9 | + | + | n.d. | Tetraploid | |
| | GpdBhssBarWTRX-11 | + | + | − | Diploid | |
| | GPdBhssBarWTRX-13 | + | + | + | Tetraploid | |
| | GPdBhssBarWTRX-14 | + | + | + | Diploid | |
| | GPdBhssBarWTRX-20 | + | + | + | Tetraploid | |
| | GPdBhssBarWTRX-21 | + | + | n.d. | Tetraploid | Sterile |
| | GPdBhssBarWTRX-22 | + | + | + | Tetraploid | |
| | GPdBhssBarWTRX-29 | + | + | + | Diploid | Homozygous |
| pDhWTRXN-2 + pAHC20 | GPDhBarWTRX-5 | + | + | + | Tetraploid | |
| | GPDhBarWTRX-7 | + | + | + | Diploid | |
| | GPDhBarWTRX-8 | + | + | + | Diploid | |
| | GPDBhBarWTRX-9 | + | + | + | Diploid | Homozygous |
| | GPDBhBarWTRX-22 | + | + | + | Diploid | Sterile |
| pGIbWTRXN-1 + pAHC20 | GPGIbBarWTRX-1 | + | + | + | Diploid | |

*n.d.: not determined

Analysis of $T_0$ Plants and Their Progeny

PCR analysis was performed using two sets of WTRXh primers and one set of BAR primers (see FIG. 6). PCR amplification resulted in 0.4-kb intact wtrxh or 0.14kb truncated wtrxh and 0.34-kb internal bar fragments from transgenic lines. Of the 28 lines tested, 28 yielded bar fragments from $T_0$ leaf tissue and 26 produced PCR-amplified fragments for wtrxh, giving a 93% co-transformation frequency. Nine lines were transformed with pdBhWTRXN-1, eleven with pdBhssWTRXN-8, five with pDhWTRXN-2 and one with pG1bWTRXN-1 (see Table 2). Three lines (GPdBhBarWtrx-5, GPdBhssBarWtrx-21 and GPDhBarWtrx-22) were sterile. Seeds of $T_1$ plants and their progeny from selected wtrxh-positive lines were planted in order to screen for homozygous lines. Homozygous lines and null segregants were obtained from GPdBhssBarWtrx-2, -29 and GPDhBarWtrx-9 (see Table 2).

Cytological Analysis of Transgenic Plants

Chromosomes were counted in root meristem cells of independently transformed To barley plants. Out of 28 independent transgenic lines examined, 17 lines had the normal diploid chromosome complement (2n=2x=14), while the remaining 11 lines were tetraploid (2n=4x=28) (see Table 2).

Characterzation and Content of WTRXh Produced in Transgenic Seed

As discussed above, several stably transformed barley lines were obtained that express wheat thioredoxin h. As seen in FIG. 7, the stable introduction of the wtrxh linked to the B1-hordein promoter with the signal peptide sequence resulted in greatly enhanced expression of active WTRXh in transgenic barley seed.

Analysis by western blot of soluble protein fractions of the three lines in which the thioredoxin gene was linked to a signal sequence (GPdBhssBarWtrx-22, GPdBhssBarWtrx-29 and GPdBhssBarWtrx-7) showed differences in the level of expression (shown in Table 3). Line GPdBhssBarWtrx-22, GPdBhssBarWtrx-29 and GPdBhssBarWtrx-7, respectively, showed 22 times, 10 times and 5.5 times more WTRXh protein than nontransformed control seeds. The analyses showed that the thioredoxin content of the null segregant (GPdBhssBarWtrx-29-11) was approximately half that of the corresponding control. The three lines generated from the construct in which the thioredoxin-gene was not associated with a signal sequence were also compared to nontransformed control barley seed and they exhibited the following increases in TRXh levels as indicated by the western blot analyses: GPDhBarWtrx-9: 12 times; GPDhBarWtrx-5: 6.3 times; GPdBhBarWtrx-2: 6.4 times. When probed on Western Blots, the transgenic lines show two bands while the control barley generally shows only one and in some cases a second minor band. Furthermore, the tissues from the transgenic lines were characterized by a band that did not correspond to either of the barley bands but did correspond to wheat thioredoxin h. These data indicate that the protein introduced by transformation is wheat thioredoxin h.

TABLE 3

Western Blot Analyses of Overexpression of Wheat Thioredoxin h in Barley.

| Barley Line | % Volume Scanned | Fold Increase (or Decrease) |
| --- | --- | --- |
| Non-Transformed Control: | | |
| Golden Promise | 1.46 | 1.0 |
| Transformed with Signal Sequence: | | |
| GPdBhssBarWtrx-22 | 32.44 | 22 |
| GpdBhssBarWtrx-29 | 14.62 | 10 |
| GpdBhssBarWtrx-7 | 7.99 | 5.5 |
| Transformed without Signal Sequence: | | |
| GPDhBarWtrx-9 | 17.69 | 12 |
| GPDhBarWtrx-5 | 9.20 | 6.3 |
| GPdBhBarWtrx-2 | 9.29 | 6.4 |
| Null Segregant: | | |
| GPdBhssBarWtrx-29-11-10 | 0.93 | (0.64) |

The Wheat Thioredoxin h in Barley Grains is Biologically Active

Because of interference from other enzymes that oxidize NADPH, the activity of TRXh cannot be accurately assayed in crude extracts, thereby necessitating its partial purification. Partially purified extracts of the different transgenic and control lines were prepared from 15 grams of seed using ammonium sulfate fractionation and gel filtration chromatography. Activity was measured with an NADP-MDH activation assay. Profiles based on these assays show that the activity of TRXh in the transformed seed is much higher than in the nontransformed control (see FIG. 7). The activity results are summarized in Table 4.

Total WTRXh activity from the seeds of two lines transformed with the B1-hordein promoter and the signal sequence (GPBhssBarWtrx-3; GPdBhssBarWtrx-29) is about 4- to 10-fold higher, respectively, than that of control, nontransformed seed. Total activity from a line transformed with the D-hordein promoter without the signal sequence (BGPDhBbarWtrx-5) is only slightly higher (1.25-fold) than that of the nontransformed control (see Table 4). In the transgenics, the specific activity of thioredoxin is generally about 0.128 $A_{340\ nm}$/min/mg protein or about two fold over null segregants.

TABLE 4

Summary of Total Buffer-Extracted Protein and Total Thioredoxin Activity from Active Fraction after Gel Filtration.

| Barley Line | Total Protein, mg | Total Activity, $A_{340}$/ min | Specific Activity, $A_{340}$/min/mg |
| --- | --- | --- | --- |
| Control (GP 4-96) | 102.6 (1.00)* | 7.4 (1.00)* | 0.064 (1.00)* |
| GPDhBarWtrx-5 | 171.2 (1.67) | 9.2 (1.2) | 0.054 (0.8) |
| GpdBhssBarWtrx-29 | 149.1 (1.45) | 72.0 (9.7) | 0.483 (7.5) |
| GpdBhssBarWtrx-3 | 231.3 (2.25) | 27.7 (6.4) | 0.794 (12.4) |

*Numbers in brackets are fold increase over that of the control.

The transformed barley grains analyzed so far appear to have more total buffer-extracted protein than control, non-transformed seed (Table 4).

The transformed grains have a thioredoxin content of at least about 10–15 μg thioredoxin/mg soluble protein(about 2–8 μg thioredoxin/mg tissue) or about two-fold higher than the null segregant.

Figure 8:
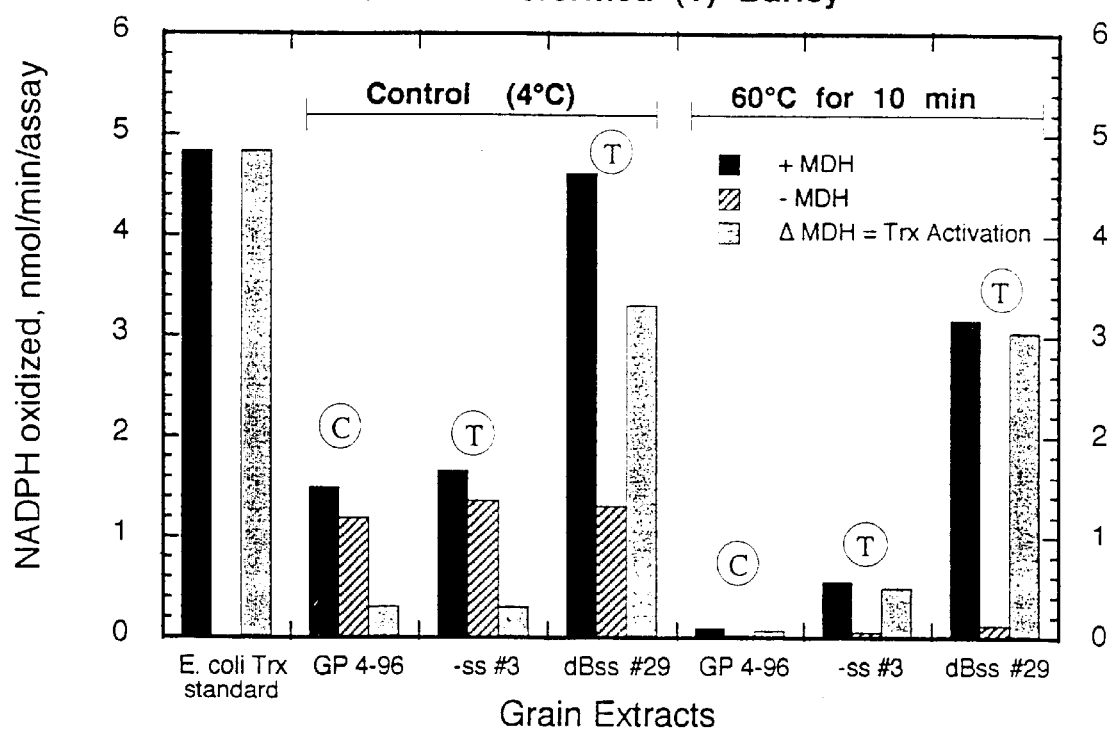
FIG. 8 shows the effects of heat treatment on thioredoxin activity of crude extracts from barley grains.

Because of the tediousness of the $(NH_4)_2SO_4$ procedure and the requirement for large quantities of seed, the original extraction procedure was modified to include a heat treatment step. This change was based on the fact that E. coli WTRXh is stable after treatment at 60° C. for 10 min (Mark and Richardson, 1976). Results on WTRX from two different transgenic barley seeds (GPdBhBarWtrx-3, GPdBhssBarWtr-29) showed no significant difference in activity between the heat treated and non-heat treated extracts (FIG. 8). In addition heat-treatment decreased the endogenous, nonspecific activity in this assay, thereby increasing the reliability of the measurements.

Ten different barley lines (transformed and nontransformed) were extracted using the heat-treatment step and assayed with the NADP-MDH assay; the results are summarized in Table 5. In general, total WTRXh activities in seeds from lines transformed with the B-hordein promoter and signal sequence linked to wtrxh are much higher (4- to 35-fold) than in seeds from lines transformed with the same promoter without signal sequence linked to wtrxh or in seeds from the nontransformed control (Table 5). At this point it is not known whether all expressed wheat WTRXh in barley seeds is heat stable.

TABLE 5

Relative Total Thioredoxin Activity in Different Transgenic Barley Lines.

| Line Designation | Total Protein (%) | Total Activity (%) | Specific Activity (%) |
| --- | --- | --- | --- |
| Non-transgenic control | | | |
| GP4-96 Bar Gene Only | 100 | 100 | 100 |
| GPBar-1 Without Signal Sequence | 92 | 120 | 131 |
| GPdBhBarWtrx-1 | 101 | 192 | 190 |
| GPdBhBarWtrx-22 | 113 | 151 | 133 |
| GPdBhBarWtrx-23 With Signal Sequence | 118 | 180 | 153 |
| GPdBhssBarWtrx-2 | 137 | 1650 | 1203 |
| GPdBhssBarWtrx-14 | 122 | 1723 | 1418 |
| GPdBhssBarWtrx-20 | 147 | 440 | 299 |
| GPdBhssBarWtrx-22 | 154 | 3470 | 2245 |
| GPdBhssBarWtrx-29 | 108 | 1316 | 1219 |

One hundred percent of (a) total protein, mg; (b) total activity, nmol/min; and (c) specific activity, nmol/min/mg protein of the non-transgenic control are: (a) 116.4; (b) 157.38 (c) 1.52, respectively.

Of the stably transformed lines that expressed wheat thioredoxin h, on average, its level was found to be higher in transformants that had the signal peptide-containing constructs than to those that did not (Table 5). Western blot analysis of soluble protein fractions from heterozygous mixtures of seeds from three of the lines, GPdBhssBarWtrx-7, GPdBhssBarWtrx-29, and GPdBhssBarWtrx-22 showed 5.5 times, 22 times, and 10 times more thioredoxin h, respectively, than nontransformed control grain (Table 3). The thioredoxin content of the null segregant (GPdBhssBarWtrx-29-11-10) was about half that of the corresponding, nontransformed control.

Figure 9:
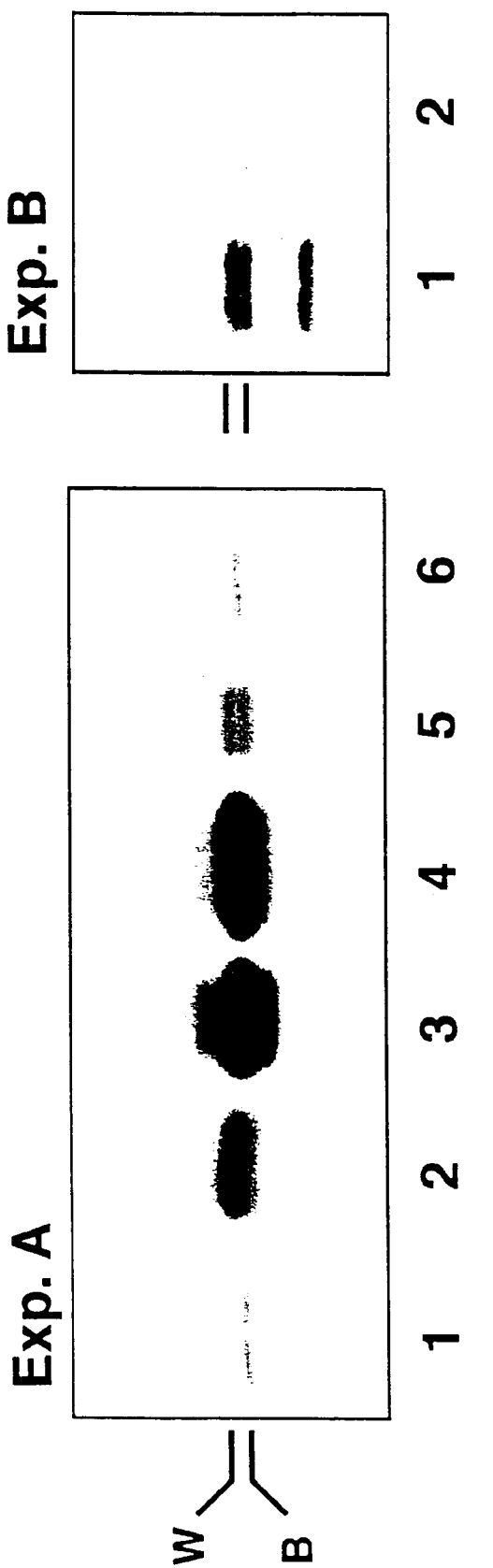
FIG. 9A–B shows a western blot analysis of extract from segregating $T_1$ barley grain of stable transformants containing wtrxh. Panel A: lanes 1 and 6, control barley extract (cv. Golden Promise); lane 2, bread wheat extract (*Triticum aestivum*, cv. Capitole); lane 3, extract from GPdBhss BarWtrx 22; lane 4, extract from GPdBhssBarWtrx 29; lane 5, extract from GPdBhBarWtrx 2. Panel B: lane 1, GPdBh-BarWtrx 2; lane 2 control barley extract. W, wheat; B, barley.

Extracts from barley typically showed one immunologically reactive band (identified by B in FIG. 9A, lanes 1 and 6) but in some transfers showed a second faint, faster moving band (FIG. 9B, lane 2). Tissues from transgenic lines overexpressing wtrxh were characterized by a band that did not correspond to either of the two counterparts in barley, but rather to thioredoxin h from wheat. The difference between the overexpressed 13.5-kDa wheat and the endogenous 13.1-kDa barley thioredoxin h is particularly pronounced in the barley line transformed with the nontargeted thioredoxin h gene (FIG. 9A, line 5 and FIG. 9B, lane 1). Repeated analyses of the various transgenic lines by SDS/PAGE led to the conclusion that the band identified in FIGS. 9A–B by W corresponds to the bread wheat wtrxh introduced by barley. Independent biochemical assays with 5,5'-dithiobis(2-nitrobenzoic acid) (DTNB) (Florencio et al., 1988.) confirmed the ability of barley NTR to reduce wheat thioredoxin h (data not shown).

Figure 10:
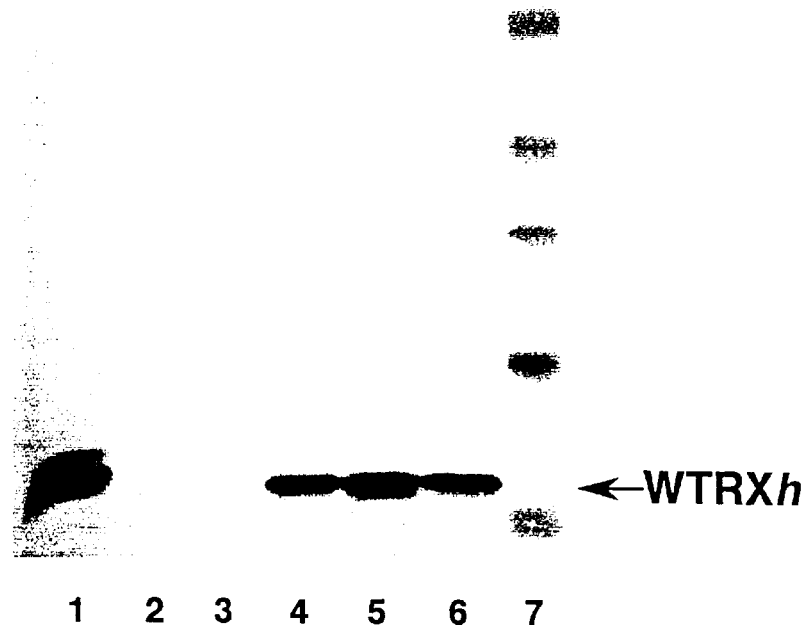
FIG. 10 shows western blot analysis of extracts of $T_1$, $T_2$ and $T_3$ barley grain transformed with wtrxh. Forty micrograms of soluble proteins extracted from 10–20 grains of each line were fractionated by SDS/PAGE. Lane 1, wheat germ thioredoxin h; lane 2, nontransgenic control of GP4-96; lane 3, null segregant $T_2$ grain of GPdBhssBarWtrx-29-11-10; lane 4, heterozygous $T_1$ grain of GPdBhssBarWtrx-29; lane 5, homozygous $T_2$ grain of GPdBhssBarWtrx-29-3; lane 6, homozygous $T_2$ grain of GPdBhssBarWtrx-29-3-2; lane 7, prestained standards (aprotinin, 0.9 kDa; lysozyme, 17.8 kDa; soybean trypsin inhibitor, 30.6 kDa; carbonic anhydrase, 41.8 kDa; BSA, 71 kDa).

Because of their value in assessing biochemical attributes of the grain, homozygous wtrxh lines were identified and analyzed by Western blot. The two lines identified as homozygous showed both enhanced expression of thioredoxin h relative to that of their heterozygous parents and nontransformed controls. Analysis of GPdBhssBarWtrx-29-3 is shown in FIG. 10. It is noted that demonstration of the thioredoxin h present in the nontransgenic control and null segregant grains (not apparent in the exposure shown in FIG. 9) required conditions that led to overexposure of the enriched transgenic preparations. Thioredoxin in the parent heterozygous grain was shown to be biochemically active.

Pullulanase and Pullulanase Inhibitor Activity in Barley Grain Overexpressing Thioredoxin h Pullulanase is an amylolytic enzyme present in cereal grain, which has a disulfide inhibitor protein (Macri et al, 1993.; MacGregor et al., 1994.), the activity of which is linked to thioredoxin (Wong et al., 1995.). Thioredoxin reduced by NADPH via NTR, reduces the disulfide bonds of the inhibitor, allowing the targeted pullulanase enzyme to be active. Because of this relationship, it was of interest to determine the activity of pullulanase in the thioredoxin h-overexpressing transformants.

Spectrophotometric assays (FIG. 13A) of extracts from transformed grain of a homozygous line (GPdBhssBarWtrx-29-3) overexpressing thioredoxin h showed a 3- to 4-fold increase in pullulanase activity on the fifth day after initiation of germination relative to its null segregant. Confirmatory results were obtained in a separate experiment with native activity gels. The increase in activity was apparent either when gels were viewed directly (FIG. 13B) or when the activity on the gels was assessed by scanning and integrating the clarified bands (FIG. 13C). A homozygous line isolated from a different, independent transformation event (GPdBssBarWtrx-2-1-15) showed a similar response (data not shown). The transgenic plants expressed an pullulanase activity of about 1–2 Absorbance units at 534 nm/30 min/mg protein, which is about two-fold higher than null segregants.

Pullulanase inhibitor activity was determined on fractions heated to inactivate pullulanase (70° C. for 15 min) by measuring the inhibition of the fractions on added purified barley malt pullulanase. The endogenous pullulanase activity was shown to be completely eliminated by this heat treatment whereas inhibitor activity was not affected (Macri et al, supra; MacGregor et al., supra). Analysis of comparable grain extracts revealed that the pullulanase inhibitor was inactive on the fourth and fifth days after water addition in both the transformant and null segregants. These results thus demonstrate that the increase in pullulanase activity observed after the third day is not caused by enhanced inactivation of the inhibitor in the transgenic grain. It is possible that thioredoxin acts either by increasing the de novo synthesis of pullulanase (Hardie et al., 1975.) or by lowering the binding of the mature enzyme to the starchy endosperm. There is evidence that some of the pullulanase

Alpha-amylase Activity in Barley Grain Overexpressing Thioredoxin h

Alpha-amylase, also an amylolytic enzyme that is induced by gibberellic acid like pullulanase, has long been considered key to germination. The synthesis of the major (B) and minor (A) forms of this enzyme are known to be triggered by the hormone, gibberellic acid (GA). In addition, alpha-amylase activity is increased in vitro by the reductive inactivation of its disulfide inhibitor protein by thioredoxin h (in the presence of NADPH and NADP-thioredoxin reductase). The present results with transformed barley seeds show that, like pullulanase, thioredoxin h expression alters alpha-amylase activity. In this case, the appearance of the enzyme during germination is accelerated and its abundance and activity are increased.

Figure 14:
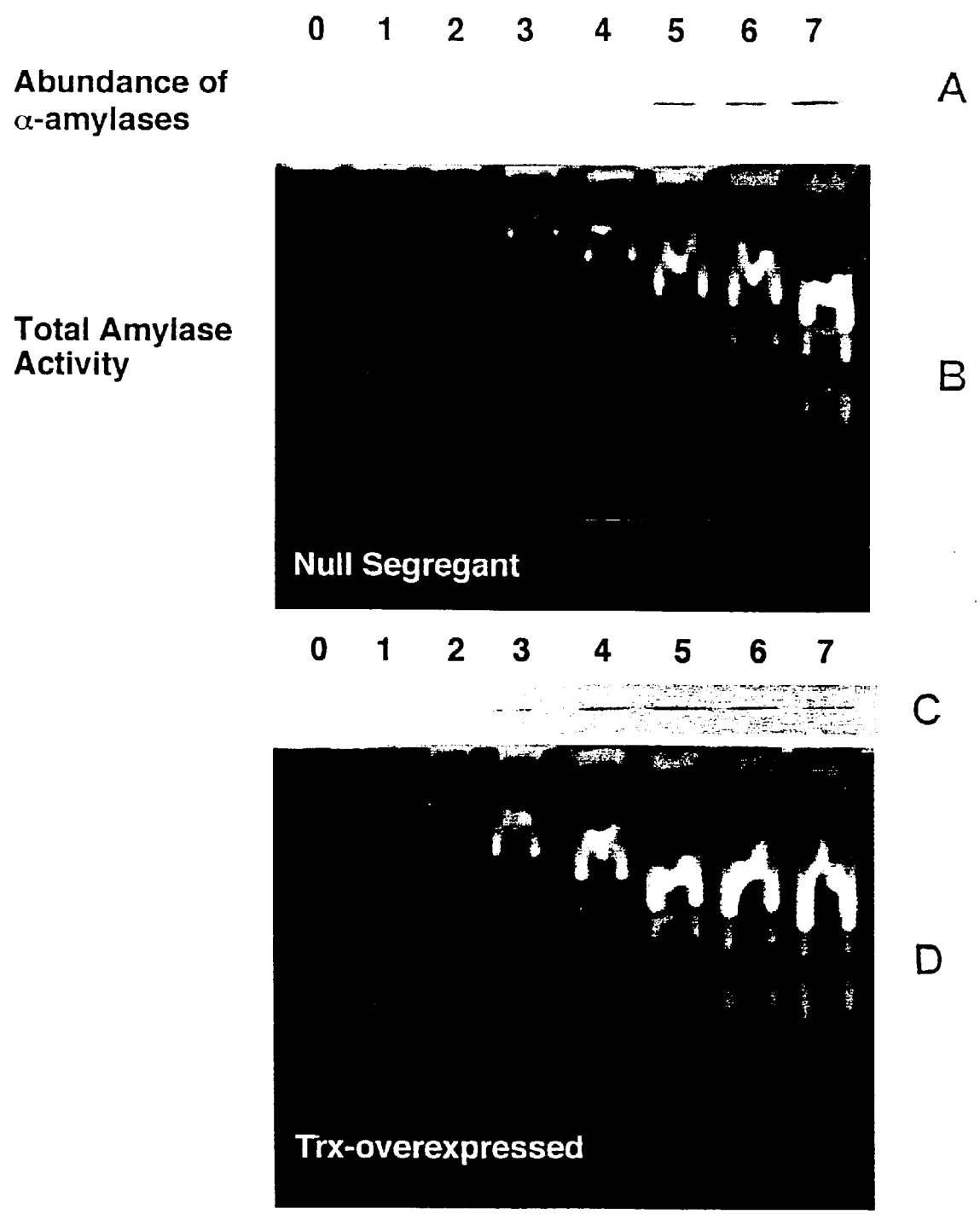
FIG. 14A–D shows the change in the activity and abundance of amylases in transgenic and null segregant barley grains during germination and seedling development based on an activity gel. Panel A: abundance of alpha-amylases in null segregant based on western blot. Panel B: Total amylase activity in null segregant Panel C: abundance of alpha-amylases in thioredoxin overexpressing grains. Panel D: total amylase activity in thioredoxin overexpressed grains.
Figure 15:
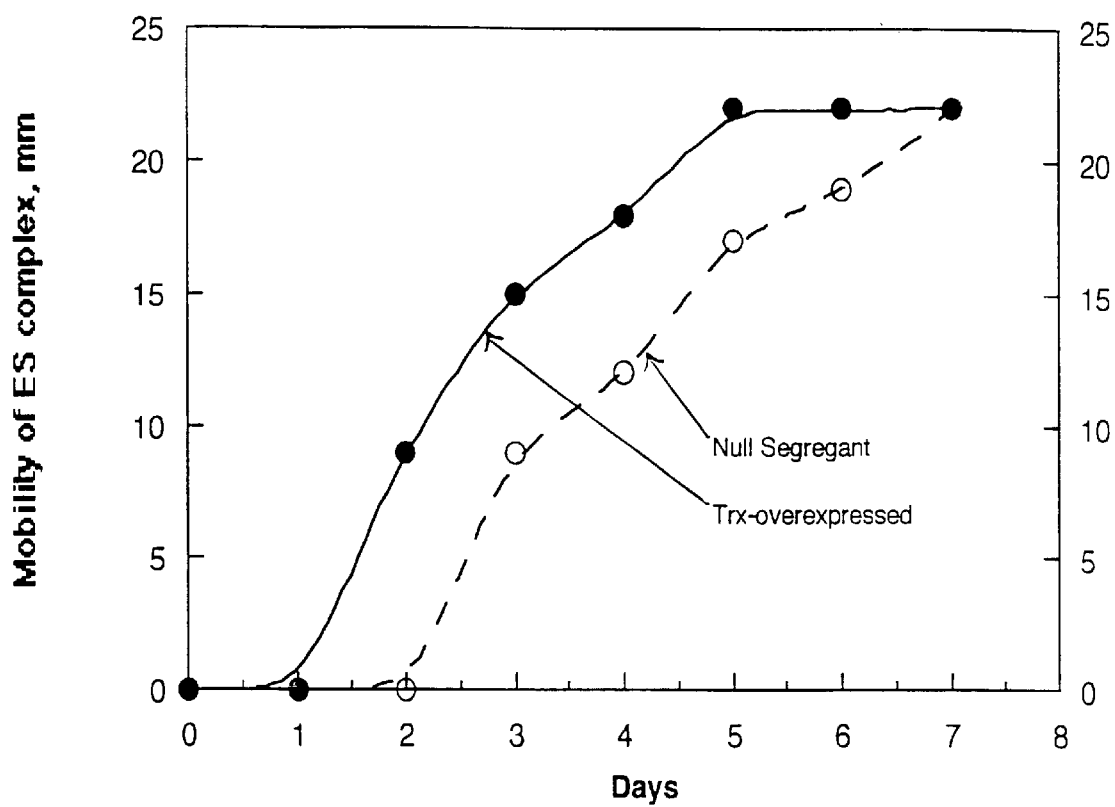
FIG. 15 shows the effect of overexpressed thioredoxin h on the activity of the major form of alpha-amylase during germination and seeding development. The size of the major alpha-amylase activity band in FIG. 14 was estimated by its rate of mobility during electrophoresis.
Figures 16A, 16B:
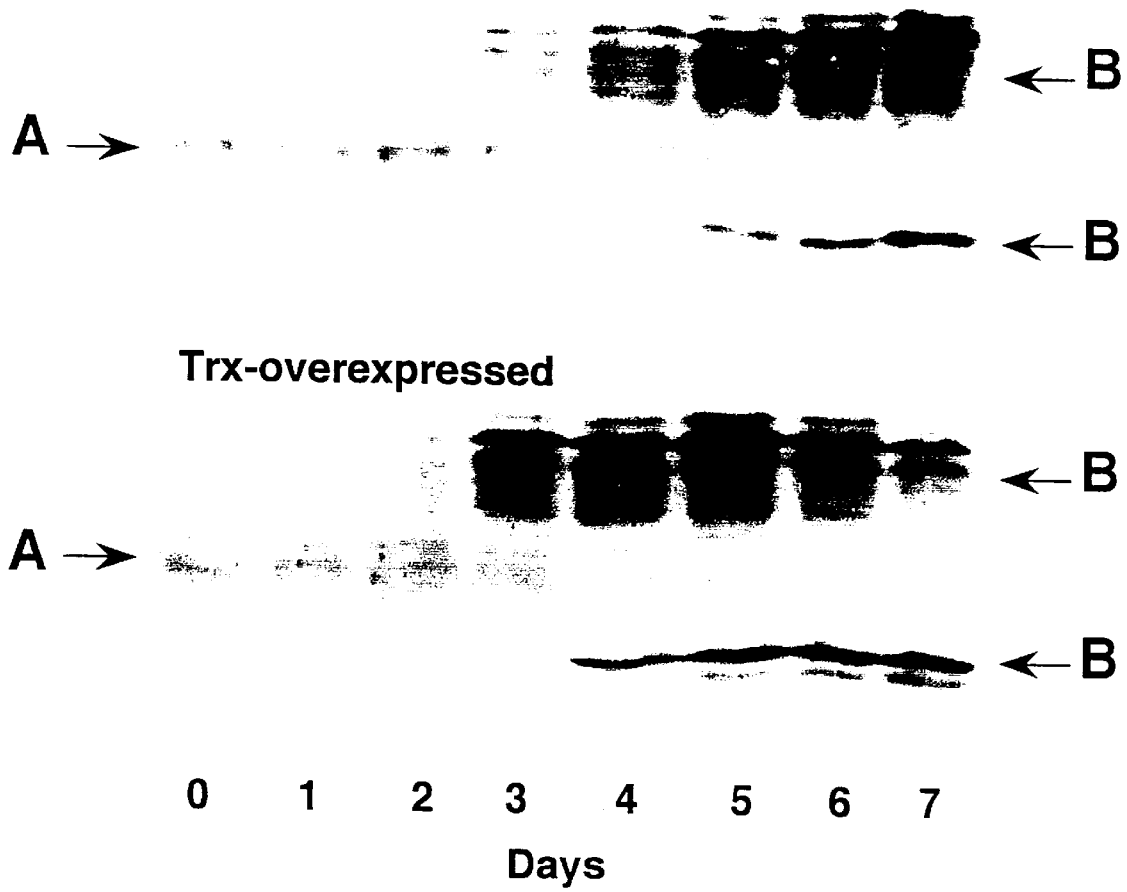
FIG. 16A–B shows the effect of overexpressed thioredoxin h on the abundance of alpha-amylase A and B isozymes during germination and seedling development. The figure represents western blots of IEF gels developed for the null segregant and transgenic barley grains. Panel A: Null segregant. Panel B: Transgenic with thioredoxin overexpressed.

FIG. 14A–D shows the early increase in both the abundance and activity of alpha-amylase (A+B forms) during germination and seedling development. Based on the antibody response in western blots, alpha-amylase was first detected 3 days after the onset of germination in the transgenic grain FIG. 14C) whereas the enzyme did not appear until the fourth day in the null segregant (FIG. 14A). The onset of activity (based on the activity gel) followed a similar pattern (FIG. 14B and FIG. 14D). The mobility of the enzyme in the activity gel also reflected the early induction of activity in the transgenic grain (FIG. 15). That much of this increase in activity seen early on was due to the B (a gibberellic acid-linked form) is supported by FIG. 16. Here, one can also see that the level of the minor A form of the enzyme (also gibberellic acid dependent) was increased in grain overexpressing thioredoxin h. Again, the appearance of significant levels of the major (B form) alpha-amylase enzyme was advanced by 1 day.

Germination of Barley Grains Overexpressinq Thioredoxin h

All operations were carried out at 25° C. (unless otherwise specified below) under conditions described by Kobrehel et al. 1992 and Lozano et al. 1996. Grains were surface sterilized by continuous stirring in 0.25% bleach for 30 min. Bleach was removed by extensive washing with sterilized distilled water. Thirty sterilized null segregant (GPdBhssBarWtrx-29-22-10, in which the transgene was removed by crossing with a self-polinated plant from the same line) and thirty sterilized homozygous (GPdBhssBarWtrx-29-3) seeds were placed in each of a series of plastic Petri dishes (12.5 cm diameter) fitted with three layers of Whatman #1 filter paper moistened with 15 ml sterile distilled water. Plates were wrapped with aluminum foil and grain was germinated in a dark chamber at 20° C. for up to 7 days. One plate was read at each time point shown in FIG. 17. Percent germination, in the first day (from the start of incubation up to 24 hours), was determined by observing the emergence of the radicle. On the subsequent days, percent germination represents seedling growth as determined by measuring the length of coleoptile and roots of the germinated grains.

Figure 17:
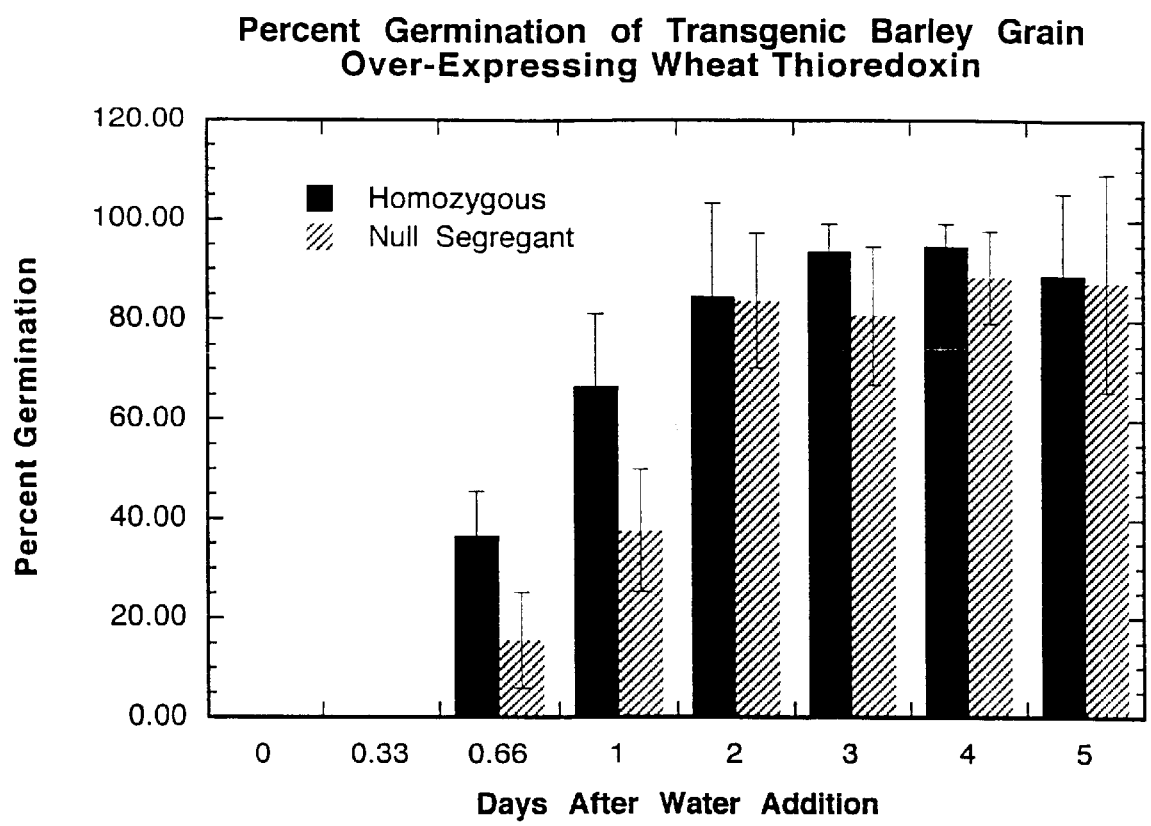
FIG. 17 shows the effect of overexpressed wheat thioredoxin h on the germination of null segregant and transgenic (homozygous) barley grains.

The results, shown in FIG. 17, indicate that germination in transgenic barley overexpressing wheat thioredoxin h is detected about 16 hours after the onset of incubation in about 25–30% of the seeds. In contrast, no germination in the null segregant was detected at 16 hours but is first detected 8 hours later, on Day 1. Therefore, in the transgenic germination is advanced about 8 hours. However, on Day germination was detected in approximately 70% or about twice the number of transgenic grains in comparison to their null segregant counterparts. It is interesting to note that the onset of germination in the transgenics parallels the onset of the detection of alpha amylase as shown in FIG. 15.

Sequential Extraction of Grain Proteins from Transgenic Barley Grains

Isolated endosperm from 10 dry grains or seedlings (germinated as described above) were-ground with mortar and pestle at 4° C. with 3 ml Tris-HCl buffer as indicated below. The separate mixtures of homozygous GPdBhssBarWtrx-29-3 and null segregant GPdBhssBarWtrx-29-22-10 grains were placed in a 5-ml screw-top centrifuge tube. Grains were mechanically shaken for 30 minutes and then centrifuged for 10 min at 24,000×g. The supernatant fraction (buffer-soluble) was decanted and saved for analysis and the residue was extracted sequentially with the following solvents for the indicated times: [1] 0.5 M NaCl (30 min); [2] water (30 min); [3] 2×50% propanol (2hr); [4] 2×50% propanol +2% 2-mercaptoethanol (MET) (2 hr); and [5] 0.5 M borate buffer, pH 10, containing 1% SDS and 2% 2-mercaptoethanol (2 hr). Supernatant fractions of all extracts were determined for volume and protein content (by Coomassie dye binding method), then were stored at −20° C. until use. By convention, the fractions are designated: [1] albumin/globulin (buffer/salt/water); [2] Hordein I (propanol); [3] Hordein II (propanol+MET); and [4] glutelin (Borate/SDS/MET) (Shewry et al., 1980). These fractions were used to determine, protein content, the distribution of proteins between the water soluble and insoluble fractions, the total extractable protein, and reduction with NADPH.

To determine the in vivo redox status of protein from transgenic barley grain during germination and seedling development, the extraction procedure was repeated except that 2 mM mBBr was included in the Tris grinding buffer and the grinding was under liquid nitrogen. The mBBr derivatized proteins were electrophoresed on SDS-polyacrylamide gels (1.5 mm thickness, 10–20% gels, pH 8.5 (Laemmli, 1970). Gels were developed for 16 hr at a constant current of 8 mA. Following electrophoresis, gels were placed in 12% (w/v) trichloroacetic acid and soaked for 4 to 6 hr with one change of solution to fix the proteins; gels were then transferred to a solution of 40% methanol/10% acetic acid for 8 to 10 hr with agitation to remove residual mBBr. The fluorescence of mBBr (both free and protein bound mBBr), was visualized by placing gels on a light box lifted with an ultraviolet light source (365 nm). Following removal of the excess (free) mBBr, images of gels were captured by Gel Doc 1000 (Bio-Rad).

To ascertain the equivalent protein amount of loaded extracts, SDS-gels were stained with Coomassie Brilliant Blue G-250 in 10% acetic acid for 30 min, and destained in 10% acetic acid for 30 min with the aid of a microwave oven. Protein stained gels were captured by Gel Doc 1000 as above.

The quantification of fluorescence (pixel×mm×mm) and protein (optical density×mm×mm) on gels were carried out by a software program for image analysis—Multi-Analyst, version 1.0 (Bio-Rad). Relative reduction was expressed as the ratio of fluorescence to protein.

The results of two experiments shown in Table 6, Table 7, and Table 8 demonstrate an increase in the total protein on a percent grain and a percent weight basis in the transgenic barley as compared to the null segregant. The transgenic have a thioredoxin content that is at least two-fold higher (10–15 μg/mg soluble protein; 2–8μg/gram tissue) than the null segregant. The data indicate that this increase in total extractable protein is the result in redistribution of the protein to the most soluble albumin/globulin fraction. The redistribution of the protein to the soluble fraction increase in the transgenics is at least 5% higher than the controls.

TABLE 6

Protein Content of Various Fractions in Transgenic Barley Grain Overexpressing Wheat Thioredoxin h
Experiment I*

| Protein Fraction | Null Segregant | | Homozygous | |
|---|---|---|---|---|
| | mg/seed | mg/gram | mg/seed | mg/gram |
| Albumin/Globulin | 0.462 | 12.25 | 0.546 | 13.58 |
| Hordein I | 0.239 | 6.34 | 0.322 | 8.01 |
| Hordein II | 0.136 | 3.61 | 0.094 | 2.34 |
| Glutelin | 0.110 | 2.92 | 0.097 | 2.41 |
| Total Extractable Protein | 0.947 | 25.12 | 1.059 | 26.34 |

*Weight per 10 seeds is 0.377 and 0.402 full null segregant and homozygous line of transgenic barley

TABLE 7

Protein Content of Various Fractions in Transgenic Barley Grain Overexpressing Wheat Thioredoxin h
Experiment II*

| Protein Fraction | Null Segregant | | Homozygous | |
|---|---|---|---|---|
| | mg/seed | mg/gram | mg/seed | mg/gram |
| Albumin/Globulin | 0.691 | 20.03 | 1.044 | 27.12 |
| Hordein I | 0.373 | 10.81 | 0.368 | 10.03 |
| Hordein II | 0.254 | 7.36 | 0.240 | 6.23 |
| Glutelin | 0.066 | 1.91 | 0.062 | 1.61 |
| Total Extractable Protein | 1.384 | 40.11 | 1.732 | 44.99 |

*Weight per 10 seeds is 0.377 and 0.402 for null segregant and homozygous line of transgenic barley

TABLE 8

Percent increase of Extractable Protein in Homozygous Line

| | %/grain basis | %/mass basis |
|---|---|---|
| Experiment I | 12 | 4.9 |
| Experiment II | 25 | 12 |

Figure 18:
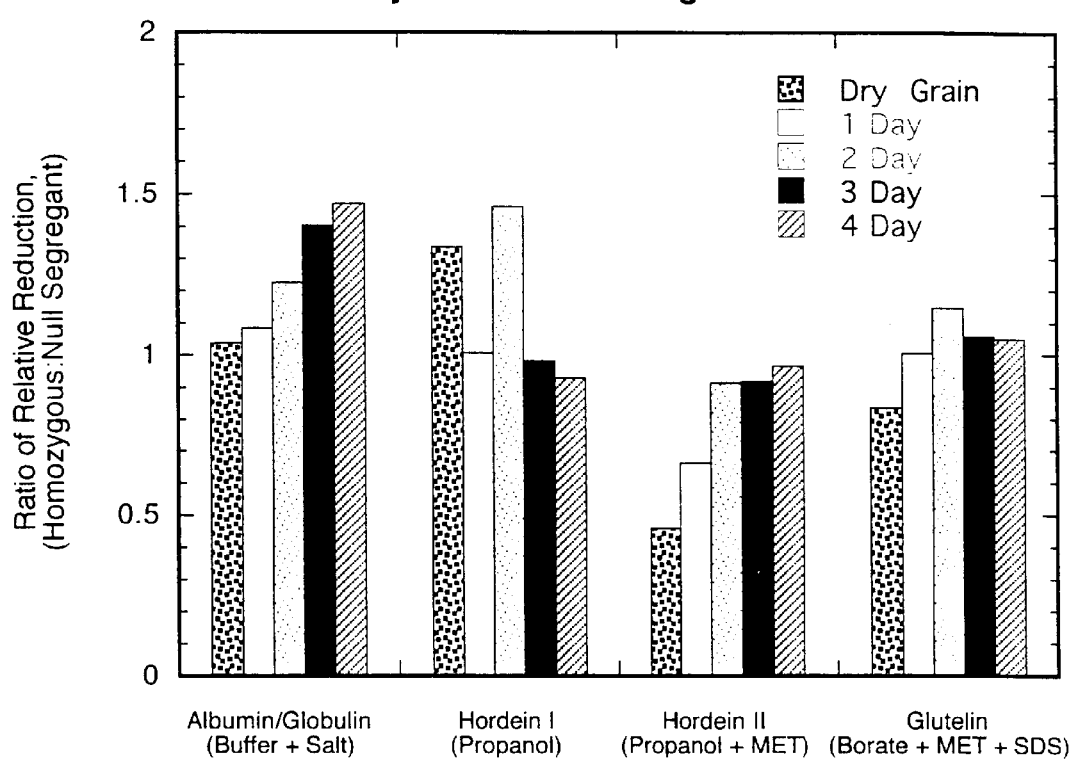
FIG. 18 shows the relative redox status of protein fractions in transgenic barley grain overexpressing wheat thioredoxin h in comparison to the null segregant in dry and germination grain.

Analysis of the relative redox status (SH:SS) of protein fractions in transgenic and null segregant barley grains during germination and as dry grains are shown in FIG. 18. In dry transgenic grain, the greatest increase in reduction relative to the null segregant was observed in the hordein I fraction. This increase was paralleled by decreases in the relative redox status in the hordein II and glutelin fractions while the relative redox status of the albumin/globulin fraction was unchanged. The relative redox status of the transgenic in comparison to the null segregant is at least 5:1.

During germination, the albumin/globulin fraction progressively increases, reaching a relative redox ratio of about 1.5 on Day 4. The relative redox status of the hordein II and glutelin fractions also increased during germination but only reached parity with the null segregant. In contrast the relative redox status of the hordein I fraction was highly variable.

Example 4

Barley Thioredoxin h Gene (btrxh) Transformation

MATERIALS AND METHODS

Plant Material and Culture of Explants

Mature seeds of rice (*Oryza sativa L.* cv. Taipei 309) were surface-sterilized for 20 min in 20%(v/v) bleach (5.25% sodium hypochlorite) followed by 3 washes in sterile water. The seeds were placed on 2 different NB (Chen L et al. (1998) Plant Cell Rep 18: 25–31)-based callus-induction media; (1) NBD'BC2 medium containing 2.0 mg/L 2,4-D, 0.1 mg/L BAP and 0.5 μM $CuSO_4$ (Cho M.-J., unpublished), (2) NBDBC3 medium containing 1.0 mg/L 2,4-D, 0.5 mg/L BAP and 5.0 μM $CuSO_{d\,4}$ (Cho M.-J., unpublished). Five to 7 d after plating, germinating shoots and roots from the mature seeds were completely removed by manual excision. After three weeks of incubation at 24+1° C. under dim-light conditions (approximately 10 to 30 $\mu Em^{-2}s^{-1}$, 16 h-light), tissues with shiny, nodular and compact structures were selected and subsequently maintained on NBDBC4 medium containing 0.5 mg/L 2,4-D, 2.0 mg/L BAP and 5.0 μM $CuSO_4$ (Cho M.-J., unpublished), subculturing at 3 to 4 week intervals, to proliferate highly regenerative, green tissues.

Construction of a Barley Thioredoxin h Expression Vector and DNA Sequencing pdBhssBTRXN(Km)-2 (Cho M.-J., unpublished): the chimeric DNA construct containing the $B_1$-hordein promoter-signal sequence-btrxh (barley thioredoxin h gene) was obtained using a modified method of site-directed mutagenesis by PCR (Cho and Lemaux 1997). The four-primer strategy was used to produce 2 major PCR products. Primers, Bhor7 (5'-GTA AAGCTTTAACAACCCACACATTG-3'; SEQ ID NO:41) containing HindIII restriction site and BhorssBtrx2R (5'-CGCCGTTGCCGACGCCGCTGCAATCGTACTTGTTG CCGCAAT-3'; SEQ ID NO:42), were used for amplification of 0.49-kb $B_1$-hordein 5' region including the $B_1$-hordein signal peptide sequence using the λ2–4/HindIII plasmid containing genomic clone of $B_1$-hordein (Brandt et al., 1985; Cho et al., 1997) as a template. The primer BhorssBtrx2R is an overlapping primer containing the btrxh coding sequence (italicized) and a partial signal peptide sequence from the $B_1$-hordein promoter without the ATG initiation codon for btrxh. The second PCR product was amplified using primers, BorssBtrx4 (5'-ACAAGTACGATTGCAGCGGCGTCGGCAACGGC-3'; SEQ ID NO:43) and Btrxh2R (ata gagctcTTACTGGGCCGCCGCGTG; SEQ ID NO:44); cDNA clone containing btrxh (Caillau, del Val, Cho, Lemaux and Buchanan, unpublished) was used as template. The second set of PCR reactions was produced 0.86-kb chimeric fragments using two PCR-amplified fragments (each diluted 50 times) and two external primers, Bhor7 and Btrx2R. pdBhssBTRXN(Km)-2 was made by replacing the maize ubiqutin promoter in pUbilNosKmf(−) with the 0.86-kb PCR-amplified HindIII/SacI fragment containing $B_1$I-hordein promoter with its signal peptide sequence plus btrxh. Thus, construct pdBhssBTRXN(Km)-2 contains the barley endosperm-specific $B_1$-hordein promoter with its signal peptide sequence, btrxh and nos. The signal peptide sequence containing the ATG initiation codon was directly combined with the sequence of the btrxh gene, without having extra amino acid sequences between the two, in order to make barley thioredoxin h protein provide a precise cleavage site in the lumen of endoplasmic reticulum (ER). The PCR-amplified region of the construct was further confirmed by DNA sequencing, and used for stable transformation of rice.

Stable Transformation

Approximately 4- to 5-month-old highly regenerative cultures maintained on NBDBC4 medium were used for bombardment. Tissue pieces (34 mm) were transferred for osmotic pretreatment to NBDBC4 medium containing mannitol and sorbitol (0.2 M each). Four hours after treatment with osmoticum, tissues were bombarded as previously described (Lemaux et al. 1996; Cho et al. 1998). Gold particles (1.0 μm), coated with 25 μg of a mixture of pAct1IHPT4 and pdBhssBTRXN(Km)-2 at a molar ratio of 1:2 were used for bombardment with a Bio-Rad PDS- 1000 He biolistic device (Bio-Rad, Hercules, Calif.) at 900 or 1100 psi. Sixteen to 18 h after bombardment, tissues were placed on osmoticum-free NBDBC4 medium supplemented with 20 mg/L hygromycin B and grown at 24±1° C. under dim-light (10–30 $\mu Em^{-2}s-1$). From the third round of selection onward, tissues were subcultured at 3-to 4-week intervals on NBDBC4 medium containing 30 mg/L hygromycin B. When a sufficient amount (a plate) of the putatively transformed highly regenerative tissue was obtained, it was plated on NBNBC4 medium containing 0.5 mg/L NAA, 2.0 mg/L BAP and 5.0 μM $CuSO_4$ (Cho M.-J., unpublished) and exposed to higher intensity light (approximately 45–55 $\mu Em^{-2}s^{-1}$). Green shoots were then transferred to Magenta boxes containing phytohormone-free regeneration medium [MS (Murashige and Skoog (1962) Physiol. Plant 15:473–497) plus 20 g/L sucrose] with 10 to 20 mg/L hygromycin B. After four weeks, regenerated plantlets were transferred to soil.

Genomic DNA Isolation, Polymerase Chain Reaction (PCR)

Putative transgenic lines were screened by DNA PCR using two a set of btrxh primers, Btrxh5 (5'-CCAAGAAGTTCCCAAATGC-3'; SEQ ID NO:45) and Btrxh2R. PCR amplification resulted in 0.19-kb intact btrxh from transgenic lines. One btrxh-positive line (OSHptBTRX-I) was obtained. Amplifications were performed in a 25-μl reaction with Taq DNA polymerase (Promega, Madison, Wis.) as described (Cho et al. 1998).

Example 5

Barley NTR Gene (bntr) Transformation

NADP/thioredoxin system (NTS), is analogous to the system established for animals and most microorganisms, in which thioredoxin (h-type in plants) is reduced by NADPH and NADP-thioredoxin reductase (NTR) (Johnson et al., 1987a; Florencio et al., 1988; Suske eta!., 1979). Without being bound by theory, the NTR appears to be a limiting factor for NTS. Therefore, we isolated barley ntr gene from barley cDNA library (Cho, Lemaux and Buchanan, unpublished) and introduce this gene into barley, wheat, and rice plants.

Construction of a Barley NTR Expression Vector and DNA Sequencing pActiIBNTRN4 (Cho M.-J., unpublished): pActiIBNTRN4 was made by ligating the PCR-amplified XbaI/KpnI fragment containing barley nfr cDNA sequence. Primers, BNTR29 (5'attctagaATGGAGGGATCCGCCGCGGCGCCGCTC-3'; SEQ ID NO:46) and BNTR23R (5'-ttggtaccTCAATCAGACTTGCCCACCTGT-3'; SEQ ID NO:47), were used for amplification of the 1.012-Kb XbaI/KpnI fragment containing 0.996-Kb barley ntr coding sequence; small letters contain a restriction enzyme site for subcloning of the DNA construct containing barley ntr gene and underlined letters indicate the barley ntr sequences. The barley ntr fragment was purified from a 0.7% agarose gel using QIAquick® gel extraction kit, digested with XbaI and KpnI and ligated into XbaI/KpnI-digested pAct1INosKmf(–) to generate the pActiIBNTRN4 plasmid. Nucleotide sequences of the PCR-amplified barley ntr coding region were determined by DNA sequencing.

Barley ntr expression vectors driven by barley endosperm-specific $B_1$- or D-hordein promoter with or without its signal peptide sequence are constructed.

Stable Transformation

Transformation of barley, wheat and rice is conducted as previously described above and in Lemaux et al., 1996; Cho et al., 1998; Kim et al., 1999. Barley trxh alone, barley ntr alone or a mixture of both genes are used for bombardment with a Bio-Rad PDS-1000 He biolistic device (BioRad, Hercules, Calif.) at 900 or 1100 psi. After obtaining transgenic lines, they arel analyzed for tests of redox state, germinability, allergenicity, and baking quality.

According to the above examples, other types of plants, are transformed in a similar manner to produce transgenic plants overexpressing thioredoxin and NTR either alone or in combination, such as transgenic wheat, rice, maize, oat, rye sorghum, millet, triticale, forage grass, turf grass, soybeans, lima beans, tomato, potato, soybean, cotton, tobacco etc. Further, it is understood that thioredoxins other than wheat or barley thioredoxin or thioredoxin h can be used in the context of the invention. Such examples include spinach h; chloroplast thioredoxin m and f, bacterial thioredoxins (e.g., E. coli) yeast, and animal and the like. In addition, it is understood the NTR other than barley NTR protein also can be used in the context of the invention such as spinach, wheat, and NTR of monocots and dicots.

This invention has been detailed both by example and by description. It should be apparent that one having ordinary skill in the relevant art would be able to surmise equivalents to the invention as described in the claims which follow but which would be within the spirit of the foregoing description. Those equivalents are included within the scope of this invention. All herein cited patents, patent applications, publications, references and references cited therein are hereby expressly incorporated by reference in their entirety.

REFERENCES

Ainley W M, McNeil K J, Hill J W, Lingle W L, Simpson R B, Brenner M L, Nagao R T, Key J L (1993) Regulatable endogenous production of cytokinins up to "toxic" levels in transgenic plants and plant tissues. Plant Molecular Biology 22(1):13–23.

Altschul et al. (1990). J. Mol. Biol., 215: 403–10.

Altschul et al. (1994). Nature Genet., 6: 119–29.

Altschul et al., (1996) Methods in Enzymology, 266: 460–480.

An G, Costa M A, Mitra A, Ha SOB, Marton L (1988) Organ-specific and developmental regulation of the nopaline synthase promoter in transgenic tobacco plants. Plant Physiology (Rockville) 88(3):547–552.

Astwood J, Leach J N, Fuchs R L, (1996) Stability of food allergens to digestion in vitro. Nature Biotechnology, 14(10):1269–1273.

Ausubel et al. (1987) In Current Protocols in Molecular Biology, Greene Publishing Associates and Wiley-Intersciences.

Bagga et al. (1997) Plant Cell 9:1683–1696.

Besse and Buchanan (1997) Bot. Bull. Acad. Sin. 38:1–11.

Besse I, Wong J H, Kobrehel K, Buchanan B B (1996) Thiocalsin: a thioredoxin-linked, substrate-specific protease dependent on calcium. Proc Natl Acad Sci USA 93: 3169–3175.

Bondenstein-Lang J, Buch A, Follman H (1989) Animal and plant mitochondria contain specific thioredoxins. FEBS Lett 258: 22–26.

Bower M S, Matias D D, Femandes-Carvalho E, Mazzurco M, Gu T, Rothstein S J, Goring D R (1996) Two members of the thioredoxin in-family interact with the kinase domain of a *Brassica S locus* receptor kinase. Plant Cell 8: 1641–1650.

Bradford (1976) Anal. Biochem. 72:2 48–254.

Brandt A, Montembault A, Cameron-Mills V, Rasmussen S K (1985) Primary structure of a B1 hordein gene from barley. Carlsberg Res Commun 50: 333–345.

Bright S W, Shewry P R (1983) Improvement of protein quality in cereals. CCC Critical Plant Reviews 1:49–93.

Brugidou C, Marty I, Chartier Y, Meyer Y (1993) The *Nicotiana tabacum* genome encodes two cytoplasmic thioredoxin genes which are differently expressed. mol Gen Genet 238:285–293.

Buchanan B B (1991) Regulation of $CO_2$ assimilation in oxygenic photosynthesis: the ferredoxin/thioredoxin system. Arch Biochem Biophys 287: 337–340.

Buchanan B B, Adamidi C, Lozano R M, Yee B C, Momma M, Kobrehel K, Ermel R Frick O L (1997) Thioredoxin-linked mitigation of allergic responses to wheat. Proc Natl Acad Sci USA 94:5372–5377.

Buchanan et al. (1994) Arch. Biochem. Biophys. 314: 257–260.

Buchanan et al. (1998) Leatherhead Food RA Food Ind. J. 1: 97–105.

Bustos M M, Guiltinan M J, Jordano J, Begum D, Kalkan F A, Hall T C (1989) 1(9):839–853, Callis J, Fromm M, Walbot V (1988) Heat inducible expression of a chimeric maize hsp70CAT gene in maize protoplasts. Plant Physiology (Rockville) 88(4):965–968.

Cameron-Mills V (1980) The structure and composition of protein bodies purified from barley endosperm by silica sol density radients. Carlsberg Res Commun 45: 557–576.

Cameron-Mills V, Brandt A (1988) A B-hordein gene. Plant Mol. Biol 11:449–461.

Cameron-Mills V, Madrid S M J (1988) The signal peptide cleavage site of a B1 hordein determined by radiosequencing of the in vitro synthesized and processed polypeptide. Carlsberg Res Commun :4:1 81–192.

Cameron-Mills V, Wettstein D von (1980) Protein body formation in the developing barley endosperm. Carlsberg Res Commun 45: 77–594.

Carpenter et al. (1992) The Plant Cell 4: 557–571.

Cho M-J, Lemaux P G (1997a) Rapid PCR amplification of chimeric products and its direct application to in vivo testing of recombinant DNA construction strategies. Mol. Biotechnol. 8:13–16.

Cho M-J, Vodkin I, Widholm J M (1 997b) Transformation of soybean embryogenic culture by microprojectile bombardment. Plant Biotechnol. 14:11–16.

Cho M-J, Ha C D, Buchanan B B, Lemaux P G (1998a) Subcellular targeting of barley hordein promoter-uidA fusions in transgenic barley seed. P-1024. Congress In Vitro Biology, Las Vegas, Nev. May 30–Jun. 3, 1998.

Cho M-J, Jiang W, Lemaux P G (1998b) Transformation of recalcitrant cultivars through improvement of regenerability and decreased albinism. Plant Sci. 138:229–244.

Cho M-J, Zhang S, Lemaux P G (1998c). Transformation of shoot meristem tissues of oat using three different selectable markers. In Vitro Cell Dev. Biol. 34P:340.

Cho M-J, Choi H W, Buchanan B B, Lemaux P G (1999a) Inheritance of tissue-specific expression of barley hordein promoter-uidA fusions in transgenic barley plants. Theor. Appl. Genet. 98:1253–1262.

Cho M-J, Buchanan B B, Lemaux P G (1999b) Development of transgenic systems for monocotyledonous crop species and production of foreign proteins in transgenic barley and wheat seeds. In: Application of Transformation Technology in Plant Breeding. Special Seminar for the 30th Anniversary Korean Breeding Soc., Suwon, Korea, Nov. 19, 1999, pp.39–53.

Cho M-J, Choi H W, Lemaux P G (1 999c) Transgenic orchardgrass (*Dactylis glomerata L.*) plants produced from high regenerative tissues. P-1089. Congress In Vitro Biology, New Orleans, La. Jun. 5–9, 1999.

Cho M-J, Jiang W, Lemaux P G (1 999d) High frequency transformation of oat via microprojectile bombardment of seed-derived regenerative cultures. Plant Sci. 148:9–17.

Cho M-J, Wong J, Marx C, Jiang W, Lemaux P G, Buchanan B B (1999e) Overexpression of thioredoxin h leads to enhanced activity of starch debranching enzyme (pullulanase) in germinating barley seeds. Proc. Natl. Acad. Sci. USA 96:14641–14646.

Cho M-J, Ha C D, Lemaux P G (2000) Production of transgenic tall fescue and red fescue plants by particle bombardment of mature seed-derived highly regenerative tissues. Plant Cell Rep. (in press).

Christensen and Quail (1996) Transgenic Res. 5:1–6.

Conrad et al. (1998) Journal of Plant Physiology 152:708–711.

Corpet et al. (1988) Nucleic Acids Research 16: 10881–90.

del Val., Yee B C, Lozano R M, Buchanan B B, Ermel R E, Lee Y M, and Frick O L. (1999) J. Aller. Clin. Immunol. 104:690–697.

Dai S, Saarinen M, Ramaswamy S, Meyer Y, Jacquot J-P, Eklund H (1996) Crystal structure of *Arabidopsis thaliana* NADPH dependent thioredoxin reductase at 2.5 A resolution. J Mol Biol 264:1044–1057.

Dellaporta S (1993) Plant DNA miniprep and microprep. Freeling M, Walbot V (eds) In: Maize Handbook. p 522–525.

Dekeyser R A, Claes B, De Rycke R M U, Habets M E, Van Montagu M C, Caplan A B (1990) Transient gene expression in intact and organized rice tissues. Pant Cell 2(7):591402.

Denis M, Delourme R, Gourret J-P, Mariani C, Renard M (1993) Expression of engineered nuclear male sterility in *Brassica napus*: Genetics, morphology, cytology, and sensitivity to temperature. Plant Physiology (Rockville), 101 (4):1295–1304.

Entwistle J, Knudsen S, Muller M, Cameron-Mills V (1991) Amber codon suppression: the in vivo and in vitro analysis of two C-hordein genes from barley. Plant Mol Biol 17: 1217–1231.

Florencio et al. (1988) Arch. Biochem. Biophys. 266: 496–507.

Forde B G, Heyworth A, Pywell J, Kreis M (1985) Nucleotide sequence of a B1 hordein gene and the identification of possible upstream regulatory elements in endosperm storage protein genes from barley, wheat and maize. Nucl Acids Res 13: 7327–7339.

Fromm H, Katagiri F, Chua N H (1989) An octopine synthase enhancer element directs tissue-specific expression and binds ASF-1, a factor from tobacco nuclear extracts.

Furgon L, Curioni A, Peruffo A D. (1994) Anal. Biochem. 221:200–201.

Gatz C. (1997) Chemical control of gene expression. Jones R L (Ed) Annual Review of Plant Physiology and Plant Molecular Biology 48:89–108.

Gautier et al. (1998) Eur. J. Biochem. 252: 314–324.

Gelvin et al. (1990) Plant Molecular Biology Manual, Klower Academic Publishers.

Giese H, Andersen B, Doll H (1983) Synthesis of the major storage protein, hordein, in barley. Pulse-labeling study of grain filling in liquid-cultured detached spikes. Planta 159: 60–65.

Gilmartin et al. (1992) The Plant Cell 4: 839–949.

Grimwade et al. (1996) Plant Molecular Biology 30: 1067–1073.

Hardie D G. (1975) Phytochem. 14:1719–1722.

Harlow & Lane (1988) Antibodies, A Laboratory Manual, Cold Spring Harbor Laboratory, New York.

Higgins and Sharp (1988) Gene, 73: 237–244.

Higgins and Sharp (1989) CABIOS 5: 151–153.

Horecka T, Perecko D, Kutejova E, Muchova K, Kolloarova M (1996) Purification and partial characterization of two thioredoxins from *Streptomyces aureofaciens*. Biochemistry and Molecular Biology International 40(3):497–505.

Huang, et al. (1992) Computer Applications in the Biosciences 8: 153–65.

Hunter C P (1988) Plant regeneration from microspores of barley, Hordeum vulgare. PhD thesis. Wye College, University of London, Ashford, Kent.

Innis et al. (eds.) (1990) PCR Protocols, A Guide to Methods and Applications, Academic Press, Inc., San Diego, Calif.

Ishiwatari et al. (1995) Planta 195(3): 456–463.

Jacquot J-P, Rivera-Madrid R, Marinho P, Kollarova M, Le Marechal P, Miginiac-Maslow M, Meyer Y (1994) *Arabidopsis thaliana* NADPH thioredoxin reductase cDNA characterization and expression of the recombinant protein in *Escherichia coli*. J Mol Biol 235:1357–1363.

Jiao J., Yee B C, Kobrehel K, Buchanan B B (1992). Effect of thioredoxin-linked reduction on the activity and stability of the Kunitz and Bowman-Birk soybean trypsin inhibitor proteins. J: Agric. Food Chem 40: 2333–2336.

Johnson T C, Cao R Q, Kung J E, Buchanan B B, Holmgren (1987a) Thioredoxin and NADP-thioredoxin reductase from cultured carrot cells. Planta 171: 321–331.

Johnson T C, Wada K, Buchanan B B, Holmgren A (1987b) Reduction of purothionin by the wheat seed thioredoxin system and potential function as a secondary thiol messenger in redox control. Plant Physiol 85:446–451.

Kim et al. (1999). P-1021 Congress on In Vitro Biol, New Orleans, La. Jun. 5–9, 1999.

Kobrehel et al. (1994) Thioredoxin-linked reduction of wheat storage proteins. II. Technological Consequences. In Gluten Proteins: 1993. Association of Cereal Research; Detmold, Germany.

Kobrehel K, Wong J H, Balogh A, Kiss F, Yee B C, Buchanan B B (1992) Specific reduction of wheat storage proteins by thioredoxin h. Plant Physiol 99: 919924.

Kobrehel K, Yee B C, Buchanan B B (1991) Role of the NADP/thioredoxin system in the reduction of ct-amylase and trypsin inhibitor proteins. J Biol Chem 266: 16135–16140 Kuhlemeier et al. (1989) Plant Cell 1: 471.

Kuriyan J, Krishna T S R, Wong L, Guenther B, Pahler A, Williams C H, Model P (1991) Convergent evolution of similar function in 2 structurally divergent enzymes. Nature 352:172–174.

Laemmli, U K (1970) Cleavage of structural proteins during the assembly of the head of bacteriophage T4. Nature 997: 680–685.

Laurent T C, Moore E C, Reichard P (1964) Enzymatic synthesis of deoxy-ribonucleotides IV. Isolation and characterization of thioredoxin, the hydrogen donor from *Eschenchia coli* B. J Biol Chem 239:3436–3444.

Lemaux P G, Cho M-J, Louwerse J, Williams R, Wan Y (1996) Bombardment-mediated transformation methods for barley. Bio-Rad US/KG Bulletin 2007: 1–6.

Li X, Nield J, Hayman D, Langridge P (1995) Thioredoxin activity in the C terminus of Phalaris S protein. Plant J8: 133–138.

Liu S, Kriz, A (1996) Tissue-specific and ABA-regulated maize GIb1 gene expression in transgenic tobacco. Plant Cell Pep 16: 158–162.

Lozano R M, Wong J H, Yee B C, Peters A, Kobrehel K, Buchanan B B (1996) New evidence for a role for thioredoxin h in germination and seedling development. Planta 200: 100–106.

Lozano R M, Yee B C, Buchanan B B (1994) Thioredoxin-linked reductive inactivation of venom neurotoxins. Arch Biochem Biophys 309:356–362.

MacGregor A W, Marci L J, Schroeder S W, Bazin S L (1994) J. Cereal Sci. 20:33–41.

Marci J L, MacGregor, A W, Schoreder, S W, Bazin, S L. (1993) J. Cereal. Sci. 18:103–106.

Marcotte et al. (1989) Plant Cell 1: 969.

Marcus F, Chamberlain S H, Chu C, Masiarz F R, Shin S, Yee B C, Buchanan, B B (1991) Plant thioredoxin h: an animal-like thioredoxin occurring in multiple cell compartments. Arch Biochem Biophys 287:195–198.

Mark and Richardson (1976) Proc. Natl. Acad. Sci. USA 73:780–784.

Marris C, Gallois P, Copley J, Kreis M (1988) The 5' flanking region of a barley B hordein gene controls tissue and developmental specific CAT expression in tobacco plants. Plant Mol Biol 10:359–366.

Marty I, and Meyer Y (1991) Nucleotide sequence of a complementary DNA encoding a tobacco thioredoxin. Plant Mol Biol 17:143–148.

Moore E C, Reichard P, Thelander L (1964) Enzymatic synthesis of deoxyribonucleotides. Purification and properties of thioredoxin reductase from *Escherichia coli* B. J Biol Chem 239:3445–3453.

Muller M, Knudsen S (1993) The nitrogen response of a barley C-hordein promoter is controlled by positive and negative regulation of the GCN4 and endosperm box. Plant J 4: 343–355.

Murashige T, Skoog F (1962) A revised medium for rapid growth and bioassays with tobacco tissue cultures. Physiol Plant 15: 473–497.

Myers and Miller (1989) CABIOS 4:11–17.

Needleman and Wunsch (1970) J. Mol. Biol. 48:443.

Opperman C H, Taylor C G, Conkling M A. (1994) Root-knot nematode-directed expression of a plant root-specific gene. Science (Washington, D.C.), 263(5144):221–223.

Pai E F (1991) Variations on a theme: the family of FAD-dependent NAD(P)H-(disulphide)oxidoreductases. Curr Opin Struct Biol 1:796–803.

Pearson and Lipman (1988) Proc. Natl. Acad. Sci. USA 85:9444.

Pearson et al. (1994) Methods in Molecular Biology 24:307–331.

Rasmussen S K, Brandt A (1986) Nucleotide sequences of cDNA clones for C-hordein polypeptides. Carlsberg Res Commun 51:371–379.

Rivera-Madrid et al. (1993) Plant Physiology 102: 324–328.

Rivera-Madrid et al. (1995) Proc. Natl. Acad. Sci. USA 92:5620–5624.

Russel M, Model P (1988) Sequence of thioredoxin reductase from *Escherichia coli*. Relation to other flavoprotein disulfide oxidoreductases. J Biol Chem 263:9015–9019.

Sambrook et al. (1989) In Molecular Cloning. A Laboratory Manual, Cold Spring Harbor, N.Y.

Scheibe R (1991) Redox-modulation of chloroplast enzymes. A common principle for individual control. Plant Physiol 96: 1–3.

Shernthaner J P, Matzke M A, Matzke A J M (1988) Endosperm-specific activity of a zein gene promoter in transgenic tobacco plants. EMBO (European Molecular Biology Organization) Journal 7(5):1249–1256.

Serre L., Lauriere C. (1990) Analytical Biochemistry. 186(2):312–315.

Shewry P R, Field J M, Kirkman M A, Faulks A J, Miflin B J. (1980). J. Exp. Botany 31:393–407.

Shi J. and Bhattacharyya M K (1996) A novel plasma membrane-bound thioredoxin from soybean. Plant Mol Biol 32:653–662.

Sissons M J, Lance R C M, Sparrow D H B. (1993) J. Cereal Sci. 7:19–24.

Sissons M J, Lance M, Wallace W. (1994) Cereal Chemistry. 71:520–521.

Smith and Waterman (1981) Adv. Appl. Math. 2:480.

Sørensen M B, Cameron-Mills V, Brandt A (1989) Transcriptional and post-transcriptional regulation of gene expression in developing barley endosperm. Mol Gen Genet 217: 195–201.

Sørensen M B, Muller M, Skerritt J, Simpson D (1996) Hordein promoter methylation and transcriptional activity in wild-type and mutant barley endosperm. Mol Gen Genet 250:750–760.

Suske G, Wagner W, Follman H (1979) NADPH thioredoxin reductase and a new thioredoxin from wheat. Z Naturforsch. C 34:214–221.

Takaiwa et al. (1995) Plant Science 111:39–49.

Torrent et al. (1997) Plant Molecular Biology 34:139–149.

U.S. application Serial No. 601126,736.

Vogt K, Follmann H (1986) Characterization of three different thioredoxins in wheat. Biochem Biophys Acta 873: 415–418.

Wan and Lemaux (1994) Plant Physiol. 104: 37–48.

Weissbach & Weissbach (1989) Methods for Plant Molecular Biology, Academic Press.

Wong et al. (1993) Cereal Chem. 70(1): 113–114.

Wong J H, Jiao J A, Kobrehel K, Buchanan B. (1995) Plant Physiol. 108:67.

Wu et al. (1998) Plant Journal 14:673–683.

Zhen et al. (1995) Plant Physiology 109:777–786.

All references, patents, patent applications, publications and references cited herein are hereby incorporated by reference in their entirety.

We claim:

1. A recombinant nucleic acid comprising a nucleic acid as set forth in SEQ ID NO:1.

2. A recombinant nucleic acid encoding an amino acid sequence as shown in SEQ ID NO:2.

3. A host cell comprising the recombinant nucleic acid of claim 1 or 2.

4. An expression vector comprising the recombinant nucleic acid of claim 1 or 2 operably linked to a transcriptional regulatory sequence.

5. A host cell comprising an expression vector comprising the recombinant nucleic acid of claim 1 or 2 operably linked to a transcriptional regulatory sequence active in said host cell.

6. A transgenic plant comprising the recombinant nucleic acid of claim 1 or 2.

7. A transgenic plant comprising an expression vector comprising the recombinant nucleic acid of claim 1 or 2 operably linked to transcriptional regulatory sequences active in said plant.

8. A transgenic plant comprising a host cell comprising an expression vector comprising the recombinant nucleic acid of claim 1 or 2 operably linked to a transcriptional regulatory sequence active in said cell.

9. The transgenic plant of claim 8 wherein said host cell is a seed cell.

10. A transgenic seed comprising the recombinant nucleic acid of claim 1 or 2 operably linked to transcriptional regulatory sequences active in said seed.

11. A method of expressing a thioredoxin h protein comprising culturing a host cell comprising the recombinant nucleic acid of claim 1 under conditions suitable for expression of said thioredoxin h protein.

12. A method of expressing a thioredoxin h protein comprising culturing a host cell comprising an expression vector comprising the recombinant nucleic acid of claim 1 operably linked to regulatory sequences active in said host cell under conditions suitable for expression of said thioredoxin h protein.

13. A method of expressing a thioredoxin h protein comprising culturing a transgenic plant comprising the recombinant nucleic acid of claim 1 under conditions suitable for expression of said thioredoxin h protein.

14. A method of expressing a thioredoxin h protein comprising culturing a transgenic plant comprising an expression vector comprising the recombinant nucleic acid of claim 1 operably linked to regulatory sequences active in said transgenic plant under conditions suitable for expression of said thioredoxin h protein.

15. A method of expressing a thioredoxin h protein comprising germinating the transgenic seed of claim 10.

16. The method of claim 11 further comprising recovering said protein.

17. The transgenic plant of claim 7, wherein said recombinant nucleic acid is overexpressed in said transgenic plant in comparison to a non-transgenic plant of the same species.

18. An isolated nucleic acid encoding an amino acid sequence as shown in SEQ ID NO:2.

19. A transgenic plant comprising the isolated nucleic acid of claim 18.

20. A transgenic seed comprising the isolated nucleic acid of claim 18 operably linked to a transcriptional regulatory sequence active in said seed.

21. A transgenic plant or at least a part of said plant overexpressing a barley thioredoxin h protein wherein said barley thioredoxin h protein comprises the amino acid sequence SEQ ID NO:2.

22. The method of claim 12 further comprising recovering said protein.

23. The method of claim 13 further comprising recovering said protein.

24. The method of claim 14 further comprising recovering said protein.

25. The method of claim 15 further comprising recovering said protein.

* * * * *